United States Patent
Diaz Fernández et al.

(10) Patent No.: US 9,487,513 B2
(45) Date of Patent: Nov. 8, 2016

(54) SUBSTITUTED PYRAZOLO[1,5-A]PYRIDINES, THEIR PREPARATION AND USE AS MEDICAMENTS

(71) Applicant: LABORATORIOS DEL DR. ESTEVE S.A., Barcelona (ES)

(72) Inventors: José Luis Diaz Fernández, Manresa (ES); Ma Rosa Cuberes Altisent, San Cugat del Valles (ES)

(73) Assignee: LABORATORIOS DE DR. ESTEVE S.A., Barcelona (ES)

( * ) Notice: Subject to any disclaimer, the term of this patent is extended or adjusted under 35 U.S.C. 154(b) by 0 days.

(21) Appl. No.: 14/379,844

(22) PCT Filed: Feb. 21, 2013

(86) PCT No.: PCT/EP2013/053427
§ 371 (c)(1),
(2) Date: Aug. 20, 2014

(87) PCT Pub. No.: WO2013/124341
PCT Pub. Date: Aug. 29, 2013

(65) Prior Publication Data
US 2015/0031678 A1  Jan. 29, 2015

(30) Foreign Application Priority Data
Feb. 21, 2012 (EP) .................................... 12382058

(51) Int. Cl.
  *C07D 471/04* (2006.01)
  *C07D 519/00* (2006.01)
  *C07D 491/107* (2006.01)
(52) U.S. Cl.
  CPC ......... *C07D 471/04* (2013.01); *C07D 491/107* (2013.01); *C07D 519/00* (2013.01)

(58) Field of Classification Search
CPC combination set(s) only.
See application file for complete search history.

(56) References Cited

U.S. PATENT DOCUMENTS

2010/0168125 A1*  7/2010  Gmeiner et al. ......... 514/253.04

FOREIGN PATENT DOCUMENTS

| CH | 544107 | * 12/1973 |
| EP | 1972628 | 9/2008 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Rautio et. al. "Prodrugs: design and clinical Applications" Nature Reviews Drug Discovery 2008, 7, 255-270.*
Beaumont "Design of Ester Prodrugs to Enhance Oral Absorption of Poorly Permeable Compounds: Challenges to the Discovery Scientist" Current Drug Metabolism, 2003, 4, 461-485.*
Henry R. Henze and Charles M. Blair "The Number of Structurally Isomeric Alcohols of the Methanol Series" Journal of the American Chemical Society 1931, 3042.*
Ehrlich "Dopamine D2, D3, and D4 Selective Phenylpiperazines as Molecular Probes to Explore the Origins of Subtype Specific Receptor Binding" Journal of Medicinal Chemistry, 52(15), 4923-4935 2009.*
International Search Report for PCT/EP2013/053427 of May 30, 2013.

* cited by examiner

*Primary Examiner* — David K O'Dell
(74) *Attorney, Agent, or Firm* — Hueschen and Sage

(57) ABSTRACT

The present invention relates to new substituted pyrazolo[1,5-a]pyridine having a great affinity for sigma receptors, especially sigma-1 receptor, as well as to the process for the preparation thereof, to compositions comprising them, and to their use as medicaments.

14 Claims, No Drawings

SUBSTITUTED PYRAZOLO[1,5-A]PYRIDINES, THEIR PREPARATION AND USE AS MEDICAMENTS

FIELD OF THE INVENTION

The present invention relates to new substituted pyrazolo [1,5-a]pyridine having a great affinity for sigma receptors, especially sigma-1 receptor, as well as to the process for the preparation thereof, to compositions comprising them, and to their use as medicaments.

BACKGROUND OF THE INVENTION

The search for new therapeutic agents has been greatly aided in recent years by better understanding of the structure of proteins and other biomolecules associated with target diseases. One important class of these proteins are the sigma (σ) receptors, cell surface receptors of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, Pharmacological Reviews, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)SKF 10047, (+)cyclazocine, and (+)pentazocine and also for some narcoleptics such as haloperidol.

"The sigma receptor/s" as used in this application is/are well known and defined using the following citation: This binding site represents a typical protein different from opioid, NMDA, dopaminergic, and other known neurotransmitter or hormone receptor families (G. Ronsisvalle et al. Pure Appl. Chem. 73, 1499-1509 (2001)).

The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma 2 (σ-2) site. Haloperidol has similar affinities for both subtypes.

The Sigma-1 receptor is a non-opiaceous type receptor expressed in numerous adult mammal tissues (e.g. central nervous system, ovary, testicle, placenta, adrenal gland, spleen, liver, kidney, gastrointestinal tract) as well as in embryo development from its earliest stages, and is apparently involved in a large number of physiological functions. Its high affinity for various pharmaceuticals has been described, such as for SKF-10047, (+)-pentazocine, haloperidol and rimcazole, among others, known ligands with analgesic, anxiolytic, antidepressive, antiamnesic, antipsychotic and neuroprotective activity. Sigma-1 receptor is of great interest in pharmacology in view of its possible physiological role in processes related to analgesia, anxiety, addiction, amnesia, depression, schizophrenia, stress, neuroprotection and psychosis [Kaiser et al (1991) Neurotransmissions 7 (1): 1-5], [Walker, J. M. et al, Pharmacological Reviews, 1990, 42, 355] and [Bowen W. D. (2000) Pharmaceutica Acta Helvetiae 74: 211-218].

The Sigma-2 receptor is also expressed in numerous adult mammal tissues (e.g. nervous system, immune system, endocrine system, liver, kidney). Sigma-2 receptors can be components in a new apoptosis route that may play an important role in regulating cell proliferation or in cell development. This route seems to consist of Sigma-2 receptors joined to intracellular membranes, located in organelles storing calcium, such as the endoplasmic reticulum and mitochondria, which also have the ability to release calcium from these organelles. The calcium signals can be used in the signaling route for normal cells and/or in induction of apoptosis.

Agonists of Sigma-2 receptors induce changes in cell morphology, apoptosis in several types of cell lines and regulate the expression of p-glycoprotein mRNA, so that they are potentially useful as antineoplasic agents for treatment of cancer. In fact, Sigma-2 receptor agonists have been observed to induce apoptosis in mammary tumour cell lines resistant to common antineoplasic agents that damage DNA. In addition, agonists of Sigma-2 receptors enhance the cytotoxic effects of these antineoplasic agents at concentrations in which the agonist is not cytotoxic. Thus, agonists of Sigma-2 receptors can be used as antineoplasic agents at doses inducing apoptosis or at sub-toxic doses in combination with other antineoplasic agents to revert the resistance to the drug, thereby allowing using lower doses of the antineoplasic agent and considerably reducing its adverse effects.

Antagonists of Sigma-2 receptors can prevent the irreversible motor side effects caused by typical neuroleptic agents. In fact, it has been found that antagonists of Sigma-2 receptors can be useful as agents for improving the weakening effects of delayed dyskinesia appearing in patients due to chronic treatment of psychosis with typical antipsychotic drugs, such as haloperidol. Sigma-2 receptors also seem to play a role in certain degenerative disorders in which blocking these receptors could be useful.

Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. Trends Pharmacol. Sci., 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. Proc. Natl. Acad. Sci., 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Different sigma receptor ligands have been reported.

For instance, the international patent application WO 2007/098961 describes 4,5,6,7 tetrahydrobenzo[b]thiophene derivatives having pharmacological activity towards the sigma receptor.

Spiro[benzopyran] or spiro[benzofuran] derivatives were also disclosed in EP 1 847 542 as well as pyrazole derivatives (EP 1 634 873) with pharmacological activity on sigma receptors.

WO 2009/071657 also reports tricyclic triazolic compounds having good activity towards sigma receptors.

Although, some pyrazolo[1,5-a]pyridine have been disclosed in the prior art, such as for instance, in WO 2008/

113559, the present invention discloses novel pyrazolo[1,5-a]pyridines. In addition, there is no prior art suggesting that pyrazolo[1,5-a]pyridines can be active towards sigma receptors.

Nevertheless, there is still a need to find compounds having pharmacological activity towards the sigma receptor, being both effective and selective, and having good "drugability" properties, i.e. good pharmaceutical properties related to administration, distribution, metabolism and excretion.

SUMMARY OF THE INVENTION

The present invention discloses novel compounds with great affinity to sigma receptors which might be used for the treatment of sigma related disorders or diseases.

Specifically, it is an object of the present invention novel substituted pyrazolo[1,5-a]pyridine of general formula (I):

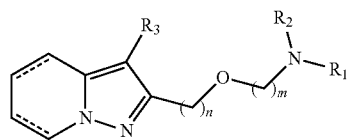

Another object of the invention is the different processes for preparation of compounds of general formula (I).

Another object of the invention refers to the use of such compounds of general formula (I) for the treatment or prophylaxis of sigma receptor mediated diseases or conditions, especially sigma-1 mediated diseases or conditions. Within the group of diseases or conditions mediated by sigma receptor for which the compounds of the invention are effective diarrhea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive dyskinesia, ischemic stroke, epilepsy, stroke, stress, cancer, psychotic conditions, in particular depression, anxiety or schizophrenia; inflammation or autoimmune diseases, may be cited. Compounds of the invention are very good and are especially effective for the treatment and prophylaxis of pain, especially neuropathic pain, inflammatory pain or other pain conditions involving allodynia and/or hyperalgesia.

It is also an object of the invention pharmaceutical compositions comprising one or more compounds of general formula (I) with at least one pharmaceutically acceptable excipient. The pharmaceutical compositions in accordance with the invention can be adapted in order to be administered by any route of administration, be it orally or parenterally, such as pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

DETAILED DESCRIPTION OF THE INVENTION

The invention first relates to a compound of general formula (I):

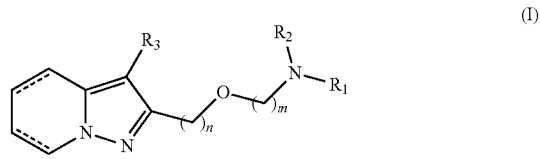

wherein
$R_1$ and $R_2$ independently represent hydrogen; a branched or unbranched, saturated or unsaturated, optionally at least mono-substituted, aliphatic radical $C_{1-10}$; a substituted or unsubstituted aryl; a substituted or unsubstituted heteroaryl radical $C_{1-10}$; a substituted or unsubstituted $C_{3-9}$ cycloalkyl radical optionally containing at least one heteroatom as ring member selected from N, O or S; a cycloalkylalkyl radical $C_{1-10}$; an arylalkyl radical $C_{1-10}$; an heteroarylalkyl radical $C_{1-10}$ or an aryloxy radical;
or $R_1$ and $R_2$ together with the bridging nitrogen form a $C_{3-9}$ cycloalkyl optionally containing at least one additional heteroatom as a ring member selected from N, O or S and optionally substituted;
or $R_1$ and $R_2$ together with the bridging nitrogen form $C_{3-9}$ cycloalkyl optionally containing at least one additional heteroatom as a ring member selected from N, O or S, which may be condensed to form a ring system with another $C_{3-9}$ cycloalkyl optionally containing at least one heteroatom as a ring member selected from N, O or S; or which may be condensed to form a ring system with an aryl radical; or which may be spirofused to an aryl or heteroaryl group;
$R_3$ represents hydrogen or halogen;
n is 0, 1 or 2;
m is 1, 2, 3 or 4;
and - - - - - represents an optionally double bond.
with the proviso that when $R_1$ and $R_2$ together with the bridging nitrogen form a piperazinyl radical N-substituted with a chlorophenyl, a dichlorophenyl or a methoxy phenyl, $R_3$ is hydrogen and n is 0, m is not 4; and
with the proviso that when $R_1$ and $R_2$ together with the bridging nitrogen form a piperidine, $R_3$ is hydrogen and n is 0, m is not 3;
or a pharmaceutically acceptable salt, isomer, prodrug or solvate thereof.

"Halogen" or "halo" as referred in the present invention represent fluorine, chlorine, bromine or iodine.

Aliphatic group/radicals $C_{1-10}$, as referred to in the present invention, are optionally mono- or polysubstituted and may be branched or unbranched, saturated or unsaturated. Unsaturated aliphatic groups, as defined in the present invention, include alkyl, alkenyl and alkinyl radicals. Preferred aliphatic radicals according to the present invention include but are not restricted to methyl, ethyl, vinyl (ethenyl), ethinyl, propyl, n-propyl, isopropyl, allyl (2-propenyl), 1-propinyl, methylethyl, butyl, n-butyl, iso-butyl, sec-butyl, tert-butyl butenyl, butinyl, 1-methylpropyl, 2-methylpropyl, 1,1-dimethylethyl, pentyl, n-pentyl, isopentyl, 1,1-dimethylpropyl, 1,2-dimethylpropyl, 2,2-dimethylpropyl, hexyl, 1-methylpentyl, n-heptyl, n-octyl, n-nonyl and n-decyl. Preferred substituents for aliphatic radicals, according to the present invention, are a $C_{1-6}$ alkyl group, cycloalkyl $C_{3-9}$ group, a linear or branched $C_{1-6}$ alkoxy group, —F, —Cl, —I, —Br, —$CF_3$, —$CH_2F$, —$CHF_2$, —CN, —OH, —SH, —$NH_2$, oxo, —(C=O)R', —SR', —SOR', —$SO_2$R', —NHR', —NR'R" whereby R' and optionally R" for each substitutent independently represents a linear or branched $C_{1-6}$-alkyl group.

Alkyl group/radicals, as referred to in the present invention, are saturated aliphatic radicals. They may be linear or branched and are optionally substituted. $C_{1-6}$ alkyl as expressed in the present invention means an alkyl radical of 1, 2, 3, 4, 5 or 6 carbon atoms.

Cycloalkyl group/radical $C_{3-9}$, as referred to in the present invention, are understood as meaning saturated and unsaturated (but not aromatic), cyclic hydrocarbons, which can optionally be unsubstituted, mono- or polysubstituted. In these radicals, for example $C_{3-4}$ cycloalkyl represents C3- or C4-cycloalkyl, $C_{3-5}$-cycloalkyl represents C3-, C4- or C5-cycloalkyl, etc. With respect to cycloalkyl, the term also includes saturated cycloalkyls in which optionally at least one carbon atom may be replaced by a heteroatom, preferably S, N or O. However, mono- or polyunsaturated, preferably monounsaturated, cycloalkyls without a heteroatom in the ring also in particular fall under the term cycloalkyl as long as the cycloalkyl is not an aromatic system. Examples for cycloalkyl radical preferably include but are not restricted to cyclopropyl, 2-methylcyclopropyl, cyclopropylmethyl, cyclobutyl, cyclopentyl, cyclopentylmethyl, cyclohexyl, cycloheptyl, cyclooctyl, acetyl, tert-butyl, adamantyl, noradamantyl, pyrroline, pyrrolidine, pyrrolidineone, pyrazoline, pyrazolinone, oxopyrazolinone, aziridine, azetidine, tetrahydropyrrole, oxirane, oxetane, dioxetane, tetrahydropyrane, tetrahydrofurane, tetrahydro-2H-thiopyran, dioxane, dioxolane, oxathiolane, oxazolidine, thiirane, thietane, thiolane, thiane, thiazolidine, piperidine, piperazine, morpholine or azepane. Cycloalkyl radicals $C_{3-9}$, as defined in the present invention, are optionally mono- or polysubstituted by substitutents independently selected from a $C_{1-6}$ alkyl group, a phenyl group, a benzyl group, a linear or branched $C_{1-6}$ alkoxy group, —F, —Cl, —I, —Br, —$CF_3$, —$CH_2F$, —$CHF_2$, —CN, —OH, —SH, —$NH_2$, oxo, —(C=O)R', —SR', —SOR', —$SO_2$R', —NHR', —NR'R" whereby R' and optionally R" for each substitutent independently represents a linear or branched $C_{1-6}$-alkyl group.

A cycloalkylalkyl group/radical $C_{1-10}$, as defined in the present invention, comprises a linear or branched, optionally at least mono-substituted alkyl chain of 1 to 10 atoms which is bonded to a cycloalklyl group, as defined above. The cycloalkylalkyl radical is bonded to the molecule through the alkyl chain. A preferred cycloalkylalkyl group/radical is a cyclopropyl methyl group, wherein the alkyl chain is optionally branched or substituted. Preferred substituents for cycloalkylalkyl group/radical, according to the present invention, are F, Cl, Br, I, $NH_2$, SH, OH, $SO_2$, $CF_3$, carboxy, amido, cyano, carbamyl, nitro, phenyl, benzyl, —$SO_2NH_2$, $C_{1-6}$ alkyl and/or $C_{1-6}$-alkoxy.

An aryl group/radical, as referred to in the present invention, is understood as meaning ring systems with at least one aromatic ring but without heteroatoms even in only one of the rings. These aryl radicals may optionally be mono- or polysubstituted by substitutents independently selected from a $C_{1-6}$ alkyl group, a linear or branched $C_{1-6}$ alkoxy group, an optionally at least mono-substituted phenyl group, —F, —Cl, —I, —Br, —$CF_3$, —$CH_2F$, —$CHF_2$, —CN, —OH, —SH, —$NH_2$, oxo, —(C=O)R', —SR', —SOR', —$SO_2$R', —N(C=O) OR', —NHR', —NR'R" whereby R' and optionally R" for each substitutent independently represents a linear or branched $C_{1-6}$-alkyl group. Preferred examples of aryl radicals include but are not restricted to phenyl, naphthyl, fluoranthenyl, fluorenyl, tetralinyl or indanyl or anthracenyl radicals, which may optionally be mono- or polysubstituted, if not defined otherwise.

An arylalkyl radical $C_{1-10}$, as defined in the present invention, comprises a linear or branched, optionally at least mono-substituted alkyl chain of 1 to 10 carbon atoms which is bonded to an aryl group, as defined above. The arylalkyl radical is bonded to the molecule through the alkyl chain. A preferred arylalkyl radical is a benzyl group, wherein the alkyl chain is optionally branched or substituted. Preferred substituents for arylalkyl radicals, according to the present invention, are F, Cl, Br, I, $NH_2$, SH, OH, $SO_2$, $CF_3$, carboxy, amido, cyano, carbamyl, nitro, phenyl, benzyl, —$SO_2NH_2$, $C_{1-6}$ alkyl and/or $C_{1-6}$ alkoxy.

A heteroaryl group/radical, is understood as meaning heterocyclic ring systems which have at least one aromatic ring and may optionally contain one or more heteroatoms from the group consisting of nitrogen, oxygen and/or sulfur and may optionally be mono- or polysubstituted by substitutents independently selected from a $C_{1-6}$ alkyl group, a linear or branched $C_{1-6}$ alkoxy group, F, Cl, I, Br, $CF_3$, $CH_2F$, $CHF_2$, CN, OH, SH, $NH_2$, oxo, (C=O)R', SR', SOR', $SO_2$R', NHR', NR'R" whereby R' and optionally R" for each substitutent independently represents a linear or branched $C_{1-6}$ alkyl group. Preferred examples of heteroaryls include but are not restricted to furan, benzofuran, thiophene, benzothiophene, pyrrole, pyridine, pyrimidine, pyridazine, pyrazine, quinoline, isoquinoline, phthalazine, benzo-1,2,5-thiadiazole, benzothiazole, indole, benzotriazole, benzodioxolane, benzodioxane, benzimidzole, carbazole and quinazoline.

Heteroarylalkyl group/radical $C_{1-10}$ as defined in the present invention, comprises a linear or branched, optionally at least mono-substituted alkyl chain of 1 to 10 carbon atoms which is bonded to an heteroaryl group, as defined above. The heteroarylalkyl radical is bonded to the molecule through the alkyl chain. A preferred heteroarylalkyl radical is a methylpiridinyl group, wherein the alkyl chain is optionally branched or substituted. Preferred substituents for heteroarylalkyl radicals, according to the present invention, are F, Cl, Br, I, $NH_2$, SH, OH, $SO_2$, $CF_3$, carboxy, amido, cyano, carbamyl, nitro, phenyl, benzyl, —$SO_2NH_2$, $C_{1-6}$ alkyl and/or $C_{1-6}$ alkoxy.

The term "condensed" according to the present invention means that a ring or ring-system is attached to another ring or ring-system, whereby the terms "annulated" or "annelated" are also used by those skilled in the art to designate this kind of attachment.

The term "spirofused" or "spirofusion" means that a ring or ring system is attached to another ring or ring system through at least one spiro atom shared by either ring or ring system.

The term "ring system" according to the present invention refers to ring systems comprising saturated, unsaturated or aromatic carbocyclic ring systems which contain optionally at least one heteroatom as ring member and which are optionally at least mono-substituted. Said ring systems may be condensed to other carbocyclic ring systems such as aryl groups, naphtyl groups, heteroaryl groups, cycloalkyl groups, etc.

Cyclyl groups/radicals or cyclic systems, as defined in the present invention, comprise any saturated, unsaturated or aromatic carbocyclic ring systems which contain optionally at least one heteroatom as ring member and which are optionally at least mono-substituted. Cyclyl groups or cyclic systems preferably comprise aryl, heteroaryl, cyclyl, heterocylcyl and/or spiro ring systems.

Heterocyclyl groups/radicals or heterocyclic systems, as defined in the present invention, comprise any saturated, unsaturated or aromatic carbocyclic ring systems which are optionally at least mono-substituted and which contain at least one heteroatom as ring member. Preferred heteroatoms for these heterocyclyl groups are N, S or O. Preferred substituents for heterocyclyl radicals, according to the present invention, are F, Cl, Br, I, $NH_2$, SH, OH, $SO_2$, $CF_3$, carboxy, amido, cyano, carbamyl, nitro, phenyl, benzyl, —$SO_2NH_2$, $C_{1-6}$ alkyl and/or $C_{1-6}$-alkoxy.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are formed via ionic interactions.

The term "physiologically acceptable salt" is understood in particular, in the context of this invention, as salt (as defined above) formed either with a physiologically tolerated acid, that is to say salts of the particular active compound with inorganic or organic acids which are physiologically tolerated—especially if used on humans and/or mammals—or with at least one, preferably inorganic, cation which are physiologically tolerated—especially if used on humans and/or mammals. Examples of physiologically tolerated salts of particular acids are salts of: hydrochloric acid, hydrobromic acid, sulfuric acid, hydrobromide, monohydrobromide, monohydrochloride or hydrochloride, methiodide, methanesulfonic acid, formic acid, acetic acid, oxalic acid, succinic acid, malic acid, tartaric acid, mandelic acid, fumaric acid, lactic acid, citric acid, glutamic acid, hippuric acid picric acid and/or aspartic acid. Examples of physiologically tolerated salts of particular bases are salts of alkali metals and alkaline earth metals and with $NH_4$.

The term "solvate" is to be understood as meaning any form of the active compound according to the invention in which this compound has attached to it via non-covalent binding another molecule (most likely a polar solvent) especially including hydrates and alcoholates, e.g. methanolate.

The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the compounds of the invention: esters, amino acid esters, phosphate esters, metal salts sulfonate esters, carbamates, and amides. Examples of well known methods of producing a prodrug of a given active compound are known to those skilled in the art and can be found e.g. in Krogsgaard-Larsen et al. "Textbook of Drug design and Discovery" Taylor & Francis (april 2002).

Any compound that is a prodrug of a compound of formula (I) is within the scope of the invention. Particularly favored prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

In a particular and preferred embodiment of the invention $R_1$ and $R_2$ independently represent hydrogen; a branched or unbranched, saturated or unsaturated, optionally at least mono-substituted, aliphatic radical $C_{1-10}$; a substituted or unsubstituted $C_{3-9}$ cycloalkyl radical optionally containing at least one heteroatom as ring member selected from N, O or S; a cycloalkylalkyl radical $C_{1-10}$; an arylalkyl radical $C_{1-10}$; an heteroarylalkyl radical $C_{1-10}$. More particularly $R_1$ and $R_2$ may independently represent hydrogen, a methyl, an ethyl, a propyl or a group selected from:

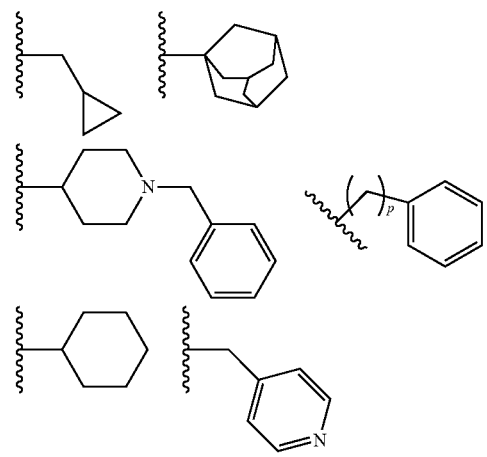

where p is 1 or 2.

In another preferred embodiment $R_1$ and $R_2$ together with the bridging nitrogen form a $C_{3-9}$ cycloalkyl optionally containing at least one additional heteroatom as a ring member selected from N, O or S and optionally substituted. The proviso that when $R_1$ and $R_2$ together with the bridging nitrogen form a piperazinyl radical N-substituted with a chlorophenyl, a dichlorophenyl or a methoxy phenyl, $R_3$ is hydrogen and n is 0, m is not 4; as well as the proviso that when $R_1$ and $R_2$ together with the bridging nitrogen form a piperidine, $R_3$ is hydrogen and n is 0, m is not 3 apply to these embodiments of the invention. Also in this embodiment of the invention the $C_{3-9}$ cycloalkyl optionally containing at least one additional heteroatom as a ring member selected from N, O or S formed by $R_1$ and $R_2$ together with the bridging nitrogen can be optionally but preferably substituted by a methyl, an ethyl, an isopropyl, a tertbutyl or a group selected from:

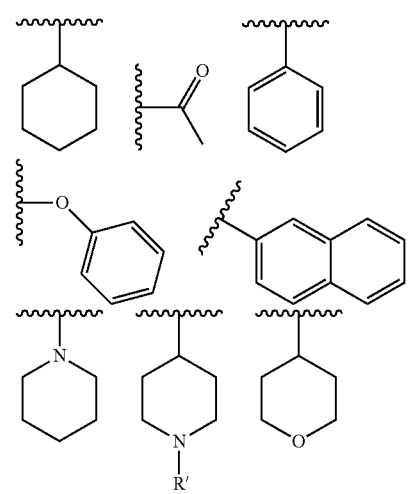

In a still particular and preferred embodiment of the invention $R_1$ and $R_2$ together with the bridging nitrogen represents one of the following moieties:

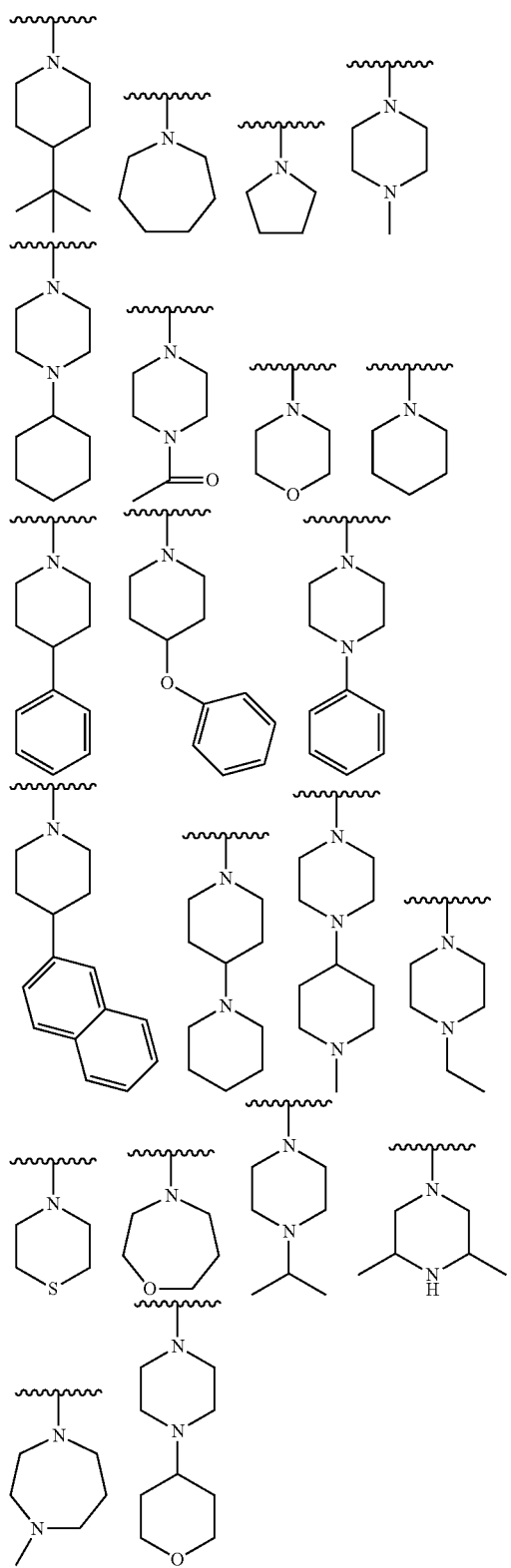

In another particular and preferred embodiment of the invention $R_1$ and $R_2$ together with the bridging nitrogen form $C_{3-9}$ cycloalkyl which is condensed or spirofused to other ring or ring system to form one of the following moieties:

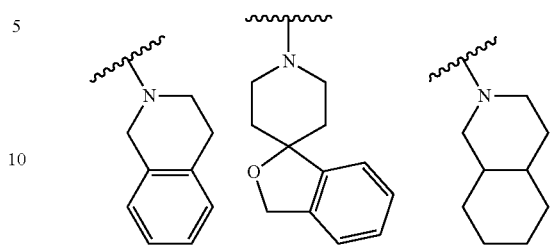

In preferred variants of the invention, the sigma ligand of formula (I) is selected from:

2-((4-(4-tert-butylpiperidin-1-yl)butoxy)methyl)pyrazolo[1,5-a]pyridine maleate;
2-((2-(azepan-1-yl)ethoxy)methyl)pyrazolo[1,5-a]pyridine maleate;
N-(cyclopropylmethyl)-N-propyl-4-(pyrazolo[1,5-a]pyridin-2-ylmethylpyrazolo[1,5-a]pyridin-2-ylmethoxy)butan-1-amine maleate;
2-(4-(pyrazolo[1,5-a]pyridin-2-ylmethylpyrazolo[1,5-a]pyridin-2-ylmethoxy)butyl)-1,2,3,4-tetrahydroisoquinoline maleate;
N-adamantyl-4-(pyrazolo[1,5-a]pyridin-2-ylmethylpyrazolo[1,5-a]pyridin-2-ylmethoxy)butan-1-amine maleate;
1'-(4-(pyrazolo[1,5-a]pyridin-2-ylmethylpyrazolo[1,5-a]pyridin-2-ylmethoxy)butyl)-3H-spiro[isobenzofuran-1,4'-piperidine]maleate;
2-((2-(pyrrolidin-1-yl)ethoxy)methyl)pyrazolo[1,5-a]pyridine maleate;
2-((4-(azepan-1-yl)butoxy)methyl)pyrazolo[1,5-a]pyridine maleate;
2-((4-(4-methylpiperazin-1-yl)butoxy)methyl)pyrazolo[1,5-a]pyridine maleate;
2-((4-(4-cyclohexylpiperazin-1-yl)butoxy)methyl)pyrazolo[1,5-a]pyridine maleate;
1-(4-(4-(pyrazolo[1,5-a]pyridin-2-ylmethylpyrazolo[1,5-a]pyridin-2-ylmethoxy)butyl)piperazin-1-yl)ethanone;
1-benzyl-N-methyl-N-(4-(pyrazolo[1,5-a]pyridin-2-yloxy)butyl)piperidin-4-amine difumarate;
4-(2-(pyrazolo[1,5-a]pyridin-2-yloxy)ethyl)morpholine;
2-(2-(piperidin-1-yl)ethoxy)pyrazolo[1,5-a]pyridine oxalate;
2-(2-(pyrrolidin-1-yl)ethoxy)pyrazolo[1,5-a]pyridine oxalate;
N,N-diethyl-2-(pyrazolo[1,5-a]pyridin-2-yloxy)ethanamine oxalate;
4-(4-(pyrazolo[1,5-a]pyridin-2-yloxy)butyl)morpholine oxalate;
2-(4-(piperidin-1-yl)butoxy)pyrazolo[1,5-a]pyridine oxalate;
N,N-diethyl-4-(pyrazolo[1,5-a]pyridin-2-yloxy)butan-1-amine oxalate;
2-(4-(pyrrolidin-1-yl)butoxy)pyrazolo[1,5-a]pyridine oxalate;
2-(4-(4-phenylpiperidin-1-yl)butoxy)pyrazolo[1,5-a]pyridine oxalate;
N-benzyl-N-methyl-4-(pyrazolo[1,5-a]pyridin-2-yloxy)butan-1-amine oxalate;
2-(4-(4-phenoxypiperidin-1-yl)butoxy)pyrazolo[1,5-a]pyridine oxalate;
N-benzyl-N-methyl-2-(pyrazolo[1,5-a]pyridin-2-yloxy)ethanamine oxalate;

2-(4-(4-phenylpiperazin-1-yl)butoxy)pyrazolo[1,5-a]pyridine oxalate;
2-(4-(4-(naphthalen-2-yl)piperidin-1-yl)butoxy)pyrazolo[1,5-a]pyridine;
1'-(4-(pyrazolo[1,5-a]pyridin-2-yloxy)butyl)-3H-spiro[isobenzofuran-1,4'-piperidine]oxalate;
2-(4-(4-cyclohexylpiperazin-1-yl)butoxy)pyrazolo[1,5-a]pyridine2-(4-(4-cyclohexylpiperazin-1-yl)butoxy)pyrazolo[1,5-a]pyridine dimaleate;
2-(4-(4-tert-butylpiperidin-1-yl)butoxy)pyrazolo[1,5-a]pyridine hydrochloride;
N-methyl-N-phenethyl-4-(pyrazolo[1,5-a]pyridin-2-yloxy)butan-1-amine hydrochloride;
N-methyl-4-(pyrazolo[1,5-a]pyridin-2-yloxy)-N-(pyridin-4-ylmethyl)butan-1-amine dihydrochloride;
2-(4-(1,4'-bipiperidin-1'-yl)butoxy)pyrazolo[1,5-a]pyridine difumarate;
2-(4-(pyrazolo[1,5-a]pyridin-2-yloxy)butyl)decahydroisoquinoline fumarate;
N-(cyclopropylmethyl)-N-propyl-4-(pyrazolo[1,5-a]pyridin-2-yloxy)butan-1-amine maleate;
2-(4-(pyrazolo[1,5-a]pyridin-2-yloxy)butyl)-1,2,3,4-tetrahydroisoquinoline maleate;
N-adamantyl-4-(pyrazolo[1,5-a]pyridin-2-yloxy)-butan-1-amine maleate;
2-(4-(4-(1-methylpiperidin-4-yl)piperazin-1-yl)butoxy)pyrazolo[1,5-a]pyridine dimaleate;
2-(2-(4-tert-butylpiperidin-1-yl)ethoxy)pyrazolo[1,5-a]pyridine maleate;
N-methyl-N-phenethyl-2-(pyrazolo[1,5-a]pyridin-2-yloxy)ethanamine maleate;
1-benzyl-N-methyl-N-(2-(pyrazolo[1,5-a]pyridin-2-yloxy)ethyl)piperidin-4-amine dimaleate;
2-(2-(pyrazolo[1,5-a]pyridin-2-yloxy)ethyl)decahydroisoquinoline maleate;
N-(cyclopropylmethyl)-N-(2-(pyrazolo[1,5-a]pyridin-2-yloxy)ethyl)propan-1-amine maleate;
2-(2-(pyrazolo[1,5-a]pyridin-2-yloxy)ethyl)-1,2,3,4-tetrahydroisoquinoline maleate;
2-(2-(1,4'-bipiperidin-1'-yl)ethoxy)pyrazolo[1,5-a]pyridine dimaleate;
2-(2-(4-(1-methylpiperidin-4-yl)piperazin-1-yl)ethoxy)pyrazolo[1,5-a]pyridine dimaleate;
2-(2-(4-cyclohexylpiperazin-1-yl)ethoxy)pyrazolo[1,5-a]pyridine dimaleate;
1'-(2-(pyrazolo[1,5-a]pyridin-2-yloxy)ethyl)-3H-spiro[isobenzofuran-1,4'-piperidine]dimaleate;
2-(4-(azepan-1-yl)butoxy)pyrazolo[1,5-a]pyridine maleate;
N-(4-(pyrazolo[1,5-a]pyridin-2-yloxy)butyl)cyclohexanamine maleate;
(4aR,8aS)-2-(4-(pyrazolo[1,5-a]pyridin-2-yloxy)butyl)decahydroisoquinoline maleate;
2-(2-(4-ethylpiperazin-1-yl)ethoxy)-4,5,6,7-tetrahydropyrazolo[1,5-a]pyridine maleate;
2-(2-(azepan-1-yl)ethoxy)-4,5,6,7-tetrahydropyrazolo[1,5-a]pyridine maleate;
2-(2-(piperidin-1-yl)ethoxy)-4,5,6,7-tetrahydropyrazolo[1,5-a]pyridine oxalate;
N,N-diethyl-2-(4,5,6,7-tetrahydropyrazolo[1,5-a]pyridin-2-yloxy)ethanamine oxalate;
4-(4-(4,5,6,7-tetrahydropyrazolo[1,5-a]pyridin-2-yloxy)butyl)morpholine oxalate;
4-(2-(4,5,6,7-tetrahydropyrazolo[1,5-a]pyridin-2-yloxy)ethyl)morpholine oxalate;
2-(2-(pyrrolidin-1-yl)ethoxy)-4,5,6,7-tetrahydropyrazolo[1,5-a]pyridine oxalate;
2-(4-(pyrrolidin-1-yl)butoxy)-4,5,6,7-tetrahydropyrazolo[1,5-a]pyridine oxalate;
2-(4-(piperidin-1-yl)butoxy)-4,5,6,7-tetrahydropyrazolo[1,5-a]pyridine oxalate;
2-(4-(piperidin-1-yl)butoxy)-4,5,6,7-tetrahydropyrazolo[1,5-a]pyridine maleate;
N,N-diethyl-4-(4,5,6,7-tetrahydropyrazolo[1,5-a]pyridin-2-yloxy)butan-1-amine oxalate;
2-(4-(4-phenylpiperidin-1-yl)butoxy)-4,5,6,7-tetrahydropyrazolo[1,5-a]pyridine oxalate N-benzyl-N-methyl-2-(4,5,6,7-tetrahydropyrazolo[1,5-a]pyridin-2-yloxy)ethanamine oxalate;
2-(4-(4-tert-butylpiperidin-1-yl)butoxy)-4,5,6,7-tetrahydropyrazolo[1,5-a]pyridine maleate;
2-(2-(4-tert-butylpiperidin-1-yl)ethoxy)-4,5,6,7-tetrahydropyrazolo[1,5-a]pyridine maleate;
1-benzyl-N-methyl-N-(4-(4,5,6,7-tetrahydropyrazolo[1,5-a]pyridin-2-yloxy)butyl)piperidin-4-amine dimaleate;
2-(4-(4,5,6,7-tetrahydropyrazolo[1,5-a]pyridin-2-yloxy)butyl)decahydroisoquinoline maleate;
2-(4-(4-cyclohexylpiperazin-1-yl)butoxy)-4,5,6,7-tetrahydropyrazolo[1,5-a]pyridine maleate;
1'-(4-(4,5,6,7-tetrahydropyrazolo[1,5-a]pyridin-2-yloxy)butyl)-3H-spiro[isobenzofuran-1,4'-piperidine]maleate;
2-(2-(4-cyclohexylpiperazin-1-yl)ethoxy)-4,5,6,7-tetrahydropyrazolo[1,5-a]pyridine maleate;
1-benzyl-N-methyl-N-(2-(4,5,6,7-tetrahydropyrazolo[1,5-a]pyridin-2-yloxy)ethyl)piperidin-4-amine maleate;
2-(2-(4-(1-methylpiperidin-4-yl)piperazin-1-yl)ethoxy)-4,5,6,7-tetrahydropyrazolo[1,5-a]pyridine maleate;
1'-(2-(4,5,6,7-tetrahydropyrazolo[1,5-a]pyridin-2-yloxy)ethyl)-3H-spiro[isobenzofuran-1,4'-piperidine]maleate;
N-adamantyl-2-(4,5,6,7-tetrahydropyrazolo[1,5-a]pyridin-2-yloxy)ethanamine maleate;
2-(2-(1,4'-bipiperidin-1'-yl)ethoxy)-4,5,6,7-tetrahydropyrazolo[1,5-a]pyridine maleate;
2-(2-(4,5,6,7-tetrahydropyrazolo[1,5-a]pyridin-2-yloxy)ethyl)-1,2,3,4-tetrahydroisoquinoline maleate;
2-(4-(azepan-1-yl)butoxy)-4,5,6,7-tetrahydropyrazolo[1,5-a]pyridine maleate
2-(4-(1,4'-bipiperidin-1'-yl)butoxy)-4,5,6,7-tetrahydropyrazolo[1,5-a]pyridine maleate;
N-(cyclopropylmethyl)-N-propyl-4-(4,5,6,7-tetrahydropyrazolo[1,5-a]pyridin-2-yloxy)butan-1-amine maleate;
(4aR,8aS)-2-(4-(4,5,6,7-tetrahydropyrazolo[1,5-a]pyridin-2-yloxy)butyl)decahydroisoquinoline maleate;
N-benzyl-N-methyl-4-(4,5,6,7-tetrahydropyrazolo[1,5-a]pyridin-2-yloxy)butan-1-amine maleate;
N-adamantyl-4-(4,5,6,7-tetrahydropyrazolo[1,5-a]pyridin-2-yloxy)butan-1-amine maleate;
2-(4-(4,5,6,7-tetrahydropyrazolo[1,5-a]pyridin-2-yloxy)butyl)-1,2,3,4-tetrahydroisoquinoline maleate;
N-(4-(4,5,6,7-tetrahydropyrazolo[1,5-a]pyridin-2-yloxy)butyl)cyclohexanamine maleate;
4-(4-(4,5,6,7-tetrahydropyrazolo[1,5-a]pyridin-2-yloxy)butyl)thiomorpholine maleate;
(4aR,8aS)-2-(2-(4,5,6,7-tetrahydropyrazolo[1,5-a]pyridin-2-yloxy)ethyl)decahydroisoquinoline maleate;
4-(2-(4,5,6,7-tetrahydropyrazolo[1,5-a]pyridin-2-yloxy)ethyl)-1,4-oxazepane maleate;
4-(4-(4,5,6,7-tetrahydropyrazolo[1,5-a]pyridin-2-yloxy)butyl)-1,4-oxazepane maleate;
N-(cyclopropylmethyl)-N-(2-(4,5,6,7-tetrahydropyrazolo[1,5-a]pyridin-2-yloxy)ethyl)propan-1-amine maleate;
2-(2-(4-isopropylpiperazin-1-yl)ethoxy)-4,5,6,7-tetrahydropyrazolo[1,5-a]pyridine maleate;

2-(4-(4-isopropylpiperazin-1-yl)butoxy)-4,5,6,7-tetrahydropyrazolo[1,5-a]pyridine maleate;
2-(4-(4-methylpiperazin-1-yl)butoxy)-4,5,6,7-tetrahydropyrazolo[1,5-a]pyridine maleate;
2-(4-((3S,5R)-3,5-dimethylpiperazin-1-yl)butoxy)-4,5,6,7-tetrahydropyrazolo[1,5-a]pyridine maleate;
1-(4-(4-(4,5,6,7-tetrahydropyrazolo[1,5-a]pyridin-2-yloxy)butyl)piperazin-1-yl)ethanone maleate;
2-(4-(4-methyl-1,4-diazepan-1-yl)butoxy)-4,5,6,7-tetrahydropyrazolo[1,5-a]pyridine maleate;
2-(3-(4-methylpiperazin-1-yl)propoxy)-4,5,6,7-tetrahydropyrazolo[1,5-a]pyridine maleate;
2-(4-(4-ethylpiperazin-1-yl)butoxy)-4,5,6,7-tetrahydropyrazolo[1,5-a]pyridine maleate;
2-(3-(piperidin-1-yl)propoxy)-4,5,6,7-tetrahydropyrazolo[1,5-a]pyridine maleate;
2-(3-(4-cyclohexylpiperazin-1-yl)propoxy)-4,5,6,7-tetrahydropyrazolo[1,5-a]pyridine maleate;
4-(3-(4,5,6,7-tetrahydropyrazolo[1,5-a]pyridin-2-yloxy)propyl)-1,4-oxazepane;
2-(4-(4-(tetrahydro-2H-pyran-4-yl)piperazin-1-yl)butyltetrahydro-2H-pyran-4-yl)piperazin-1-yl)butoxy)-4,5,6,7-tetrahydropyrazolo[1,5-a]pyridine maleate;
1-(4-(3-(4,5,6,7-tetrahydropyrazolo[1,5-a]pyridin-2-yloxy)propyl)piperazin-1-yl)ethanone maleate;
4-(2-(4,5,6,7-tetrahydropyrazolo[1,5-a]pyridin-2-yloxy)ethyl)thiomorpholine maleate;
2-(4-(4-tert-butylpiperidin-1-yl)butoxy)-3-chloro-4,5,6,7-tetrahydropyrazolo[1,5-a]pyridine maleate;
3-chloro-2-(4-chlorobutoxy)-4,5,6,7-tetrahydropyrazolo[1,5-a]pyridine from 3-chloro-4,5,6,7-tetrahydropyrazolo[1,5-a]pyridin-2-ol;
2-(4-(4-tert-butylpiperidin-1-yl)butoxy)-3-chloro-4,5,6,7-tetrahydropyrazolo[1,5-a]pyridine maleate;
N-benzyl-2-(3-iodopyrazolo[1,5-a]pyridin-2-yloxy)-N-methylethanamine oxalate;
N-benzyl-2-(3-iodo-4,5,6,7-tetrahydropyrazolo[1,5-a]pyridin-2-yloxy)-N-methylethanamine oxalate;
3-chloro-2-(4-(4-cyclohexylpiperazin-1-yl)butoxy)-4,5,6,7-tetrahydropyrazolo[1,5-a]pyridine.
or their pharmaceutically acceptable salts, stereoisomers, solvates or a prodrug thereof.

Any compound referred to herein is intended to represent such specific compound as well as certain variations or forms. In particular, compounds referred to herein may have asymmetric centers and therefore exist in different enantiomeric or diastereomeric forms. Thus, any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same as, or different to, the stereoisomerism of the other double bonds of the molecule. Furthermore, compounds referred to herein may exist as atropisomers. All the stereoisomers including enantiomers, diastereoisomers, geometric isomers and atropisomers of the compounds referred to herein, and mixtures thereof, are considered within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are amine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}C$- or $^{14}C$-enriched carbon, or the replacement of at least one nitrogen by $^{15}N$-enriched nitrogen are within the scope of this invention.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

A specific embodiment of the invention is that in which the pyrazolo[1,5-a]pyridine of the invention represent a compound with the general formula (Ia) or (Ib):

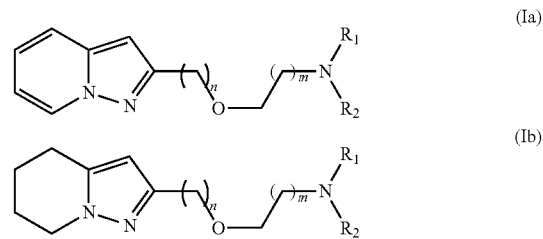

where the different substituent have the same meanings expressed before.

Also a specific embodiment is one in which the pyrazolo[1,5-a]pyridine of the invention are represented by the general formula (Ic) or (Id):

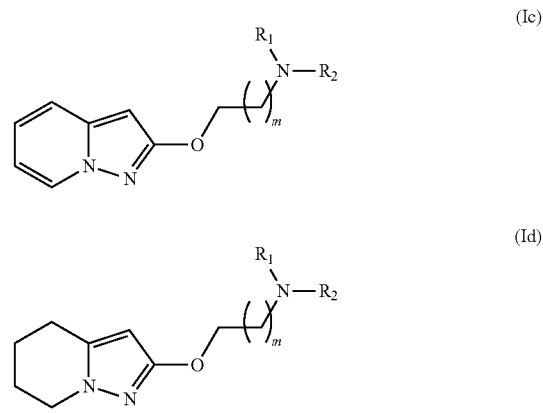

also where the different substituent have the same meanings expressed before.

Another specific embodiment is that in which the compounds of the invention have the general formula (Ie):

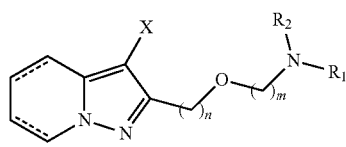
(Ie)

where the substituents are as expressed before and X represents a halogen such as F, Cl, Br or I.

In another aspect, the invention refers to the processes for obtaining the compounds of general formula (I). Several procedures have been developed for obtaining all the compound derivatives of the invention, herein the procedures will be explained below in methods A to C.

Method A

A process is described for the preparation of compounds of general formula (I) where n is different to 0 and $R_3$=H (see scheme I below). Method A is suited for obtaining compounds of general formula (Ia) and/or compounds of general formula (Ib):

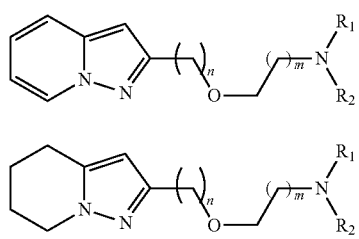
(Ia)
(Ib)

where $R_1$ and $R_2$, n and m have the meanings as defined in general formula (I).

Compounds of formula (Ia) can be prepared by two different processes. In a first process they are prepared from compounds of formula (IIa):

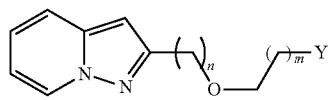
(IIa)

where Y is a suitable leaving group such as a halogen, by reaction with an amine of formula (III):

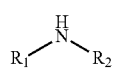
(III)

The reaction can be carried out in an organic solvent such as dimethylformamide (DMF) in the presence of an inorganic or an organic base, preferably $K_2CO_3$. An activating agent as NaI can be used.

A second process for the preparation of compounds of formula (Ia) comprises the reaction between a compound of formula (IVa):

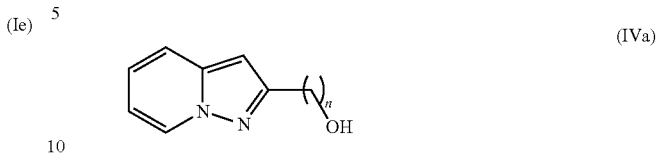
(IVa)

and a compound of formula (V):

(V)

where X is a suitable leaving group such as a halogen. This reaction can be carried out in an organic solvent such as dimethylformamide (DMF) or MeOH in the presence of a base such as NaH or potassium methoxide. An activating agent as NaI can be used. Compounds of formula (IIa) are obtained from (IVa) by reaction with compounds of formula (VI):

(VI)

where Y is a suitable leaving group such as a halogen. This reaction can be carried out in an aprotic solvent such as dimethylformamide (DMF) in the presence of an inorganic base such as NaH or $K_2CO_3$ or can be carried out under phase transfer conditions using a suitable catalyst such as tetra-N-butylammonium bromide or sulphate in a mixture of basic aqueous and organic phases. NaOH is the preferred inorganic base and toluene the preferred aprotic organic solvent.

Compounds of formula (IVa) are obtained by reduction of compounds of formula (VIIa):

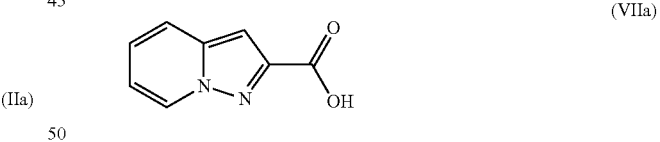
(VIIa)

Reduction of compounds of formula (VIIa) can be carried out with a suitable reducing agent as $BH_3 \cdot Me_2S$ in the presence of an anhydrous organic aprotic solvent as THF or toluene.

Compounds (III), (V), (VI) and (VIIa) are commercially available or can be obtained by conventional methods.

Compounds of formula (Ib) can be prepared as compounds of formula (Ia) by two different processes which are analogous to those for preparing compounds of general formula (Ia). In a first process they are prepared from compounds of formula (IIb):

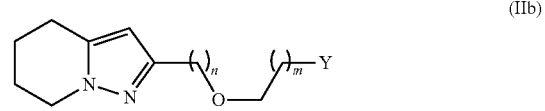
(IIb)

by reaction with an amine of formula (III) as described above. The reaction can be carried out in water or in an organic solvent, such as dimethylformamide (DMF) in the presence of an inorganic or an organic base, preferably K$_2$CO$_3$. An activating agent as NaI can also be used.

A second process for the preparation of compounds of formula (Ib) comprises the reaction between a compound of formula (IVb):

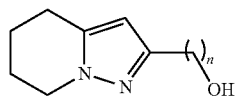

(IVb)

and a compound of formula (V) described above. This reaction can be carried out in an organic solvent such as dimethylformamide (DMF) or MeOH in the presence of a base such as NaH, K$_2$CO$_3$ or potassium methoxide. An activating agent as NaI can be used.

Compounds of formula (IIb) are obtained from (IVb) by reaction with compounds of formula (VI) described above. This reaction can be carried out in an aprotic solvent such as dimethylformamide (DMF) in the presence of an inorganic base such as NaH or K$_2$CO$_3$ or can be carried out under phase transfer conditions using a suitable catalyst such as tetra-N-butylammonium bromide or sulphate in a mixture of basic aqueous and organic phases. NaOH is the preferred inorganic base and toluene the preferred aprotic organic solvent.

Compounds of formula (IVb) are obtained by reduction of compounds of formula (VIIb):

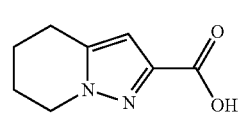

(VIIb)

In turn, compounds of formula (VIIb) are prepared by reduction of compounds of formula (VIIa). Reduction of compounds of formula (VIIa) is carried out preferably by hydrogenation under hydrogen atmosphere and metal catalysis, preferably by use of palladium over charcoal, in the presence of an organic solvent as DMF or ethyl alcohol or in a mixture of solvent and acid such as acetic acid or preferably in acetic acid as solvent.

In the following scheme, the synthetic route for preparation of compounds of general formula (Ia) and (Ib) is represented:

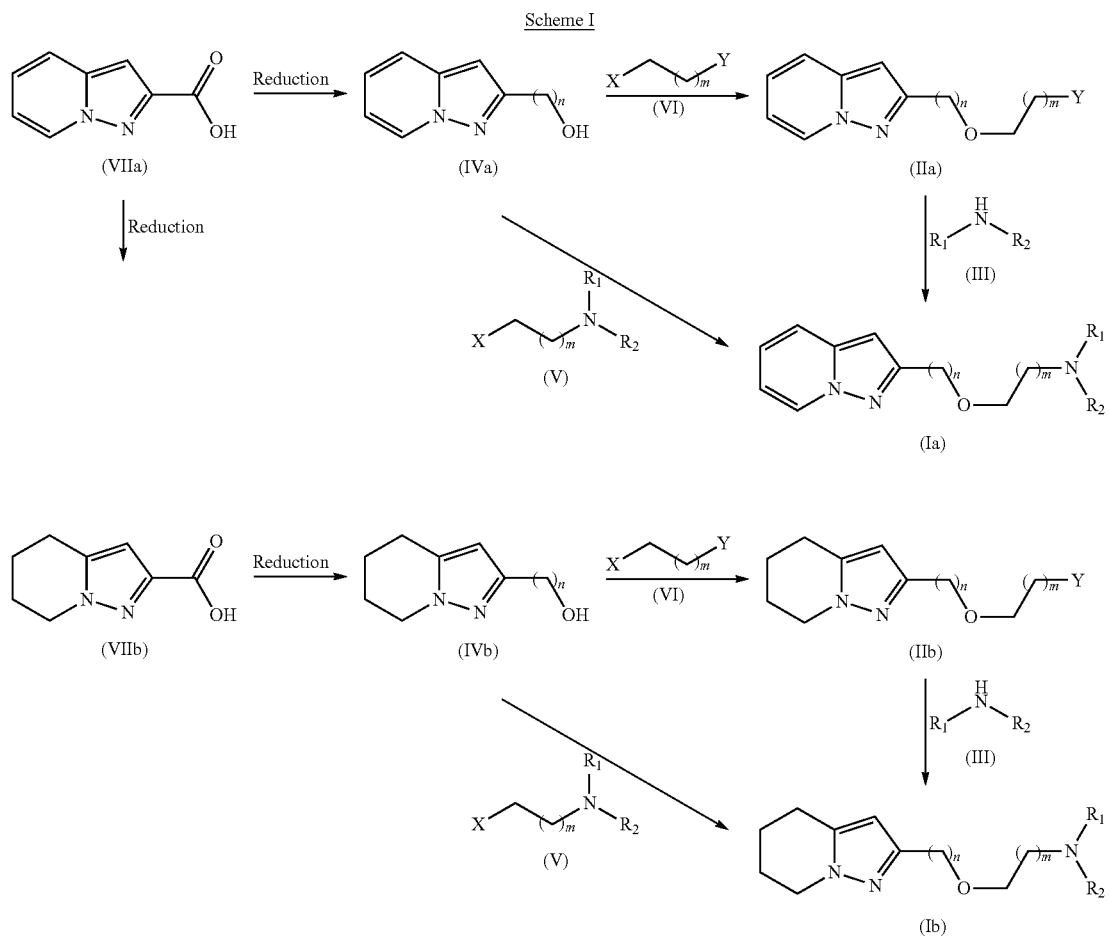

Scheme I

Method B

Method B represents the process for the preparation of compounds of general formula (I) where n is 0 and $R_3$ is hydrogen (scheme II), resulting on compounds of general formulas (Ic) and (Id):

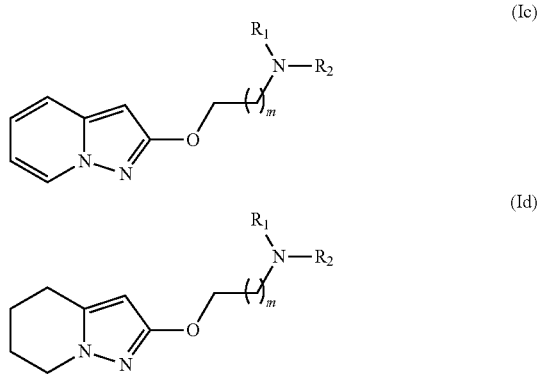

where $R_1$ and $R_2$ and have the meanings as in general formula (I).

Compounds of formula (Ic) can be prepared by two different processes. In a first process they are prepared from compounds of formula (IIc):

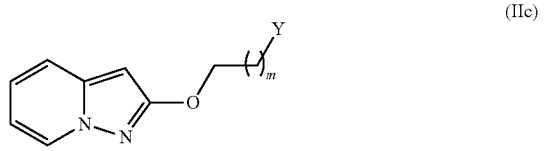

by reaction with an amine of formula (III) described in method A. The reaction can be carried out in water or in an organic solvent such as dimethylformamide (DMF) in the presence of an inorganic base, preferably $K_2CO_3$. An activating agent as NaI can be used.

A second process for the preparation of compounds of formula (Ic) comprises the reaction between a compound of formula (IVc):

and a compound of formula (V) described above in method A. This reaction can be carried out in an organic solvent such as dimethylformamide (DMF) or MeOH in the presence of a base such as NaH, $K_2CO_3$ or potassium methoxide. An activating agent as NaI can be used.

Compounds of formula (IIc) are obtained from (IVc) described above, by reaction with compounds of formula (VI) as described before where Y is a suitable leaving group such as a halogen. This reaction can be carried out in an aprotic solvent such as dimethylformamide (DMF) in the presence of an inorganic base such as NaH or $K_2CO_3$ or can be carried out under phase transfer conditions using a suitable catalyst such as tetra-N-butylammonium bromide or sulphate in a mixture of basic aqueous and organic phases. NaOH is the preferred inorganic base and toluene the preferred aprotic organic solvent.

Compounds of formula (IVc) are commercially available or can be prepared by known methods [*Bull. Soc. Jpn.* 49, 1976, 1980-1984].

Compounds of formula (Id) can analogously be prepared by two different processes. In a first process they are prepared from compounds of formula (IId):

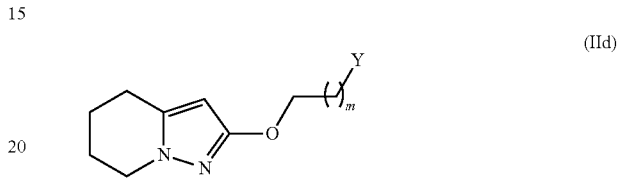

by reaction with an amine of formula (III) described above. The reaction can be carried out in water or in an organic solvent such as dimethylformamide (DMF) in the presence of an inorganic base, preferably $K_2CO_3$. An activating agent as NaI can be used.

A second process for the preparation of compounds of formula (Id) comprises the reaction between a compound of formula (IVd):

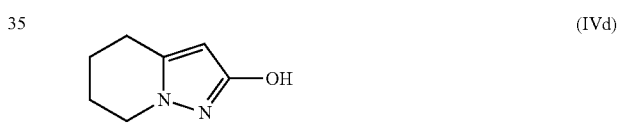

and a compound of formula (V) described above. This reaction can be carried out in an organic solvent such as dimethylformamide (DMF) or MeOH in the presence of a base such as NaH, $K_2CO_3$ or potassium methoxide. An activating agent as NaI can be used.

Compounds of formula (IId) are obtained from compounds of formula (IVd) by reaction with compounds of formula (VI), described above. This reaction can be carried out in an aprotic solvent such as dimethylformamide (DMF) in the presence of an inorganic base such as NaH or $K_2CO_3$ or can be carried out under phase transfer conditions using a suitable catalyst such as tetra-N-butylammonium bromide or sulphate in a mixture of basic aqueous and organic phases. NaOH is the preferred inorganic base and toluene the preferred aprotic organic solvent.

Compounds of formula (IVd) are prepared by reduction of compounds of formula (IVc), described above. Reduction of compounds of formula (IVc) is carried out preferably by hydrogenation under hydrogen atmosphere and metal catalysis, preferably by use of palladium over charcoal in the presence of an organic solvent as DMF or ethyl alcohol or in a mixture of solvent and acid such as acetic acid.

In the following scheme, the synthetic route for preparation of compounds of general formula (Ic) and (Id) is represented:

Scheme II
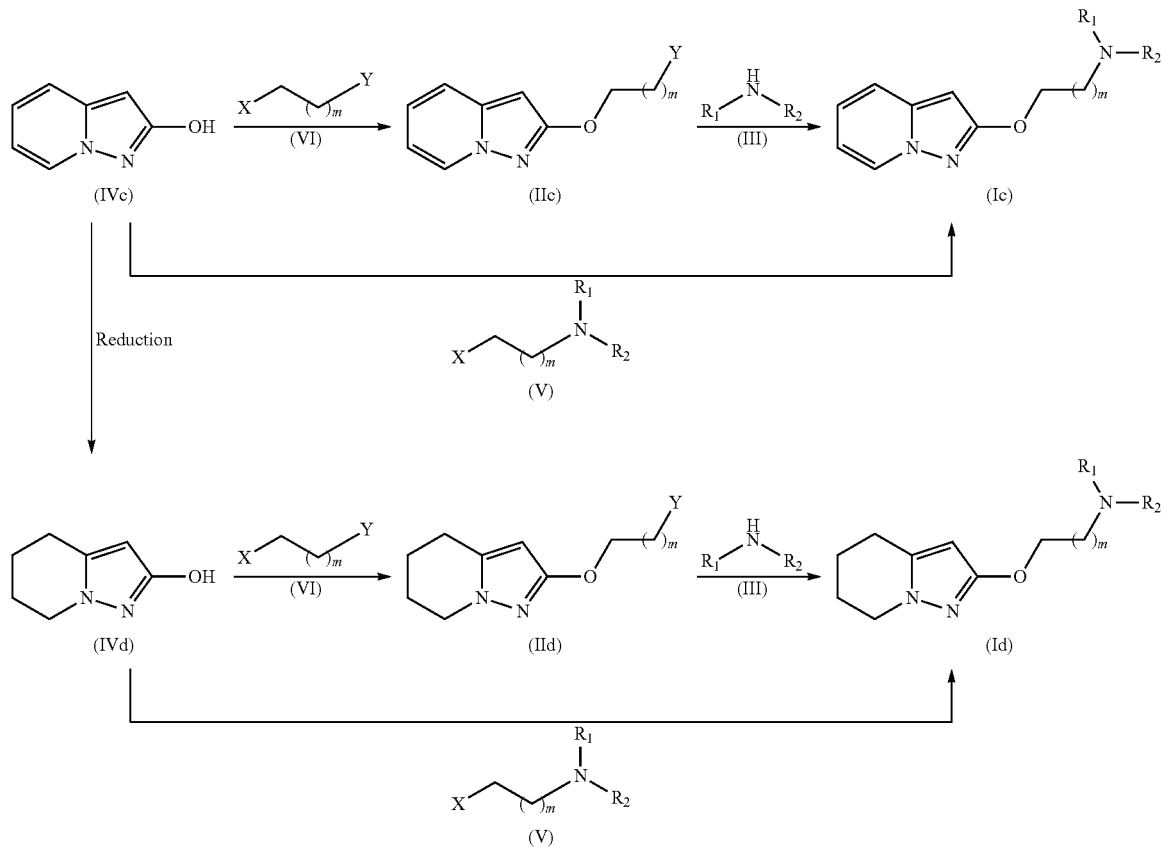
Method C
Compounds of formula (I) where $R_3$ is halogen, can be prepared either from its respective compounds of formula (Ia), (Ib), (Ic) or (Id) (where $R_3$=H) by direct halogenation with $X_2$ or halosuccinimide (NXS) or, for instance, following scheme III.
Scheme III
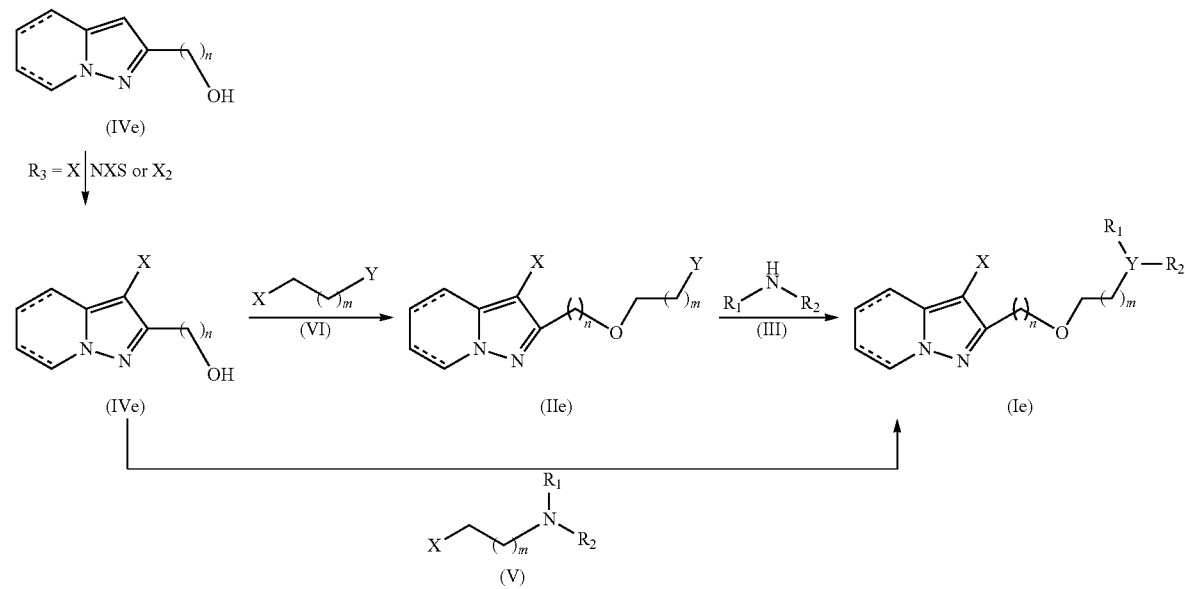

An additional aspect of the invention relates to the therapeutic use of the compounds of general formula (I). As mentioned above, compounds of general formula (I) show a strong affinity to sigma receptors and can behave as agonists, antagonists, inverse agonists, partial antagonists or partial agonists thereof. Therefore, compounds of general formula (I) are useful as medicaments.

They are suitable for the treatment and the prophylaxis of disorders and diseases mediated by sigma receptors, especially, sigma-1 receptors. In this sense, compounds of formula (I) are very good anxiolitic and immunosuppressant and are very useful in the treatment and prophylaxis of diarrhoea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases.

The compounds of formula (I) are especially suited for the treatment of pain, especially neuropathic pain, inflammatory pain or other pain conditions involving allodynia and/or hyperalgesia. PAIN is defined by the International Association for the Study of Pain (IASP) as "an unpleasant sensory and emotional experience associated with actual or potential tissue damage, or described in terms of such damage (IASP, Classification of chronic pain, 2nd Edition, IASP Press (2002), 210). Even though pain is always subjective its causes or syndromes can be classified.

In a preferred embodiment compounds of the invention are used for the treatment and prophylaxis of allodynia and more specifically mechanical or thermal allodynia.

In another preferred embodiment compounds of the invention are used for the treatment and prophylaxis of hyperalgesia.

In yet another preferred embodiment compounds of the invention are used for the treatment and prophylaxis of neuropathic pain and more specifically for the treatment and prophylaxis of hyperpathia.

A related aspect of the invention refers to the use of compounds of formula (I) for the manufacture of a medicament for the treatment of disorders and diseases mediated by sigma receptors, as explained before.

Another aspect of the invention is a pharmaceutical composition which comprises at least a compound of general formula (I) or a pharmaceutically acceptable salt, prodrug, isomer or solvate thereof, and at least a pharmaceutically acceptable carrier, additive, adjuvant or vehicle.

The pharmaceutical composition of the invention can be formulated as a medicament in different pharmaceutical forms comprising at least a compound binding to the sigma receptor and optionally at least one further active substance and/or optionally at least one auxiliary substance.

The auxiliary substances or additives can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously.

Preferably, the composition is suitable for oral or parenteral administration, more preferably for oral, intravenous, intraperitoneal, intramuscular, subcutaneous, intrathekal, rectal, transdermal, transmucosal or nasal administration.

The composition of the invention can be formulated for oral administration in any form preferably selected from the group consisting of tablets, drageés, capsules, pills, chewing gums, powders, drops, gels, juices, syrups, solutions and suspensions.

The composition of the present invention for oral administration may also be in the form of multiparticulates, preferably microparticles, microtablets, pellets or granules, optionally compressed into a tablet, filled into a capsule or suspended in a suitable liquid. Suitable liquids are known to those skilled in the art.

Suitable preparations for parenteral applications are solutions, suspensions, reconstitutable dry preparations or sprays.

The compounds of the invention can be formulated as deposits in dissolved form or in patches, for percutaneous application.

Skin applications include ointments, gels, creams, lotions, suspensions or emulsions.

The preferred form of rectal application is by means of suppositories.

The respective medicament may—depending on its route of administration—also contain one or more auxiliary substances known to those skilled in the art. The medicament according to the present invention may be produced according to standard procedures known to those skilled in the art.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

Described below are a number of examples by way of illustration of the invention and do not limit it in anyway.

Synthesis of Compounds of General Formula (Ia)

Example 1

Synthesis of 2-((4-(4-tert-butylpiperidin-1-yl)butoxy)methyl)pyrazolo[1,5-a]pyridine maleate 1a. Synthesis of pyrazolo[1,5-a]pyridin-2-ylmethanol

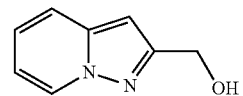 [SMILES: OCc1cc2ccccn2n1]

To a stirred solution of pyrazolo[1,5-a]pyridine-2-carboxylic acid (2.01 g, 12.4 mmol) in 65 mL of dry tetrahydrofuran (THF) cooled at 0° C., under nitrogen, were slowly added 31 mL (62.1 mmol) of a 2 M solution of borane dimethyl sulfide in toluene. After 30 min. at room temperature, the solution was heated at 65° C. for 5 h, and then cooled to 0° C. to add 15 mL of water. After addition of 8 mL of 6N solution of HCl, the mixture was refluxed for 2 h. Finally, the organic solvent was removed under reduced pressure, 40 mL of methanol were added and concentrated. The residue was solved in ethyl acetate, and washed with aqueous NaOH 10% solution and water. The organic layers were dried ($Na_2SO_4$) and concentrated to afford 1.42 g (77%) of pyrazolo[1,5-a]pyridin-2-ylmethanol as a colorless oil.

1b. Synthesis of 2-((4-chlorobutoxy)methyl)pyrazolo[1,5-a]pyridine

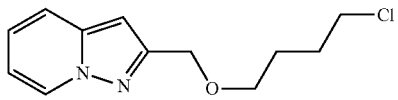 [SMILES: ClCCCCOCc1cc2ccccn2n1]

To a stirred solution of pyrazolo[1,5-a]pyridin-2-ylmethanol (0.31 g, 2 mmol) in 12 mL of dry THF, under nitrogen, were added 0.26 g (6.3 mmol) of NaH as 60% suspension in mineral oil. The mixture was stirred for 7 h at room temperature and then, a solution of 1-bromo-4-chlorobutane (0.36 mL, 3 mmol) in 2 mL of dry THF was added. After 18 h at 50 PC, the reaction mixture was allowed to cool to room temperature, ice was added, concentrated, and extracted with diethyl ether. The organic layers were washed with water, dried over $Na_2SO_4$ and concentrated under vacuum to afford an oil that was purified by flash chromatography with a petroleum ether/EtOAc mixture gradient to afford 0.17 g (33%) of 2-((4-chlorobutoxy)methyl)pyrazolo[1,5-a]pyridine as a colorless oil.

1c. Synthesis of 2-((4-(4-tert-butylpiperidin-1-yl)butoxy)methyl)pyrazolo[1,5-a]pyridine maleate (Example 1)

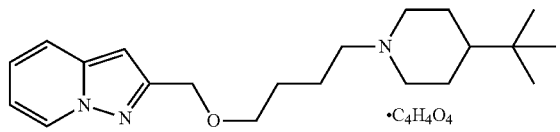

To a stirred solution of 2-((4-chlorobutoxy)methyl)pyrazolo[1,5-a]pyridine (50 mg, 0.21 mmol) in 2 mL of DMF, $K_2CO_3$ (87 mg, 0.63 mmol), 4-(tert-butyl)piperidine hydrochloride (56 mg, 0.31 mmol) and NaI (catalytic amount) were added. The reaction mixture was heated to 90° C. under nitrogen for 18 h, allowed to cool to room temperature and evaporated to dryness. Water and ethyl acetate were added and the organic layer was separated, washed with water, dried over $Na_2SO_4$ and concentrated under vacuum to afford 66 mg of brown oil that was poured into dichloromethane, stirred for 10 min. with $SiO_2$ and active charcoal, and then filtered and concentrated under vacuum to afford 60 mg (92%) of yellow oil. The maleate salt was prepared following this procedure: to an ice-cooled stirred solution of 2-((4-(4-tert-butylpiperidin-1-yl)butoxy)methyl)pyrazolo[1,5-a]pyridine (60 mg) in 2 mL of anhydrous isopropyl alcohol (IPA), 20 mg of maleic acid in 2 mL IPA were added dropwise. After stirring for 15 min at 0° C., diethyl ether was added and the solution was concentrated under vacuum to afford 38 mg of yellow solid on standing.

$^1$H NMR (CDCl$_3$) δ ppm: 8.40 (d, J=7.1 Hz, 1H), 7.51 (d, J=8.9 Hz, 1H), 7.18-7.04 (m, 1H), 6.74 (td, J=6.9, 1.3 Hz, 1H), 6.49 (s, 1H), 6.27 (s, 2H), 4.69 (s, 2H), 3.69-3.50 (m, 4H), 3.05-2.89 (m, 2H), 2.58-2.42 (m, 2H), 1.76 (ddd, J=19.7, 19.3, 10.6 Hz, 8H), 1.33-1.02 (m, 1H), 0.87 (s, 9H).

Example 1 can be, alternatively, obtained according to the procedure for example 2 from compound pyrazolo[1,5-a]pyridin-2-ylmethanol (compound IVa) above disclosed.

Example 2

Synthesis of 2-((2-(azepan-1-yl)ethoxy)methyl)pyrazolo[1,5-a]pyridine maleate

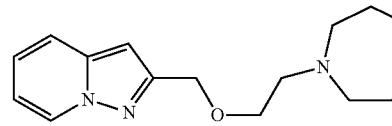

0.12 g (3 mmol) of a 60% NaH suspension in mineral oil were added under nitrogen to a solution of pyrazolo[1,5-a]pyridin-2-ylmethanol (100 mg, 0.67 mmol) in 5 mL of dry THF. The mixture was stirred for 5 h at room temperature, and after this time, was added 1-(2-chloroethyl)azepane hydrochloride (201 mg, 1.01 mmol) suspended in 8 mL of THF with 200 µl of triethylamine (TEA). The mixture was heated at 55° C. for 18 h, allowed to cool to room temperature, quenched with water and extracted with EtOAc, and washed with water. The organic layers were dried over $Na_2SO_4$ and concentrated under vacuum to afford 0.22 g (65%) of brown oil. Maleate salt was obtained following the same procedure as for example 1.

$^1$H NMR (CDCl$_3$) δ ppm: 8.42 (d, J=6.8 Hz, 1H), 7.52 (d, J=8.8 Hz, 1H), 7.20-7.06 (m, 1H), 6.78 (t, J=6.9 Hz, 1H), 6.49 (s, 1H), 6.30 (s, 2H), 4.74 (s, 2H), 4.08-3.89 (m, 2H), 3.70-3.51 (m, 2H), 3.36-3.25 (m, 2H), 3.19-2.99 (m, 2H), 2.15-1.92 (m, 2H), 1.92-1.72 (m, 4H), 1.72-1.54 (m, 2H).

Example 2 can be, alternatively, obtained according to the procedure described for example 1 from 2-((2-chloroethoxy)methyl)pyrazolo[1,5-a]pyridine (compound of formula IIa).

Examples 3 to 11 were prepared according to the procedures described in Examples 1 and/or 2

| Ex | Structure | Name | NMR |
|---|---|---|---|
| 3 | 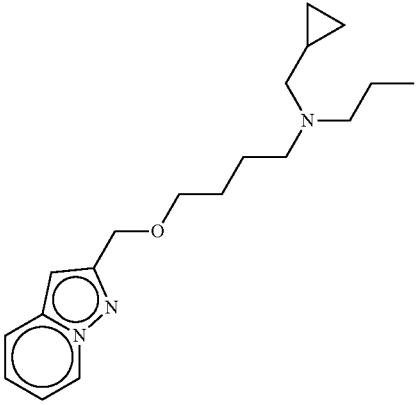 •C₄H₄O₄ | N-(cyclopropyl-methyl)-N-propyl-4-(pyrazolo[1,5-a]pyridin-2-ylmethylpyrazolo[1,5-a]pyridin-2-ylmethoxy)butan-1-amine maleate | $^1$H NMR (CDCl$_3$) δ: .40 (d, J = 7.0 Hz, 1H), 7.50 (d, J = 8.9 Hz, 1H), 7.15-7.03 (m, 1H), 6.74 (t, J = 6.9 Hz, 1H), 6.49 (s, 1H), 6.26 (s, 2H), 4.70 (s, 2H), 3.61 (t, J = 5.7 Hz, 2H), 3.23-3.10 (m, 2H), 3.10-2.97 (m, 2H), 2.93 (d, J = 7.2 Hz, 2H), 1.94-1.76 (m, 2H), 1.70 (dd, J = 13.1, 6.1 Hz, 4H), 1.07-0.99 (m, 1H), 0.97 (t, J = 7.4 Hz, 3H), 0.80-0.63 (m, 2H), 0.44-0.25 (m, 2H) |
| 4 | 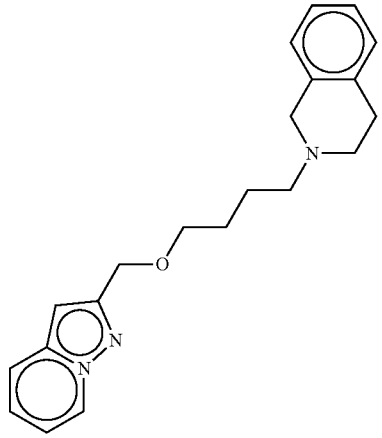 •C₄H₄O₄ | 2-(4-(pyrazolo[1,5-a]pyridin-2-ylmethylpyrazolo[1,5-a]pyridin-2-ylmethoxy)butyl)-1,2,3,4-tetrahydroiso-quinoline maleate | $^1$H NMR (CDCl$_3$) δ ppm: 8.39 (dd, J = 7.0, 0.9 Hz, 1H), 7.50 (d, J = 8.9 Hz, 1H), 7.31-7.27 (m, 1H), 7.26-7.22 (m, 1H), 7.17 (d, J = 8.5 Hz, 1H), 7.13-7.05 (m, 2H), 6.74 (td, J = 6.8, 1.1 Hz, 1H), 6.47 (s, 1H), 6.22 (s, 2H), 4.69 (s, 2H), 4.63-3.94 (m, 2H), 3.61 (t, J = 5.8 Hz, 2H), 3.72-2.79 (m, 2H), 3.26-2.96 (m, 4H), 2.20-1.86 (m, 2H), 1.86-1.56 (m, 2H). |
| 5 | 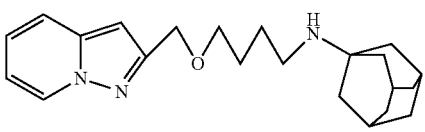 •C₄H₄O₄ | N-adamantyl-4-(pyrazolo[1,5-a]pyridin-2-ylmethyl pyrazolo[1,5-a]pyridin-2-ylmethoxy)butan-1-amine maleate | $^1$H NMR (CDCl$_3$) δ ppm: 8.73- 8.47 (m, 2H), 8.55 (d, J = 7.1 Hz, 1H), 7.53 (d, J = 8.9 Hz, 1H), 7.21-7.04 (m, 1H), 6.80 (td, J = 6.9, 1.2 Hz, 1H), 6.55 (s, 1H), 6.35 (s, 2H), 4.78 (s, 2H), 3.75-3.64 (m, 2H), 3.05-2.90 (m, 2H), 2.13-1.90 (m, 6H), 1.89-1.76 (m, 3H), 1.77-1.67 (m, 6H), 1.64-1.50 (m, 2H), 1.50-1.34 (m, 2H). |

| Ex | Structure | Name | NMR |
|---|---|---|---|
| 6 | 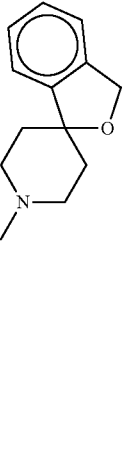•C₄H₄O₄ | 1'-(4-(pyrazolo [1,5-a]pyridin-2-ylmethylpyrazolo [1,5-a]pyridin-2-ylmethoxy) butyl)-3H-spiro [isobenzofuran-1,4'-piperidine] maleate | $^1$H NMR (CDCl$_3$) δ ppm: 8.42 (d, J = 7.0 Hz, 1H), 7.51 (d, J = 8.9 Hz, 1H), 7.36-7.28 (m, 2H), 7.24-7.16 (m, 2H), 7.13-7.02 (m, 1H), 6.74 (td, J = 6.9, 1.2 Hz, 1H), 6.50 (s, 1H), 6.32 (s, 2H), 5.08 (s, 2H), 4.71 (s, 2H), 3.61 (t, J = 5.8 Hz, 2H), 3.56-3.43 (m, 2H), 3.26-2.97 (m, 4H), 2.48 (td, J = 14.1, 4.2 Hz, 2H), 2.06-1.79 (m, 4H), 1.79-1.65 (m, 2H). |
| 7 | •C₄H₄O₄ | 2-((2-(pyrrolidin-1-yl)ethoxy) methyl) pyrazolo[1,5-a] pyridine maleate | $^1$H NMR (CDCl$_3$) δ ppm: 8.45 (d, J = 6.2 Hz, 1H), 7.52 (d, J = 8.2 Hz, 1H), 7.19-7.08 (m, 1H), 6.79 (t, J = 6.3 Hz, 1H), 6.51 (s, 1H), 6.34 (s, 2H), 4.76 (s, 2H), 4.07-3.76 (m, 4H), 3.39-3.21 (m, 2H), 3.11-2.73 (m, 2H), 2.27-1.79 (m, 4H). |
| 8 | 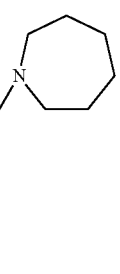•C₄H₄O₄ | 2-((4-(azepan-1-yl)butoxy) methyl)pyrazolo [1,5-a]pyridine maleate | $^1$H NMR (CDCl$_3$) δ ppm: 8.41 (d, J = 7.0 Hz, 1H), 7.51 (d, J = 8.9 Hz, 1H), 7.17-7.05 (m, 1H), 6.74 (td, J = 6.9, 1.3 Hz, 1H), 6.49 (s, 1H), 6.28 (s, 2H), 4.69 (s, 2H), 3.59 (t, J = 5.8 Hz, 2H), 3.56-3.44 (m, 2H), 3.13-2.98 (m, 2H), 2.99-2.80 (m, 2H), 2.10-1.51 (m, 12H). |

-continued

| Ex | Structure | Name | NMR |
|---|---|---|---|
| 9 |  ·C₄H₄O₄ | 2-((4-(4-methyl-piperazin-1-yl)butoxy)methyl)pyrazolo[1,5-a]pyridine maleate | $^1$H NMR (CDCl$_3$) δ ppm: 8.40 (d, J = 7.0 Hz, 1H), 7.50 (d, J = 8.9 Hz, 1H), 7.14-7.04 (m, 1H), 6.73 (t, J = 6.7 Hz, 1H), 6.49 (s, 1H), 6.28 (s, 2H), 4.69 (s, 2H), 3.57 (t, J = 5.7 Hz, 2H), 3.36-2.97 (m, 2H), 2.97-2.42 (m, 11H), 1.85-1.52 (m, 4H). |
| 10 | 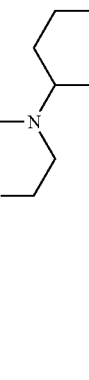 ·C₄H₄O₄ | 2-((4-(4-cyclo-hexylpiperazin-1-yl)butoxy)methyl)pyrazolo[1,5-a]pyridine maleate | $^1$H NMR (CDCl$_3$) δ ppm: 8.41 (d, J = 7.0 Hz, 1H), 7.50 (d, J = 8.8 Hz, 1H), 7.17-7.05 (m, 1H), 6.73 (t, J = 6.5 Hz, 1H), 6.49 (s, 1H), 6.27 (s, 2H), 4.69 (s, 2H), 3.57 (t, J = 5.5 Hz, 2H), 3.47-2.83 (m, 9H), 2.83-2.57 (m, 2H), 2.16-2.01 (m, 2H), 2.02-1.80 (m, 2H), 1.78-1.58 (m, 4H), 1.54-1.04 (m, 6H). |
| 11 | 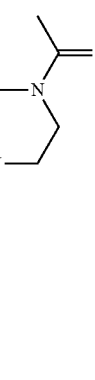 | 1-(4-(4-(pyrazolo[1,5-a]pyridin-2-ylmethylpyrazolo[1,5-a]pyridin-2-ylmethoxy)butyl)piperazin-1-yl)ethanone | $^1$H NMR (CDCl$_3$) δ ppm: 8.40 (d, J = 7.0 Hz, 1H), 7.48 (d, J = 8.9 Hz, 1H), 7.09 (ddd, J = 8.8, 6.7, 1.0 Hz, 1H), 6.72 (td, J = 6.9, 1.3 Hz, 1H), 6.50 (s, 1H), 4.71 (s, 2H), 3.57 (t, J = 6.1 Hz, 2H), 3.74-3.40 (m, 4H), 2.57-2.31 (m, 6H), 2.08 (s, 3H), 1.72-1.59 (m, 4H). |

Synthesis of Compounds of General Formula (Ic)

Example 12

Synthesis of 1-benzyl-N-methyl-N-(4-(pyrazolo[1,5-a]pyridin-2-yloxy)butyl) piperidin-4-amine difumarate

12a. Synthesis of 2-(4-chlorobutoxy)pyrazolo[1,5-a]pyridine

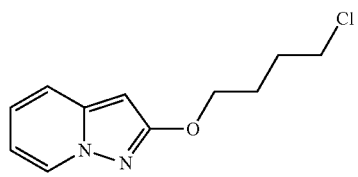 [SMILES: ClCCCCOc1cc2ccccn2n1]

A solution of pyrazolo[1,5-a]pyridin-2-ol (776 mg, 5.78 mmol), $K_2CO_3$ (2.4 g, 17.3 mmol), 1-bromo-4-chlorobutane (1.35 mL, 11.6 mmol) and sodium iodide (catalytic amount) in 20 mL of DMF was stirred for 18 h at room temperature. The resulting mixture was filtered, the solid washed with DMF and the organic filtrate concentrated. The residue was poured into diethyl ether and the generated precipitate filtered and discarded. The organic filtrate was washed with water and the organic layer dried ($Na_2SO_4$) and concentrated under vacuum to afford 1.35 g (quantitative) of brown oil.

12b. Synthesis of 1-benzyl-N-methyl-N-(4-(pyrazolo[1,5-a]pyridin-2-yloxy)butyl)piperidin-4-amine difumarate (Example 12)

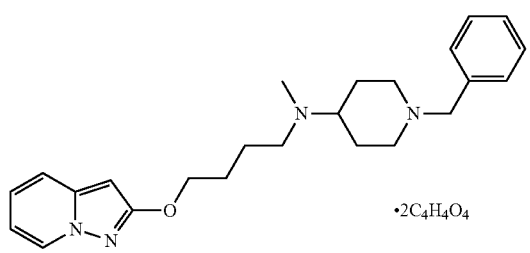 [SMILES: CN(CCCCOc1cc2ccccn2n1)C1CCN(Cc2ccccc2)CC1]

A solution of 2-(4-chlorobutoxy)pyrazolo[1,5-a]pyridine (80 mg, 0.356 mmol), $K_2CO_3$ (148 mg, 1.068 mmol), 1-benzyl-N-methyl-piperidine (116 mg, 0.570 mmol) and NaI (catalytic amount) in 5 ml of anhydrous DMF was heated to 90° C. under nitrogen for 18 h. The reaction mixture was allowed to cool to room temperature and evaporated to dryness. A mixture of water and ice was added and extracted with EtOAc. The organic layers were dried and evaporated under vacuum to give 177 mg of yellow oil that was further purified by flash chromatography on silica gel with EtOAc/MeOH/$NH_4OH$ eluent to afford 67 mg (48%) of yellow oil. To a stirred solution of 1-benzyl-N-methyl-N-(4-(pyrazolo[1,5-a]pyridin-2-yloxy)butyl)piperidin-4-amine (70 mg, 0.178 mmol) in 4 mL ethyl alcohol at room temperature, 41 mg (0.357 mmol) fumaric acid in 7 ml ethyl alcohol were added dropwise. The precipitate was filtered and washed with ethyl alcohol and diethyl ether to afford 62 mg (56%) of cream coloured solid.

$^1$H NMR (DMSO) δ ppm: 8.43 (d, J=6.9 Hz, 1H), 7.43 (d, J=8.9 Hz, 1H), 7.37-7.20 (m, 5H), 7.20-7.06 (m, 1H), 6.71 (t, J=6.9 Hz, 1H), 6.58 (s, 4H), 5.95 (s, 1H), 4.20 (t, J=6.3 Hz, 2H), 3.46 (s, 2H), 2.94-2.79 (m, 2H), 2.75-2.60 (m, 3H), 2.35 (s, 3H), 1.95 (t, J=11.2 Hz, 2H), 1.82-1.66 (m, 4H), 1.66-1.39 (m, 4H).

Example 12 can be, alternatively, obtained according to the following procedure for example 13, from pyrazolo[1,5-a]pyridin-2-ol (compound of formula IVc).

Example 13

Synthesis of 4-(2-(pyrazolo[1,5-a]pyridin-2-yloxy)ethyl)morpholine

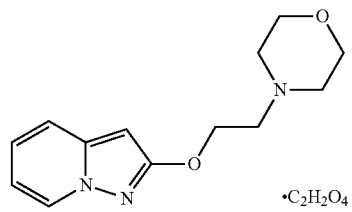 [SMILES: c1ccn2nc(OCCN3CCOCC3)cc2c1 ; "·C2H2O4"]

To a solution of pyrazolo[1,5-a]pyridin-2-ol (120 mg, 0.89 mmol) in 4 mL of anhydrous DMF, were added $K_2CO_3$ (270 mg, 1.95 mmol), 4-(2-chloroethyl)morpholine hydrochloride (183 mg, 0.98 mmol) and NaI (134 mg, 0.89 mmol) and the mixture heated to 80° C. for 18 h under nitrogen. The solvent was evaporated under reduced pressure and the residue poured into a mixture of EtOAc and water, to afford after drying and evaporation of organic layers, 112 mg of an oil that was purified by silica gel flash chromatography with EtOAc/MeOH (9:1) as eluent to afford 57 mg of 4-(2-(pyrazolo[1,5-a]pyridin-2-yloxy)ethyl)morpholine. 40 mg (0.43 mmol) of anhydrous oxalic acid in 0.5 mL of acetone were added to a solution of 98 mg of 4-(2-(pyrazolo[1,5-a]pyridin-2-yloxy)ethyl)morpholine base oil in 0.5 mL of acetone. The solid is filtered and washed with diethyl ether to give 133 mg (90%).

$^1$H NMR (DMSO) δ ppm: 8.46 (d, J=6.9 Hz, 1H), 7.46 (d, J=8.9 Hz, 1H), 7.26-7.09 (m, 1H), 6.74 (td, J=6.9, 1.4 Hz, 1H), 6.00 (s, 1H), 4.41 (t, J=5.3 Hz, 2H), 3.74-3.60 (m, 4H), 3.07 (t, J=5.2 Hz, 2H), 2.92-2.66 (m, 4H).

Example 13 can be, alternatively, obtained according to the procedure described for example 12 from 2-[(chloromethoxy)methyl]pyrazolo[1,5-a]pyridine (compound of formula IIc).

Examples 14 to 51 were prepared according to the procedures described in Example 12 and/or 13.

| Ex | Structure | Name | NMR |
|---|---|---|---|
| 14 | ·C₂H₂O₄ | 2-(2-piperidin-1-yl)ethoxy)pyrazolo[1,5-a]pyridine oxalate | ¹H NMR (DMSO) δ ppm: 8.48 (d, J = 6.9 Hz, 1H), 7.48 (d, J = 8.9 Hz, 1H), 7.33-7.11 (m, 1H), 6.76 (td, J = 6.9, 1.3 Hz, 1H), 6.04 (s, 1H), 4.65-4.42 (m, 2H), 3.52-3.31 (m, 2H), 3.31-2.99 (m, 4H), 1.83-1.59 (m, 4H), 1.59-1.38 (m, 2H). |
| 15 | ·C₂H₂O₄ | 2-(2-(pyrrolidin-1-yl)ethoxy)pyrazolo[1,5-a]pyridine oxalate | ¹H NMR (DMSO) δ ppm: 8.48 (d, J = 6.9 Hz, 1H), 7.49 (d, J = 8.9 Hz, 1H), 7.35-7.06 (m, 1H), 6.76 (td, J = 6.9, 0.9 Hz, 1H), 6.04 (s, 1H), 4.64-4.40 (m, 2H), 3.57-3.49 (m, 2H), 3.34-3.17 (m, 4H), 1.98-1.77 (m, 4H). |
| 16 | ·C₂H₂O₄ | N,N-diethyl-2-(pyrazolo[1,5-a]pyridin-2-yloxy)ethanamine oxalate | ¹H NMR (DMSO) δ ppm: 8.48 (d, J = 6.9 Hz, 1H), 7.49 (d, J = 8.9 Hz, 1H), 7.30-7.12 (m, 1H), 6.77 (td, J = 6.9, 1.3 Hz, 1H), 6.04 (s, 1H), 4.51 (t, J = 5.1 Hz, 2H), 3.52-3.39 (m, 2H), 3.14 (q, J = 7.1 Hz, 4H), 1.19 (t, J = 7.2 Hz, 6H). |
| 17 | ·C₂H₂O₄ | 4-(4-(pyrazolo[1,5-a]pyridin-2-yloxy)butyl)morpholine oxalate | ¹H NMR(DMSO) δ ppm: 8.44 (d, J = 6.9 Hz, 1H), 7.44 (d, J = 8.9 Hz, 1H), 7.24-7.07 (m, 1H), 6.72 (td, J = 6.9, 1.3 Hz, 1H), 5.96 (s, 1H), 4.21 (t, J = 5.8 Hz, 2H), 3.78-3.66 (m, 4H), 3.07-2.75 (m, 6H), 1.92-1.62 (m, 4H). |
| 18 | ·C₂H₂O₄ | 2-(4-(piperidin-1-yl)butoxy)pyrazolo[1,5-a]pyridine oxalate | ¹H NMR (CD₃OD) δ ppm: 8.27 (d, J = 7.0 Hz, 1H), 7.41 (d, J = 8.9 Hz, 1H), 7.23-7.06 (m, 1H), 6.73 (td, J = 6.9, 1.1 Hz, 1H), 5.94 (s, 1H), 4.29 (t, J = 5.5 Hz, 2H), 3.67-3.41 (m, 2H), 3.22-3.11 (m, 2H), 3.02-2.78 (m, 2H), 2.06-1.67 (m, 9H), 1.67-1.35 (m, 1H). |

| Ex | Structure | Name | NMR |
|---|---|---|---|
| 19 | •C₂H₂O₄ | N,N-diethyl-4-(pyrazolo[1,5-a]pyridin-2-yloxy)butan-1-amine oxalate | $^1$H NMR (CD$_3$OD) δ ppm: 8.27 (d, J = 7.0 Hz, 1H), 7.41 (d, J = 8.9 Hz, 1H), 7.16 (dd, J = 8.3, 7.5 Hz, 1H), 6.74 (t, J = 6.9 Hz, 1H), 5.94 (s, 1H), 4.30 (t, J = 4.9 Hz, 2H), 3.25 (q, J = 7.3 Hz, 4H), 2.01-1.80 (m, 4H), 1.32 (t, J = 7.3 Hz, 6H). |
| 20 | •C₂H₂O₄ | 2-(4-(pyrrolidin-1-yl)butoxy)pyrazolo[1,5-a]pyridine oxalate | $^1$H NMR (CD$_3$OD) δ ppm: 8.27 (d, J = 7.0 Hz, 1H), 7.41 (d, J = 8.9 Hz, 1H), 7.16 (ddd, J = 8.9, 6.9, 1.0 Hz, 1H), 6.73 (td, J = 6.9, 1.3 Hz, 1H), 5.94 (s, 1H), 4.28 (t, J = 5.4 Hz, 2H), 3.76-3.41 (m, 2H), 3.43-2.97 (m, 4H), 2.20-1.98 (m, 4H), 2.00-1.82 (m, 4H). |
| 21 | •C₂H₂O₄ | 2-(4-(4-phenylpiperidin-1-yl)butoxy)pyrazolo[1,5-a]pyridine oxalate | $^1$H NMR (dmso) δ ppm: 8.44 (d, J = 6.9 Hz, 1H), 7.45 (d, J = 8.9 Hz, 1H), 7.38-7.28 (m, 2H), 7.28-7.20 (m, 3H), 7.20-7.12 (m, 1H), 6.73 (td, J = 6.9, 1.4 Hz, 1H), 5.97 (s, 1H), 4.24 (t, J = 5.0 Hz, 2H), 3.57-3.43 (m, 2H), 3.14-2.87 (m, 4H), 2.84-2.70 (m, 1H), 2.09-1.65 (m, 8H). |
| 22 | •C₂H₂O₄ | N-benzyl-N-methyl-4-(pyrazolo[1,5-a]pyridin-2-yloxy)butan-1-amine oxalate | $^1$H NMR (DMSO) δ ppm: 8.44 (d, J = 6.9 Hz, 1H), 7.57-7.34 (m, 6H), 7.25-7.07 (m, 1H), 6.72 (td, J = 6.9, 1.4 Hz, 1H), 5.95 (s, 1H), 4.21 (t, J = 5.6 Hz, 2H), 4.10 (s, 2H), 3.02-2.86 (m, 2H), 2.60-2.52 (m, 3H), 1.88-1.70 (m, 4H). |

-continued

| Ex | Structure | Name | NMR |
|---|---|---|---|
| 23 | •C₂H₂O₄ | 2,(4-(4-phenoxypiperidin-1-yl)butoxy)pyrazolo[1,5-a]pyridine oxalate | ¹H NMR (DMSO) δ ppm: 8.44 (d, J = 6.9 Hz, 1H), 7.45 (d, J = 8.9 Hz, 1H), 7.34-7.23 (m, 2H), 7.21-7.11 (m, 1H), 7.03-6.90 (m, 3H), 6.72 (td, J = 6.8, 1.1 Hz, 1H), 5.97 (s, 1H), 4.67-4.57 (m, 1H), 4.23 (t, J = 5.2 Hz, 2H), 3.35-3.19 (m, 2H), 3.15-2.99 (m, 4H), 2.16-2.02 (m, 2H), 1.95-1.82 (m, 2H), 1.83-1.73 (m, 4H). |
| 24 | •C₂H₂O₄ | N-benzyl-N-methyl-2-(pyrazolo[1,5-a]pyridin-2-yloxy)ethanamine oxalate | ¹H NMR (DMSO) δ ppm: 8.46 (dd, J = 6.9, 0.8 Hz, 1H), 7.54-7.29 (m, 6H), 7.24-7.09 (m, 1H), 6.74 (td, J = 6.9, 1.4 Hz, 1H), 6.00 (s, 1H), 4.46 (t, J = 5.3 Hz, 2H), 4.01 (s, 2H), 3.17 (s, 2H), 2.55-2.52 (m, 3H). |
| 25 | •C₂H₂O₄ | 2-(4-(4-phenylpiperazin-1-yl)butoxy)pyrazolo[1,5-a]pyridine oxalate | ¹H NMR (DMSO) δ ppm: 8.44 (d, J = 6.8 Hz, 1H), 7.45 (d, J = 8.7 Hz, 1H), 7.24 (t, J = 7.6 Hz, 2H), 7.16 (t, J = 7.6 Hz, 1H), 6.97 (d, J = 7.7 Hz, 2H), 6.83 (t, J = 6.9 Hz, 1H), 6.72 (t, J = 6.7 Hz, 1H), 5.97 (s, 1H), 4.32-4.12 (m, 2H), 3.42-3.17 (m, 4H), 3.19-2.99 (m, 4H), 3.01-2.85 (m, 2H), 1.87-1.65 (m, 4H). |
| 26 | 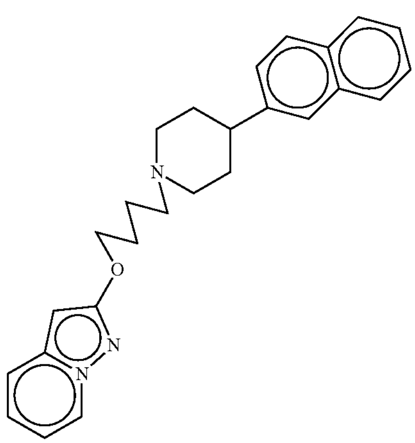 | 2-(4-(4-(naphthalen-2-yl)piperidin-1-yl)butoxy)pyrazolo[1,5-a]pyridine | ¹H NMR(CDCl₃) δ ppm: 8.22 (d, J = 6.9 Hz, 1H), 7.86-7.73 (m, 3H), 7.69-7.62 (m, 1H), 7.50-7.35 (m, 3H), 7.32-7.27 (m, 1H), 7.13-6.95 (m, 1H), 6.60 (td, J = 6.9, 1.3 Hz, 1H), 5.83 (s, 1H), 4.29 (t, J = 5.7 Hz, 2H), 3.46-3.27 (m, 1H), 2.85-2.69 (m, 2H), 2.54-2.16 (m, 4H), 2.07-1.86 (m, 7H), 1.81-1.67 (m, 2H). |

-continued

| Ex | Structure | Name | NMR |
|---|---|---|---|
| 27 | •C₂H₂O₄ | 1'-(4-(pyrazolo[1,5-a]pyridin-2-yloxy)butyl)-3H-spiro[isobenzofuran-1,4'-piperidine] oxalate | ¹H NMR (DMSO) δ ppm: 8.45 (d, J = 6.9 Hz, 1H), 7.45 (d, J = 8.9 Hz, 1H), 7.36-7.29 (m, 3H), 7.26-7.20 (m, 1H), 7.20-7.11 (m, 1H), 6.73 (td, J = 6.9, 1.4 Hz, 1H), 5.98 (s, 1H), 5.04 (s, 2H), 4.25 (t, J = 5.1 Hz, 2H), 3.51-3.34 (m, 2H), 3.15-2.98 (m, 4H), 2.24 -2.10 (m, 2H), 1.91-1.71 (m, 6H). |
| 28 | 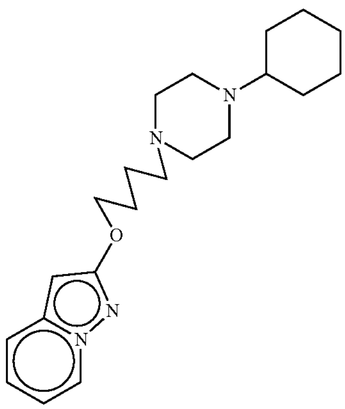 | 2-(4-(4-cyclohexylpiperazin-1-yl)butoxy)pyrazolo[1,5-a]pyridine | ¹H NMR (CDCl₃) δ ppm: 8.21 (d, J = 7.0 Hz, 1H), 7.28 (d, J = 11.0 Hz, 4H), 7.10-6.96 (m, 1H), 6.58 (t, J = 6.9 Hz, 1H), 5.81 (s, 1H), 4.25 (t, J = 6.4 Hz, 2H), 2.65-2.44 (m, 6H), 2.44-2.35 (m, 2H), 2.27-2.14 (m, 1H), 1.93-1.74 (m, 5H), 1.74-1.63 (m, 2H), 1.31-1.04 (m, 5H). |
| 29 | •2C₄H₄O₄ | 2-(4-(4-cyclohexylpiperazin-1-yl)butoxy)pyrazolo[1,5-a]pyridine dimaleate | ¹H NMR (CD₃OD) δ ppm: 8.26 (d, J = 6.9 Hz, 1H), 7.39 (d, J = 8.9 Hz, 1H), 7.22-7.05 (m, 1H), 6.80-6.63 (m, 1H), 6.28 (s, 4H), 5.92 (s, 1H), 4.26 (t, J = 6.0 Hz, 2H), 3.24-3.10 (m, 3H), 3.02-2.75 (m, 4H), 2.68 (t, J = 7.2 Hz, 2H), 2.11-1.97 (m, 2H), 1.94-1.82 (m, 4H), 1.81-1.60 (m, 3H), 1.48-1.25 (m, 4H), 1.26-1.07 (m, 1H). |
| 30 | •HCl | 2-(4-(4-tert-butylpiperidin-1-yl)butoxy)pyrazolo[1,5-a]pyridine hydrochloride | ¹H NMR (DMSO) δ ppm: 9.64-9.44 (m, 1H), 8.44 (d, J = 6.9 Hz, 1H), 7.45 (d, J = 8.8 Hz, 1H), 7.24-7.06 (m, 1H), 6.72 (t, J = 6.8 Hz, 1H), 5.96 (s, 1H), 4.23 (t, J = 5.5 Hz, 2H), 3.60-3.42 (m, 2H), 3.13-2.96 (m, 2H), 2.92-2.67 (m, 2H), 2.00-1.68 (m, 6H), 1.62-1.37 (m, 2H), 1.33-1.12 (m, 1H), 0.85 (s, 9H). |

-continued

| Ex | Structure | Name | NMR |
|---|---|---|---|
| 31 | 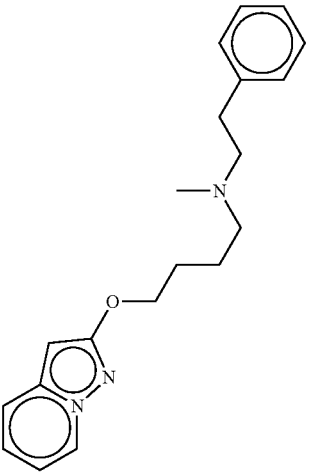 •HCl | N-methyl-N-phenethyl-4-(pyrazolo[1,5-a]pyridin-2-yloxy)butan-1-amine hydrochloride | $^1$H NMR (DMSO) δ ppm: 9.98-9.80 (m, 1H), 8.43 (d, J = 6.9 Hz, 1H), 7.45 (d, J = 8.8 Hz, 1H), 7.38-7.21 (m, 5H), 7.21-7.05 (m, 1H), 6.73 (t, J = 6.9 Hz, 1H), 5.97 (s, 1H), 4.24 (t, J = 5.6 Hz, 2H), 3.23-2.92 (m, 5H), 2.92-2.72 (m, 4H), 1.94-1.63 (m, 4H). |
| 32 | 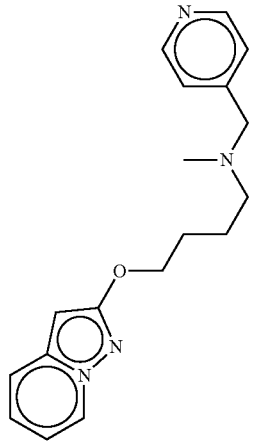 •2HCl | N-methyl-4-(pyrazolo[1,5-a]pyridin-2-yloxy)-N-(pyridin-4-ylmethyl)butan-1-amine dihydrochloride | $^1$H NMR (DMSO) δ ppm: 11.15-10.92 (m, 1H), 8.81 (d, J = 6.2 Hz, 2H), 8.44 (d, J = 6.9 Hz, 1H), 7.90 (d, J = 5.9 Hz, 2H), 7.45 (d, J = 8.9 Hz, 1H), 7.26-7.07 (m, 1H), 6.73 (td, J = 6.9, 1.4 Hz, 1H), 5.96 (s, 1H), 4.60-4.30 (m, 2H), 4.22 (t, J = 6.1 Hz, 2H), 3.24-3.01 (m, 2H), 2.69 (s, 3H), 2.01-1.84 (m, 2H), 1.84-1.68 (m, 2H). |
| 33 | 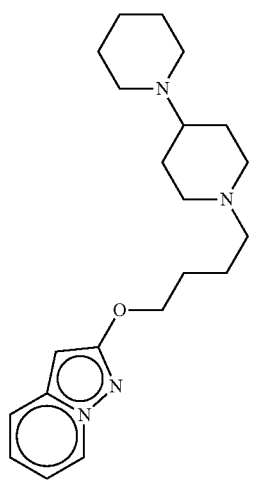 •2C$_4$H$_4$O$_4$ | 2-(4-(1,4'-bipiperidin-1'-yl)butoxy)pyrazolo[1,5-a]pyridine difumarate | $^1$H NMR (DMSO) δ ppm: 8.43 (d, J = 6.8 Hz, 1H), 7.44 (d, J = 8.9 Hz, 1H), 7.19-7.05 (m, 1H), 6.71 (t, J = 6.9 Hz, 1H), 6.56 (s, 4H), 5.95 (s, 1H), 4.19 (t, J = 6.2 Hz, 2H), 3.07-2.90 (m, 2H), 2.80-2.63 (m, 4H), 2.61-2.53 (m, 1H), 2.45-2.38 (m, 2H), 2.08-1.90 (m, 2H), 1.85-1.66 (m, 4H), 1.66-1.49 (m, 8H), 1.49-1.34 (m, 2H). |

| Ex | Structure | Name | NMR |
|---|---|---|---|
| 34 | 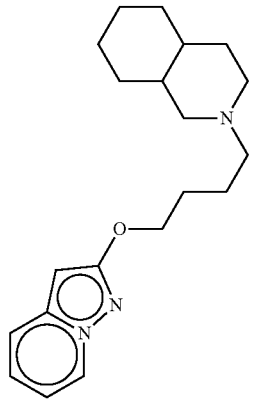 ·C$_4$H$_4$O$_4$ | 2-(4-(pyrazolo[1,5-a]pyridin-2-yloxy)butyl)decahydroisoquinoline fumarate | $^1$H NMR (DMSO) δ ppm: 8.43 (d, J = 7.0 Hz, 1H), 7.43 (d, J = 8.9 Hz, 1H), 7.24-7.05 (m, 1H), 6.71 (td, J = 6.9, 1.3 Hz, 1H), 6.56 (s, 2H), 5.95 (s, 1H), 4.20 (t, J = 6.3 Hz, 2H), 3.26-3.09 (m, 2H), 3.11-2.85 (m, 2H), 2.86-2.63 (m, 2H), 1.89-1.51 (m, 9H), 1.45-1.19 (m, 6H), 1.02-0.71 (m, 1H). |
| 35 | 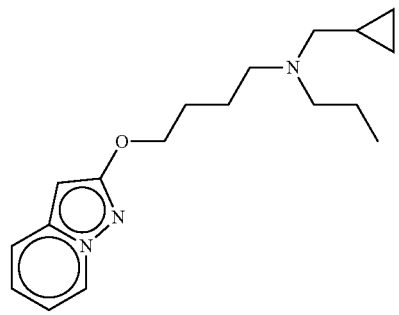 ·C$_4$H$_4$O$_4$ | N-(cyclopropylmethyl)-N-propyl-4-(pyrazolo[1,5-a]pyridin-2-yloxy)butan-1-amine maleate | $^1$H NMR (CD$_3$OD) δ ppm: 8.27 (d, J = 7.0 Hz, 1H), 7.41 (d, J = 8.9 Hz, 1H), 7.24-7.08 (m, 1H), 6.73 (td, J = 6.9, 1.3 Hz, 1H), 6.25 (s, 2H), 5.94 (s, 1H), 4.31 (t, J = 5.3 Hz, 2H), 3.31-3.24 (m, 2H), 3.23-3.13 (m, 2H), 3.09 (d, J = 7.3 Hz, 2H), 2.07-1.86 (m, 4H), 1.75 (dq, J = 14.7, 7.3 Hz, 2H), 1.20-1.06 (m, 1H), 1.02 (t, J = 7.4 Hz, 3H), 0.84-0.70 (m, 2H), 0.52-0.36 (m, 2H). |
| 36 | 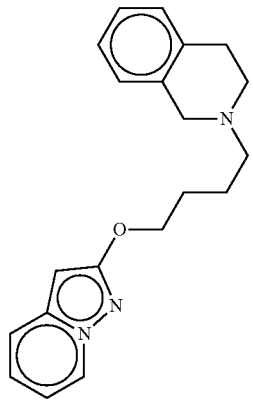 ·C$_4$H$_4$O$_4$ | 2-(4-(pyrazolo[1,5-a]pyridin-2-yloxy)butyl)-1,2,3,4-tetrahydroisoquinoline maleate | $^1$H NMR (CD$_3$OD) δ ppm: 8.27 (d, J = 7.0 Hz, 1H), 7.41 (d, J = 8.9 Hz, 1H), 7.37-7.24 (m, 3H), 7.24-7.11 (m, 2H), 6.74 (td, J = 6.9, 1.3 Hz, 1H), 6.26 (s, 2H), 5.94 (s, 1H), 4.61-4.37 (m, 2H), 4.33 (t, J = 5.8 Hz, 2H), 3.76-3.48 (m, 2H), 3.49-3.35 (m, 2H), 3.21 (t, J = 6.0 Hz, 2H), 2.19-2.01 (m, 2H), 2.00-1.88 (m, 2H). |
| 37 | 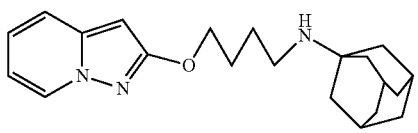 ·C$_4$H$_4$O$_4$ | N-adamantyl-4-(pyrazolo[1,5-a]pyridin-2-yloxy)-butan-1-amine maleate | $^1$H NMR (CD$_3$OD) δ ppm: 8.27 (d, J = 6.9 Hz, 1H), 7.40 (d, J = 8.9 Hz, 1H), 7.25-7.11 (m, 1H), 6.84-6.66 (m, 1H), 6.26 (s, 2H), 5.93 (s, 1H), 4.30 (t, J = 5.7 Hz, 2H), 3.19-3.00 (m, 2H), 2.29-2.21 (m, 3H), 2.06-1.63 (m, 16H). |

| Ex | Structure | Name | NMR |
|---|---|---|---|
| 38 | ·2C4H4O4 | 2-(4-(4-(1-methylpiperidin-4-yl)piperazin-1-yl)butoxy)pyrazolo[1,5-a]pyridine dimaleate | $^1$H NMR (CD$_3$OD) δ ppm: 8.27 (d, J = 7.0 Hz, 1H), 7.41 (d, J = 8.9 Hz, 1H), 7.24-7.02 (m, 1H), 6.74 (dd, J = 7.5, 6.3 Hz, 1H), 6.27 (s, 4H), 5.94 (s, 1H), 4.30 (t, J = 5.4 Hz, 2H), 3.72-3.35 (m, 8H), 3.27-3.16 (m, 3H), 3.15-2.97 (m, 3H), 2.87 (s, 3H), 2.77-2.50 (m, 1H), 2.27-2.06 (m, 2H), 2.05-1.81 (m, 4H), 1.82-1.61 (m, 2H). |
| 39 | ·C4H4O4 | 2-(2-(4-tert-butylpiperidin-1-yl)ethoxy)pyrazolo[1,5-a]pyridine maleate | $^1$H NMR (DMSO) δ ppm: 8.47 (d, J = 6.9 Hz, 1H), 7.49 (d, J = 8.9 Hz, 1H), 7.30-7.15 (m, 1H), 6.77 (t, J = 6.9 Hz, 1H), 6.05 (s, 1H), 6.02 (s, 2H), 4.64-4.46 (m, 2H), 3.69-3.44 (m, 4H), 3.08-2.84 (m, 2H), 1.92-1.71 (m, 2H), 1.59-1.36 (m, 2H), 1.36-1.17 (m, 1H), 0.85 (s, 9H). |
| 40 | ·C4H4O4 | N-methyl-N-phenethyl-2-(pyrazolo[1,5-a]pyridin-2-yloxy)ethanamine maleate | $^1$H NMR (DMSO) δ ppm: 8.48 (d, J = 6.9 Hz, 1H), 7.50 (d, J = 8.8 Hz, 1H), 7.41-7.12 (m, 6H), 6.77 (t, J = 6.9 Hz, 1H), 6.05 (s, 1H), 6.04 (s, 2H), 4.65-4.51 (m, 2H), 3.67-3.46 (m, 2H), 3.09-2.83 (m, 4H), 2.54 (s, 3H). |
| 41 | ·2C4H4O4 | 1-benzyl-N-methyl-N-(2-(pyrazolo[1,5-a]pyridin-2-yloxy)ethyl)piperidin-4-amine dimaleate | $^1$H NMR (DMSO) δ ppm: 8.45 (d, J = 6.9 Hz, 1H), 7.53-7.35 (m, 6H), 7.19 (dd, J = 8.4, 7.3 Hz, 1H), 6.76 (td, J = 6.9, 1.3 Hz, 1H), 6.08 (S, 2H), 6.01 (s, 1H), 4.57-4.36 (m, 2H), 4.09-3.84 (m, 2H), 3.29-3.10 (m, 5H), 2.71-2.60 (m, 2H), 2.14-1.91 (m, 2H), 1.74 (s, 2H). |

-continued

| Ex | Structure | Name | NMR |
|---|---|---|---|
| 42 | •C₄H₄O₄ | 2-(2-(pyrazolo[1,5-a]pyridin-2-yloxy)ethyl)decahydroisoquinoline maleate | ¹H NMR (DMSO) δ ppm: 8.47 (d, J = 6.9 Hz, 1H), 7.49 (d, J = 8.9 Hz, 1H), 7.26-7.15 (m, 1H), 6.77 (t, J = 6.7 Hz, 1H), 6.05 (s, 1H), 6.03 (s, 2H), 4.66-4.48 (m, 2H), 3.63-3.41 (m, 4H), 3.17-2.92 (m, 2H), 2.03-1.84 (m, 1H), 1.80-1.11 (m, 11H). |
| 43 | •C₄H₄O₄ | N-(cyclopropylmethyl)-N-(2-(pyrazolo[1,5-a]pyridin-2-yloxy)ethyl)propan-1-amine maleate | ¹H NMR (DMSO) δ ppm: 8.48 (d, J = 6.9 Hz, 1H), 7.50 (d, J = 8.9 Hz, 1H), 7.26-7.16 (m, 1H), 6.78 (dd, J = 7.6, 6.2 Hz, 1H), 6.05 (s, 1H), 6.04 (s, 2H), 4.58 (t, J = 4.4 Hz, 2H), 3.72-3.57 (m, 2H), 3.23-3.04 (m, 4H), 1.79-1.56 (m, 2H), 1.17-1.02 (m, 1H), 0.92 (t, J = 7.3 Hz, 3H), 0.72-0.58 (m, 2H), 0.44-0.32 (m, 2H). |
| 44 | •C₄H₄O₄ | 2-(2-(pyrazolo[1,5-a]pyridin-2-yloxy)ethyl)-1,2,3,4-tetrahydroisoquinoline maleate | ¹H NMR (CD₃OD) δ ppm: 8.32 (d, J = 7.0 Hz, 1H), 7.44 (dd, J = 8.9, 0.9 Hz, 1H), 7.41-7.10 (m, 5H), 6.77 (t, J = 6.9 Hz, 1H), 6.24 (s, 2H), 6.03 (s, 1H), 4.73 (dd, J = 5.3, 4.4 Hz, 2H), 4.58 (s, 2H), 3.80-3.75 (m, 2H), 3.72 (t, J = 6.1 Hz, 2H), 3.24 (t, J = 6.3 Hz, 2H). |
| 45 | •2C₄H₄O₄ | 2-(2-(1,4'-bipiperidin-1'-yl)ethoxy)pyrazolo[1,5-a]pyridine dimaleate | ¹H NMR (DMSO) δ ppm: 8.47 (d, J = 6.9 Hz, 1H), 7.50 (d, J = 8.9 Hz, 1H), 7.27-7.13 (m, 1H), 6.78 (td, J = 6.9, 1.4 Hz, 1H), 6.23 (s, 4H), 6.05 (s, 1H), 4.66-4.45 (m, 2H), 3.81-3.61 (m, 2H), 3.61-3.48 (m, 2H), 3.48-3.28 (m, 3H), 3.18-2.91 (m, 3H), 2.81-2.66 (m, 1H), 2.33-2.12 (m, 2H), 2.09 |
| 46 | •2C₄H₄O₄ | 2-(2-(4-(1-methylpiperidin-4-yl)piperazin-1-yl)ethoxy)pyrazolo[1,5-a]pyridine dimaleate | ¹H NMR (DMSO) δ ppm: 8.45 (d, J = 7.0 Hz, 1H), 7.47 (d, J = 8.1 Hz, 1H), 7.28-7.07 (m, 1H), 6.76 (t, J = 6.9 Hz, 1H), 6.05 (s, 4H), 6.02 (s, 1H), 4.61-4.33 (m, 2H), 3.57-3.15 (m, 11H), 2.99-2.81 (m, 4H), 2.74 (s, 3H), 2.14-1.84 (m, 2H), 1.69-1.48 (m, 2H). |

| Ex | Structure | Name | NMR |
|---|---|---|---|
| 47 | •2C₄H₄O₄ | 2-(2-(4-cyclohexylpiperazin-1-yl)ethoxy)pyrazolo[1,5-a]pyridine dimaleate | ¹H NMR (DMSO) δ ppm: 8.44 (d, J = 6.8 Hz, 1H), 7.45 (d, J = 8.9 Hz, 1H), 7.23-7.10 (m, 1H), 6.74 (t, J = 6.7 Hz, 1H), 6.16 (s, 4H), 5.98 (s, 1H), 4.34 (t, J = 4.3 Hz, 2H), 3.19-2.78 (m, 6H), 2.11-1.92 (m, 2H), 1.87-1.70 (m, 2H), 1.67-1.54 (m, 1H), 1.42-0.97 (m, 9H), 0.96-0.75 (m, 1H). |
| 48 | •2C₄H₄O₄ | 1'-(2-(pyrazolo[1,5-a]pyridin-2-yloxy)ethyl)-3H-spiro[isobenzofuran-1,4'-piperidine] dimaleate | ¹H NMR (DMSO) δ ppm: 8.48 (d, J = 6.9 Hz, 1H), 7.50 (d, J = 8.9 Hz, 1H), 7.40-7.29 (m, 3H), 7.29-7.11 (m, 2H), 6.78 (t, J = 6.8 Hz, 1H), 6.07 (s, 1H), 6.03 (s, 2H), 5.05 (s, 2H), 4.71-4.47 (m, 2H), 3.76-3.49 (m, 4H), 3.32-3.07 (m, 2H), 2.36-2.08 (m, 2H), 1.96-1.74 (m, 2H). |
| 49 | •C₄H₄O₄ | 2-(4-(azepan-1-yl)butoxy)pyrazolo[1,5-a]pyridine maleate | ¹H NMR (CDCl₃) δ ppm: 8.21 (d, J = 6.9 Hz, 1H), 7.31 (d, J = 9.1 Hz, 1H), 7.12-6.96 (m, 1H), 6.62 (dd, J = 7.6, 6.2 Hz, 1H), 6.28 (s, 2H), 5.82 (s, 1H), 4.28 (t, J = 5.7 Hz, 2H), 3.63-3.47 (m, 2H), 3.22-3.04 (m, 2H), 3.04-2.85 (m, 2H), 2.07-1.94 (m, 4H), 1.94-1.74 (m, 6H), 1.72-1.57 (m, 2H). |
| 50 | •C₄H₄O₄ | N-(4-(pyrazolo[1,5-a]pyridin-2-yloxy)butyl)cyclohexanamine maleate | ¹H NMR (CDCl₃) δ ppm: 8.19 (d, J = 6.9 Hz, 1H), 7.29 (d, J = 9.0 Hz, 1H), 7.11-6.98 (m, 1H), 6.60 (td, J = 6.9, 1.3 Hz, 1H), 6.25 (s, 2H), 5.80 (s, 1H), 4.26 (t, J = 5.8 Hz, 2H), 3.13 (t, J = 7.2 Hz, 2H), 3.09-2.95 (m, 1H), 2.23-2.06 (m, 2H), 2.05-1.39 (m, 8H), 1.38-1.06 (m, 4H) |

| Ex | Structure | Name | NMR |
|---|---|---|---|
| 51 | 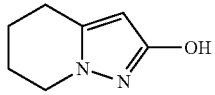•C₄H₄O₄ | (4aR,8aS)-2-(4-(pyrazolo[1,5-a]pyridin-2-yloxy)butyl)decahydroisoquinoline maleate | ¹H NMR (CDCl₃) δ ppm: 8.21 (dd, J = 7.0, 1.0 Hz, 1H), 7.34-7.28 (m, 1H), 7.06 (ddd, J = 8.9, 6.8, 1.1 Hz, 1H), 6.62 (td, J = 6.9, 1.4 Hz, 1H), 6.27 (s, 2H), 5.81 (d, J = 0.8 Hz, 1H), 4.26 (t, J = 5.7 Hz, 2H), 3.69-3.60 (m, 1H), 3.45-3.36 (m, 1H), 3.13-2.99 (m, 2H), 2.70-2.54 (m, 1H), 2.35-2.21 (m, 1H), 2.06-1.92 (m, 2H), 1.92-1.82 (m, 2H), 1.82-1.52 (m, 5H), 1.41-1.22 (m, 2H), 1.14-1.02 (m, 2H), 1.01-0.84 (m, 1H). |

Synthesis of Compounds of General Formula (Id)

Example 52

Synthesis of 2-(2-(4-ethylpiperazin-1-yl)ethoxy)-4,5,6,7-tetrahydropyrazolo[1,5-a]pyridine maleate 52a. Synthesis of 4,5,6,7-tetrahydropyrazolo[1,5-a]pyridin-2-ol

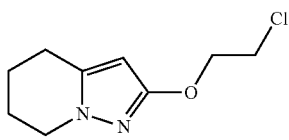 [SMILES: ClCCOc1cc2n(n1)CCCC2]

A solution of pyrazolo[1,5-a]pyridin-2-ol (7.5 g, 0.056 mol) in 280 mL of AcOH was hydrogenated over 2.5 g of 10 wt % Pd/C dry powder for 20 h under atmospheric pressure of hydrogen. After 72 h, the suspension was filtered over decalite and concentrated under vacuum to afford an orange residue that was suspended in hot IPA and stirred for 15 min, then cooled to 0° C. and filtered to afford 4.84 g of a cream colored solid. The filtrate was concentrated under vacuum, and recrystallized from EtOAc to afford additional 2.62 g (global 96%).
¹H NMR (CDCl₃) δ ppm: 5.32 (s, 1H), 3.91 (t, J=6.1 Hz, 2H), 2.69 (t, J=6.3 Hz, 2H), 2.06-1.91 (m, 2H), 1.86-1.69 (m, 2H).

52b. Synthesis of 2-(2-chloroethoxy)-4,5,6,7-tetrahydropyrazolo[1,5-a]pyridine

A solution of 4,5,6,7-tetrahydropyrazolo[1,5-a]pyridin-2-ol (0.531 g, 3.84 mmol) in 50 mL toluene, 50 mL of a 40% aqueous solution of NaOH, 0.96 mL (11.53 mmol) of 1-bromo-2-chloroethane and tetrabutylammonium sulfate (catalytic) was refluxed for 4 h. The organic layer was extracted and washed with water, dried and concentrated under vacuum to afford 0.418 g (33%) of yellow oil.

52c. Synthesis of 2-(2-(4-ethylpiperazin-1-yl)ethoxy)-4,5,6,7-tetrahydropyrazolo[1,5-a]pyridine maleate (Example 52)

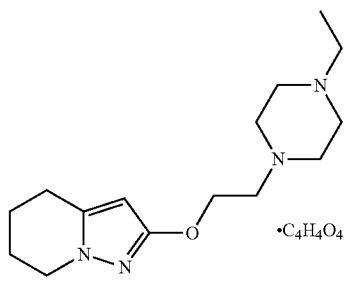

A solution of 2-(2-chloroethoxy)-4,5,6,7-tetrahydropyrazolo[1,5-a]pyridine (35 mg, 0.174 mmol), potassium carbonate (52 mg, 0.523 mmol), ethylpiperazine (30 mg, 0.262 mmol) and NaI (catalytic amount) in 2 mL of DMF, was heated to 95-100° C. under nitrogen for 18 h. The mixture was allowed to cool to room temperature and evaporated to dryness. The residue was partitioned between water and EtOAc, the organic layer washed with water, dried and concentrated under vacuum to afford 28 mg of a yellow oil, that was subsequently purified by flash chromatography with an eluent gradient of EtOAc/MeOH from 80:20 to 60:40 to give 10 mg (21%) of colorless oil. Maleate salt was obtained following the same procedure as for example 1.
¹H NMR (CDCl₃) δ ppm: 6.28 (s, 2H), 5.36 (s, 1H), 4.29-4.21 (m, 2H), 3.93 (t, J=6.1 Hz, 2H), 3.58-3.36 (m, 2H), 3.25-3.08 (m, 2H), 3.09-2.97 (m, 2H), 2.97-2.80 (m, 6H), 2.69 (t, J=6.4 Hz, 2H), 2.06-1.93 (m, 2H), 1.87-1.73 (m, 2H), 1.37 (t, J=7.3 Hz, 3H).

Example 52 can be, alternatively, obtained according to the following procedure for example 53, from 4,5,6,7-tetrahydropyrazolo[1,5-a]pyridin-2-ol:

Example 53

Synthesis of 2-(2-(azepan-1-yl)ethoxy)-4,5,6,7-tetrahydropyrazolo[1,5-a]pyridine maleate

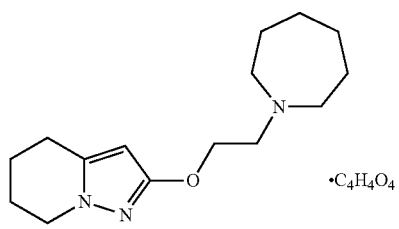

A solution of 4,5,6,7-tetrahydropyrazolo[1,5-a]pyridin-2-ol (66 mg, 0.477 mmol), potassium carbonate (264 mg, 1.91 mmol), 2-(hexamethylenimino)ethyl chloride hydrochloride (142 mg, 0.717 mmol) and NaI (catalytic amount) in 3 mL of DMF, was heated to 90° C. under nitrogen for 18 h. The mixture was allowed to cool to room temperature and evaporated to dryness. The residue was partitioned between water and EtOAc, the organic layer washed with water, dried and concentrated under vacuum to afford a residue of 101 mg that was purified by flash chromatography on silica gel with EtOAc/MeOH eluent mixtures from 90:10 to 60:40 with 1% TEA to give 58 mg (46%) of yellow oil. Maleate salt was obtained following the same procedure as for example 1.

$^1$H NMR (CDCl$_3$) δ ppm: 6.28 (s, 2H), 5.36 (s, 1H), 4.55-4.44 (m, 2H), 3.93 (t, J=6.1 Hz, 2H), 3.77-3.53 (m, 2H), 3.55-3.45 (m, 2H), 3.23-3.05 (m, 2H), 2.70 (t, J=6.3 Hz, 2H), 2.09-1.87 (m, 6H), 1.87-1.47 (m, 6H).

Alternatively, example 53 can be obtained according to the procedure described for example 52 from 2-(2-chloroethoxy)-4,5,6,7-tetrahydropyrazolo[1,5-a]pyridine (compound of formula IId).

Examples 54 to 104 were prepared according to the procedure described in Example 52 and/or 53

| Ex. | Structure | Name | NMR |
|---|---|---|---|
| 54 | ·C₂H₂O₄ | 2-(2-(piperidin-1-yl)ethoxy)-4,5,6,7-tetrahydropyrazolo[1,5-a]pyridineoxalate | $^1$H NMR (DMSO) δ ppm: 5.46 (s, 1H), 4.39-4.27 (m, 2H), 3.85 (t, J = 6.1 Hz, 2H), 3.39-3.26 (m, 2H), 3.19-2.98 (m, 4H), 2.64 (t, J = 6.3 Hz, 2H), 2.00-1.84 (m, 2H), 1.79-1.64 (m, 6H), 1.59-1.41 (m, 2H). |
| 55 | ·C₂H₂O₄ | N,N-diethyl-2-(4,5,6,7-tetrahydropyrazolo[1,5-a]pyridin-2-yloxy)ethanamine oxalate | $^1$H NMR (DMSO) δ: ppm 5.46 (s, 1H), 4.36-4.26 (m, 2H), 3.85 (t, J = 6.1 Hz, 2H), 3.42-3.32 (m, 2H), 3.11 (q, J = 7.0 Hz, 4H), 2.64 (t, J = 6.3 Hz, 2H), 2.02-1.83 (m, 2H), 1.82-1.63 (m, 2H), 1.17 (t, J = 7.2 Hz, 6H). |
| 56 | ·C₂H₂O₄ | 4-(4-(4,5,6,7-tetrahydropyrazolo[1,5-a]pyridin-2-yloxy)butyl)morpholine oxalate | $^1$H NMR (DMSO) δ ppm: 5.37 (s, 1H), 4.00 (t, J = 5.5 Hz, 2H), 3.82 (t, J = 6.1 Hz, 2H), 3.78-3.69 (m, 4H), 3.12-2.99 (m, 4H), 2.99-2.89 (m, 2H), 2.62 (t, J = 6.3 Hz, 2H), 1.98-1.83 (m, 2H), 1.77-1.61 (m, 6H). |

| Ex. | Structure | Name | NMR |
|---|---|---|---|
| 57 | 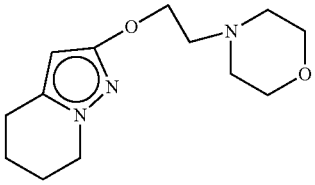 •C₂H₂O₄ | 4-(2-(4,5,6,7-tetrahydropyrazolo[1,5-a]pyridin-2-yloxy)ethyl)morpholine oxalate | ¹H NMR (DMSO) δ ppm: 5.42 (s, 1H), 4.22 (t, J = 5.3 Hz, 2H), 3.83 (t, J = 6.1 Hz, 2H), 3.74-3.60 (m, 4H), 3.03 (t, J = 5.2 Hz, 2H), 2.88-2.75 (m, 4H), 2.63 (t, J = 6.3 Hz, 2H), 1.99-1.82 (m, 2H), 1.77-1.62 (m, 2H). |
| 58 | 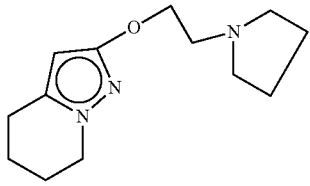 •C₂H₂O₄ | 2-(2-(pyrrolidin-1-yl)ethoxy)-4,5,6,7-tetrahydropyrazolo[1,5-a]pyridine oxalate | ¹H NMR (DMSO) δ ppm: 5.46 (s, 1H), 4.34-4.24 (m, 2H), 3.85 (t, J = 6.0 Hz, 2H), 3.52-3.40 (m, 2H), 3.36-3.13 (m, 4H), 2.64 (t, J = 6.3 Hz, 2H), 1.98-1.84 (m, 6H), 1.80-1.62 (m, 2H). |
| 59 | 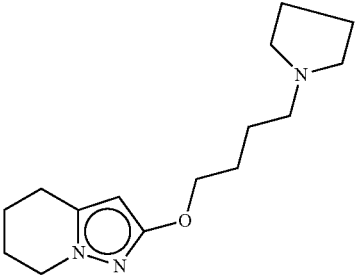 •C₂H₂O₄ | 2-(4-(pyrrolidin-1-yl)butoxy)-4,5,6,7-tetrahydropyrazolo[1,5-a]pyridine oxalate | ¹H NMR (DMSO) δ ppm: 5.38 (s, 1H), 4.00 (t, J = 5.5 Hz, 2H), 3.82 (t, J = 6.1 Hz, 2H), 3.37-2.99 (m, 4H), 3.17-3.06 (m, 2H), 2.62 (t, J = 6.3 Hz, 2H), 1.98-1.84 (m, 6H), 1.78-1.62 (m, 6H). |
| 60 | 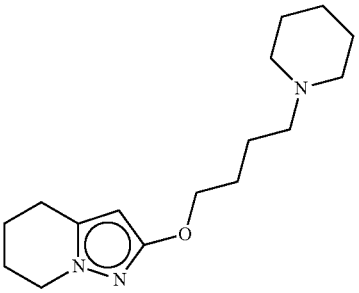 •C₂H₂O₄ | 2-(4-(piperidin-1-yl)butoxy)-4,5,6,7-tetrahydropyrazolo[1,5-a]pyridine oxalate | ¹H NMR (DMSO) δ: ppm 5.38 (s, 1H), 4.01 (t, J = 5.8 Hz, 2H), 3.82 (t, J = 6.1 Hz, 2H), 3.06-2.94 (m, 2H), 3.31-2.84 (m, 4H), 2.63 (t, J = 6.3 Hz, 2H), 1.98-1.84 (m, 2H), 1.83-1.59 (m, 10H), 1.59-1.43 (m, 2H). |
| 61 | 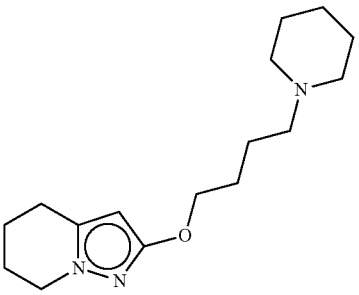 •C₄H₄O₄ | 2-(4-(piperidin-1-yl)butoxy)-4,5,6,7-tetrahydropyrazolo[1,5-a]pyridine maleate | ¹HNMR (CDCl₃) δ ppm: 6.30 (S, 2H), 5.35 (s, 1H), 4.10 (t, J = 5.8 Hz, 2H), 3.94 (t, J = 6.1 Hz, 2H), 3.62-3.49 (m, 2H), 3.13-2.98 (m, 2H), 2.70 (t, J = 6.4 Hz, 2H), 2.65-2.53 (m, 2H), 2.17-1.92 (m, 6H), 1.90-1.73 (m, 7H), 1.55-1.28 (m, 1H). |

| Ex. | Structure | Name | NMR |
|---|---|---|---|
| 62 | ·C₂H₂O₄ | N,N-diethyl-4-(4,5,6,7-tetrahydropyrazolo[1,5-a]pyridin-2-yloxy)butan-1-amine oxalate | ¹H NMR (DMSO) δ ppm: 5.38 (s, 1H), 4.09-3.97 (m, 2H), 3.82 (t, J = 6.1 Hz, 2H), 3.08 (q, J = 7.3 Hz, 4H), 3.09-2.96 (m, 2H), 2.62 (t, J = 6.3 Hz, 2H), 1.99-1.84 (m, 2H), 1.78-1.63 (m, 6H), 1.17 (t, J = 7.2 Hz, 6H). |
| 63 | ·C₂H₂O₄ | 2-(4-(4-phenylpiperidin-1-yl)butoxy)-4,5,6,7-tetrahydropyrazolo[1,5-a]pyridine oxalate | ¹H NMR (DMSO) δ ppm: 7.39-7.29 (m, 2H), 7.29-7.16 (m, 3H), 5.39 (s, 1H), 4.03 (t, J = 5.6 Hz, 2H), 3.83 (t, J = 5.9 Hz, 2H), 3.58-3.48 (m, 2H), 3.16-3.05 (m, 2H), 3.05-2.93 (m, 2H), 2.87-2.73 (m, 1H), 2.63 (t, J = 6.2 Hz, 2H), 2.01-1.85 (m, 4H), 1.83-1.65 (m, 4H). |
| 64 | ·C₂H₂O₄ | N-benzyl-N-methyl-2-(4,5,6,7-tetrahydropyrazolo[1,5-a]pyridin-2-yloxy)ethanamine oxalate | ¹H NMR (DMSO) δ ppm: 7.48-7.30 (m, 5H), 5.42 (s,1H), 4.26 (t, J = 4.9 Hz, 2H), 4.00 (s, 2H), 3.83 (t, J = 5.9 Hz, 2H), 3.18-2.99 (m, 2H), 2.63 (t, J = 6.2 Hz, 2H), 2.51 (s, 3H), 2.02-1.83 (m, 2H), 1.78-1.60 (m, 2H). |
| 65 | ·C₄H₄O₄ | 2-(4-(4-tert-butylpiperidin-1-yl)butoxy)-4,5,6,7-tetrahydropyrazolo[1,5-a]pyridine maleate | ¹H NMR (DMSO) δ ppm: 6.02 (s, 2H), 5.38 (s, 1H), 4.02 (t, J = 4.2 Hz, 2H), 3.82 (t, J = 6.0 Hz, 2H), 3.59-3.41 (m, 2H), 3.12-2.98 (m, 2H), 2.93-2.74 (m, 2H), 2.63 (t, J = 6.2 Hz, 2H), 1.97-1.59 (m, 10H), 1.53-1.17 (m, 3H), 0.85 (s, 9H). |
| 66 | ·C₄H₄O₄ | 2-(2-(4-tert-butylpiperidin-1-yl)ethoxy)-4,5,6,7-tetrahydropyrazolo[1,5-a]pyridine maleate | ¹H NMR (CDCl₃) δ ppm: 6.27 (s, 2H), 5.36 (s, 1H), 4.55-4.41 (m, 2H), 3.93 (t, J = 6.1 Hz, 2H), 3.78-3.62 (m, 2H), 3.46-3.32 (m, 2H), 2.84-2.72 (m, 2H), 2.69 (t, J = 6.3 Hz, 2H), 2.09-1.94 (m, 2H), 1.94-1.59 (m, 6H), 1.34-1.07 (m, 1H), 0.88 (s, 9H). |

| Ex. | Structure | Name | NMR |
|---|---|---|---|
| 67 | ·2C₄H₄O₄ | 1-benzyl-N-methyl-N-(4-(4,5,6,7-tetrahydropyrazolo[1,5-a]pyridin-2-yloxy)butyl)piperidin-4-amine dimaleate | ¹H NMR (CD₃OD) δ ppm: 7.47-7.37 (m, 5H), 6.27 (s, 4H), 5.43 (s, 1H), 4.08 (t, J = 5.6 Hz, 2H), 4.00 (s, 2H), 3.88 (t, J = 6.1 Hz, 2H), 3.59-3.32 (m, 3H), 3.27-3.16 (m, 2H), 2.83 (s, 3H), 2.76-2.61 (m, 4H), 2.26-2.08 (m, 2H), 2.10-1.70 (m, 10H). |
| 68 | ·C₄H₄O₄ | 2-(4-(4,5,6,7-tetrahydropyrazolo[1,5-a]pyridin-2-yloxy)butyl)decahydro-isoquinoline maleate | ¹H NMR (DMSO) δ ppm: 6.01 (s, 2H), 5.37 (s, 1H), 4.01 (t, J = 5.2 Hz, 2H), 3.82 (t, J = 6.0 Hz, 2H), 3.24-2.76 (m, 6H), 2.62 (t, J = 6.3 Hz, 2H), 1.99-1.84 (m, 3H), 1.81-1.45 (m, 12H), 1.46-1.06 (m, 4H), 0.99-0.81 (m, 1H). |
| 69 | ·C₄H₄O₄ | 2-(4-(4-cyclohexylpiperazin-1-yl)butoxy)-4,5,6,7-tetrahydropyrazolo[1,5-a]pyridine maleate | ¹H NMR (CD₃OD) δ ppm: 6.26 (s, 2H), 5.42 (s, 1H), 4.05 (t, J = 5.8 Hz, 2H), 3.89 (t, J = 6.1 Hz, 2H), 3.27-2.78 (m, 8H), 2.77-2.60 (m, 5H), 2.13-1.96 (m, 4H), 1.96-1.87 (m, 2H), 1.87-1.62 (m, 6H), 1.50-1.03 (m, 6H). |

| Ex. | Structure | Name | NMR |
|---|---|---|---|
| 70 | ·C₄H₄O₄ | 1'-(4-(4,5,6,7-tetrahydropyrazolo[1,5-a]pyridin-2-yloxy)butyl)-3H-spiro[isobenzofuran-1,4'-piperidine]maleate | ¹H NMR (DMSO) δ ppm: 7.39-7.28 (m, 3H), 7.23-7.12 (m, 1H), 6.01 (s, 2H), 5.39 (s, 1H), 5.04 (s, 2H), 4.05 (t, J = 5.3 Hz, 2H), 3.83 (t, J = 6.0 Hz, 2H), 3.61-3.43 (m, 2H), 3.24-3.08 (m, 4H), 2.63 (t, J = 6.2 Hz, 2H), 2.20-2.01 (m, 2H), 2.00-1.60 (m, 10H). |
| 71 | ·C₄H₄O₄ | 2-(2-(4-cyclohexylpiperazin-1-yl)ethoxy)-4,5,6,7-tetrahydropyrazolo[1,5-a]pyridine maleate | ¹H NMR (CDCl₃) δ ppm: 6.28 (s, 2H), 5.36 (s, 1H), 4.31 (t, J = 5.0 Hz, 2H), 3.93 (t, J = 6.1 Hz, 2H), 3.48-3.08 (m, 9H), 3.00 (t, J = 4.8 Hz, 2H), 2.69 (t, J = 6.3 Hz, 2H), 2.24-2.09 (m, 2H), 2.07-1.88 (m, 4H), 1.88-1.64 (m, 3H), 1.57-1.04 (m, 5H). |
| 72 | ·C₄H₄O₄ | 1-benzyl-N-methyl-N-(2-(4,5,6,7-tetrahydropyrazolo[1,5-a]pyridin-2-yloxy)ethyl)piperidin-4-amine maleate | ¹H NMR (CDCl₃) δ ppm: 7.49-7.34 (m, 5H), 6.29 (s, 2H), 5.35 (s, 1H), 4.56-4.34 (m, 2H), 3.92 (t, J = 5.9 Hz, 2H), (3.99-3.77 (m, 2H), 3.44-3.20 (m, 4H), 2.69 (s, 3H), 2.69 (t, J = 6.1 Hz, 2H), 2.55-2.35 (m, 1H), 2.26-2.07 (m, 4H), 2.04-1.93 (m, 4H), 1.93-1.39 (m, 2H). |
| 73 | ·C₄H₄O₄ | 2-(2-(4-(1-methylpiperidin-4-yl)piperazin-1-yl)ethoxy)-4,5,6,7-tetrahydropyrazolo[1,5-a]pyridine maleate | ¹H NMR (CDCl₃) δ ppm: 6.28 (s, 2H), 5.37 (s, 1H), 4.36-4.17 (m, 2H), 3.93 (t, J = 5.5 Hz, 2H), 3.48-3.23 (m, 1H), 3.02-2.48 (m, 17H), 2.15-1.89 (m, 4H), 1.88-1.43 (m, 4H). |

| Ex. | Structure | Name | NMR |
|---|---|---|---|
| 74 | •C₄H₄O₄ | 1'-(2-(4,5,6,7-tetrahydropyrazolo[1,5-a]pyridin-2-yloxy)ethyl)-3H-spiro[isobenzofuran-1,4'-piperidine]maleate | $^1$H NMR (CDCl$_3$) δ ppm: 7.38-7.29 (m, 2H), 7.24- 7.14 (m, 2H), 6.32 (s, 2H), 5.38 (s, 1H), 5.08 (s, 2H), 4.54 (dd, J = 5.5, 3.7 Hz, 2H), 3.94 (t, J = 6.1 Hz, 2H), 3.73-3.61 (m, 2H), 3.53-3.44 (m, 2H), 3.40-3.24 (m, 2H), 2.70 (t, J = 6.3 Hz, 2H), 2.58-2.35 (m, 2H), 2.08-1.94 (m, 2H), 1.96-1.76 (m, 4H). |
| 75 | •C₄H₄O₄ | N-adamantyl-2-(4,5,6,7-tetrahydropyrazolo[1,5-a]pyridin-2-yloxy)ethanamine maleate | $^1$H NMR (CDCl$_3$) δ ppm: 6.29 (s, 2H), 5.40 (s, 1H), 4.48-4.36 (m, 2H), 3.95 (t, J = 6.1 Hz, 2H), 3.42-3.30 (m, 2H), 2.71 (t, J = 6.3 Hz, 2H), 2.29-2.15 (m, 3H), 2.12-1.97 (m, 2H), 2.00- 1.90 (m, 6H), 1.90-1.80 (m, 2H), 1.80-1.58 (m, 6H). |
| 76 | •C₄H₄O₄ | 2-(2-(1,4'-bipiperidin-1'-yl)ethoxy)-4,5,6,7-tetrahydropyrazolo[1,5-a]pyridine maleate | $^1$H NMR (CDCl$_3$) δ ppm: 6.28 (s, 2H), 5.37 (s, 1H), 4.22 (t, J = 5.3 Hz, 2H), 3.94 (t, J = 6.1 Hz, 2H), 3.25-3.08 (m, 4H), 3.59-3.00 (m, 2H), 2.81 (t, J = 5.1 Hz, 2H), 3.00-2.55 (m, 2H), 2.69 (t, J = 6.3 Hz, 2H), 2.22 (t, J = 11.7 Hz, 2H), 2.10-1.88 (m, 9H), 1.88-1.74 (m, 6H). |
| 77 | •C₄H₄O₄ | 2-(2-(4,5,6,7-tetrahydropyrazolo[1,5-a]pyridin-2-yloxy)ethyl)-1,2,3,4-tetrahydroisoquinoline maleate | $^1$H NMR (CDCl$_3$) δ ppm: 7.30-7.16 (m, 3H), 7.11 (d, J = 6.9 Hz, 1H), 6.25 (s, 2H), 5.40 (s, 1H), 4.69-4.54 (m, 2H), 4.53-4.34 (m, 2H), 3.93 (t, J = 6.0 Hz, 2H), 3.69-3.51 (m, 4H), 3.33-3.15 (m, 2H), 2.70 (t, J = 6.3 Hz, 2H), 2.08-1.92 (m, 2H), 1.91-1.69 (m, 2H). |
| 78 | •C₄H₄O₄ | 2-(4-(azepan-1-yl)butoxy)-4,5,6,7-tetrahydropyrazolo[1,5-a]pyridine maleate | $^1$H NMR (CDCl$_3$) δ ppm: 6.30 (s, 2H), 5.36 (s, 1H), 4.10 (t, J = 5.8 Hz, 2H), 3.94 (t, J = 6.1 Hz, 2H), 3.64-3.41 (m, 2H), 3.17-3.03 (m, 2H), 3.02-2.84 (m, 2H), 2.70 (t, J = 6.3 Hz, 2H), 2.09-1.92 (m, 6H), 1.88-1.75 (m, 7H), 1.71-1.53 (m, 3H). |

| Ex. | Structure | Name | NMR |
|---|---|---|---|
| 79 | 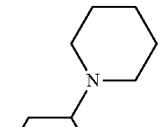 •C4H4O4 | 2-(4-(1,4'-bipiperidin-N-yl)butoxy)-4,5,6,7-tetrahydropyrazolo[1,5-a]pyridine maleate | ¹H NMR (CDCl₃) δ ppm: 6.27 (s, 2H), 5.35 (s, 1H), 4.08 (t, J = 6.1 Hz, 2H), 3.94 (t, J = 6.1 Hz, 2H), 3.23-3.06 (m, 2H), 3.06-2.80 (m, 4H), 2.69 (t, J = 6.3 Hz, 2H), 2.58-2.40 (m, 2H), 2.18-1.46 (m, 19H). |
| 80 | 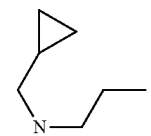 •C4H4O4 | N-(cyclopropylmethyl)-N-propyl-4-(4,5,6,7-tetrahydropyrazolo[1,5-a]pyridin-2-yloxy)butan-1-amine maleate | ¹H NMR (CDCl₃) δ ppm: 6.26 (s, 2H), 5.35 (s, 1H), 4.12 (t, J = 5.5 Hz, 2H), 3.93 (t, J = 6.1 Hz, 2H), 3.21 (d, J = 5.0 Hz, 2H), 3.06 (d, J = 8.3 Hz, 2H), 2.96 (d, J = 7.1 Hz, 2H), 2.70 (t, J = 6.3 Hz, 2H), 2.07-1.94 (m, 2H), 1.93-1.66 (m, 8H), 1.11-0.88 (m, 1H), 1.00 (t, J = 7.4 Hz, 3H), 0.84-0.67 (m, 2H), 0.46-0.29 (m, 2H). |
| 81 | 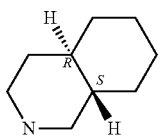 •C4H4O4 | (4aR,8aS)-2-(4-(4,5,6,7-tetrahydropyrazolo[1,5-a]pyridin-2-yloxy)butyl)decahydro-isoquinoline maleate | ¹H NMR (CDCl₃) δ ppm: 6.28 (s, 2H), 5.35 (s, 1H), 4.09 (t, J = 5.7 Hz, 2H), 3.94 (t, J = 6.1 Hz, 2H), 3.72-3.56 (m, 1H), 3.47-3.31 (m, 1H), 3.12-2.96 (m, 2H), 2.70 (t, J = 6.3 Hz, 2H), 2.68-2.52 (m, 1H), 2.37-2.16 (m, 1H), 2.08-1.87 (m, 4H), 1.87-1.56 (m, 11H), 1.41-1.24 (m, 2H), 1.15-0.82 (m, 3H). |
| 82 | 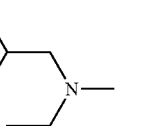 •C4H4O4 | N-benzyl-N-methyl-4-(4,5,6,7-tetrahydropyrazolo[1,5-a]pyridin-2-yloxy)butan-1-amine maleate | ¹H NMR (CDCl₃) δ ppm: 7.55-7.37 (m, 5H), 6.31 (s, 2H), 5.35 (s, 1H), 4.33-4.03 (m, 2H), 4.10 (t, J = 5.7 Hz, 2H), 3.94 (t, J = 6.1 Hz, 2H), 3.27-2.86 (m, 2H), 2.77-2.65 (m, 2H), 2.70 (s, 3H), 2.09-1.90 (m, 4H), 1.89-1.72 (m, 4H). |
| 83 | 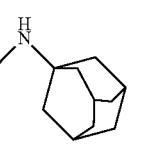 •C4H4O4 | N-adamantyl-4-(4,5,6,7-tetrahydropyrazolo[1,5-a]pyridin-2-yloxy)butan-1-amine maleate | ¹H NMR (CDCl₃) δ ppm: 6.26 (s, 2H), 5.37 (s, 1H), 4.10 (t, J = 5.7 Hz, 2H), 3.94 (t, J = 6.1 Hz, 2H), 3.17-2.98 (m, 2H), 2.70 (t, J = 6.3 Hz, 2H), 2.26-2.13 (m, 3H), 2.06-1.94 (m, 6H), 2.06-1.90 (m, 4H), 1.89-1.77 (m, 4H), 1.77-1.56 (m, 6H). |

| Ex. | Structure | Name | NMR |
|---|---|---|---|
| 84 | 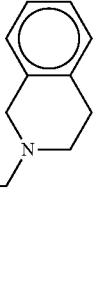 ·C₄H₄O₄ | 2-(4-(4,5,6,7-tetrahydropyrazolo[1,5-a]pyridin-2-yloxy)butyl)-1,2,3,4-tetrahydroisoquinoline maleate | $^1$H NMR (CDCl$_3$) δ ppm: 7.26-7.14 (m, 3H), 7.08 (d, J = 6.8 Hz, 1H), 6.22 (s, 2H), 5.35 (s, 1H), 4.12 (t, J = 5.9 Hz, 2H), 4.26-4.05 (m, 2H), 3.93 (t, J = 6.1 Hz, 2H), 3.39-3.19 (m, 2H), 3.16-2.97 (m, 4H), 2.69 (t, J = 6.4 Hz, 2H), 2.06-1.90 (m, 4H), 1.91-1.74 (m, 4H). |
| 85 | 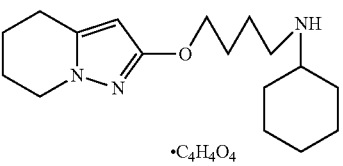 ·C₄H₄O₄ | N-(4-(4,5,6,7-tetrahydropyrazolo[1,5-a]pyridin-2-yloxy)butyl) cyclohexanamine maleate | $^1$H NMR (CDCl$_3$) δ ppm: 9.25-8.92 (m, 2H), 6.27 (s, 2H), 5.37 (s, 1H), 4.10 (t, J = 5.7 Hz, 2H), 3.94 (t, J = 6.1 Hz, 2H), 3.20-3.05 (m, 2H), 3.06-2.93 (m, 1H), 2.70 (t, J = 6.3 Hz, 2H), 2.22-2.08 (m, 2H), 2.07-1.91 (m, 4H), 1.91-1.75 (m, 6H), 1.72-1.62 (m, 1H), 1.61-1.41 (m, 2H), 1.39-1.13 (m, 3H). |
| 86 | 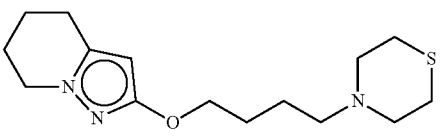 ·C₄H₄O₄ | 4-(4-(4,5,6,7-tetrahydropyrazolo[1,5-a]pyridin-2-yloxy)butyl) thiomorpholine maleate | $^1$H NMR (CDCl$_3$) δ ppm: 6.28 (s, 2H), 5.35 (s, 1H), 4.11 (t, J = 5.6 Hz, 2H), 3.94 (t, J = 6.0 Hz, 2H), 4.04-3.54 (m, 2H), 3.14-3.00 (m, 2H), 3.45-2.51 (m, 8H), 2.70 (t, J = 6.3 Hz, 3H), 2.10-1.88 (m, 4H), 1.88-1.69 (m, 4H). |
| 87 | 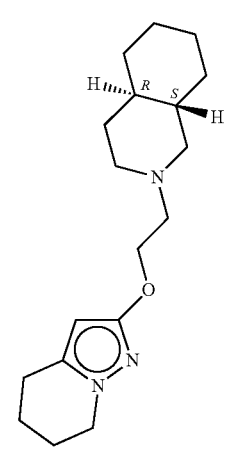 ·C₄H₄O₄ | (4aR,8aS)-2-(2-(4,5,6,7-tetrahydropyrazolo[1,5-a]pyridin-2-yloxy)ethyl)decahydro-isoquinoline maleate | $^1$H NMR (CDCl$_3$) δ ppm: 6.28 (s, 2H), 5.36 (s, 1H), 4.54-4.41 (m, 2H), 3.93 (t, J = 6.1 Hz, 2H), 3.79-3.62 (m, 1H), 3.56-3.45 (m, 1H), 3.46-3.37 (m, 2H), 2.91-2.74 (m, 1H), 2.69 (t, J = 6.4 Hz, 2H), 2.47 (t, J = 11.8 Hz, 1H), 2.09-1.92 (m, 2H), 1.90-1.53 (m, 8H), 1.40-1.16 (m, 3H), 1.16-1.01 (m, 2H), 1.00-0.78 (m, 1H). |

| Ex. | Structure | Name | NMR |
|---|---|---|---|
| 88 | 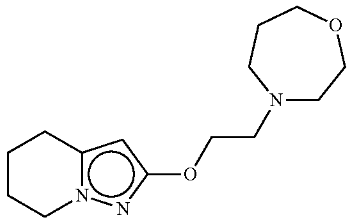 | 4-(2-(4,5,6,7-tetrahydropyrazolo[1,5-a]pyridin-2-yloxy)ethyl)-1,4-oxazepane maleate | ¹H NMR (CDCl₃) δ ppm: 6.28 (s, 2H), 5.36 (s, 1H), 4.58-4.46 (m, 2H), 4.02-3.89 (m, 4H), 3.85 (t, J = 6.3 Hz, 2H), 3.62-3.50 (m, 2H), 3.62-3.30 (m, 4H), 2.70 (t, J = 6.3 Hz, 2H), 2.38-2.20 (m, 2H), 2.12-1.91 (m, 2H), 1.89-1.69 (m, 2H). |
| 89 | 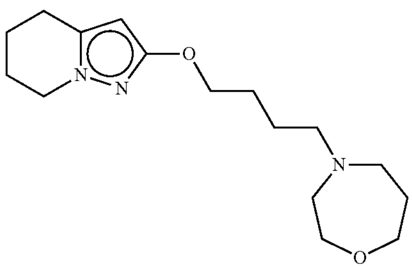 | 4-(4-(4,5,6,7-tetrahydropyrazolo[1,5-a]pyridin-2-yloxy)butyl)-1,4-oxazepane maleate | ¹H NMR (CDCl₃) δ ppm: 6.28 (s, 2H), 5.35 (s, 1H), 4.11 (t, J = 5.7 Hz, 2H), 3.99-3.89 (m, 4H), 3.84 (t, J = 6.3 Hz, 2H), 3.75-2.82 (m, 3H), 3.27-3.11 (m, 2H), 2.70 (t, J = 6.3 Hz, 2H), 2.53-2.07 (m, 1H), 2.07-1.89 (m, 4H), 1.89-1.73 (m, 4H). |
| 90 | 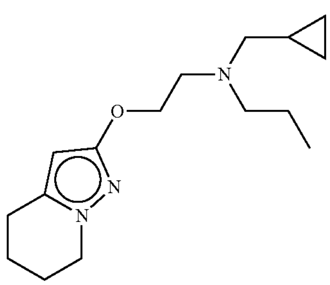 | N-(cyclopropylmethyl)-N-(2-(4,5,6,7-tetrahydropyrazolo[1,5-a]pyridin-2-yloxy)ethyl)propan-1-amine maleate | ¹H NMR (CDCl₃) δ ppm: 6.29 (s, 2H), 5.36 (s, 1H), 4.57-4.44 (m, 2H), 3.94 (t, J = 6.1 Hz, 2H), 3.68-3.52 (m, 2H), 3.30-3.13 (m, 2H), 3.15-3.03 (m, 2H), 2.70 (t, J = 6.3 Hz, 2H), 2.08-1.92 (m, 2H), 1.92-1.69 (m, 4H), 1.18-1.04 (m, 1H), 1.00 (t, J = 7.3 Hz, 3H), 0.88-0.66 (m, 2H), 0.49-0.33 (m, 2H). |
| 91 | 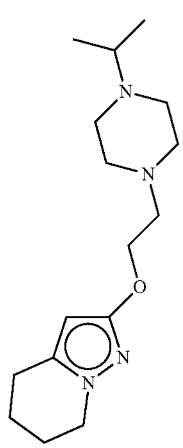 | 2-(2-(4-isopropylpiperazin-1-yl)ethoxy)-4,5,6,7-tetrahydropyrazolo[1,5-a]pyridine maleate | ¹H NMR (CDCl₃) δ ppm: 6.31 (s, 4H), 5.37 (s, 1H), 4.45-4.33 (m, 2H), 3.94 (t, J = 6.0 Hz, 2H), 3.58-3.27 (m, 9H), 3.22-3.10 (m, 2H), 2.69 (t, J = 6.0 Hz, 2H), 2.10-1.95 (m, 4H), 1.87-1.74 (m, 4H), 1.38 (d, J = 6.7 Hz, 6H). |

| Ex. | Structure | Name | NMR |
|---|---|---|---|
| 92 | ·C₄H₄O₄ | 2-(4-(4-isopropylpiperazin-1-yl)butoxy)-4,5,6,7-tetrahydropyrazolo[1,5-a]pyridine maleate | ¹H NMR (CDCl₃) δ ppm: 6.28 (s, 2H), 5.35 (s, 1H), 4.09 (t, J = 5.9 Hz, 2H), 3.94 (t, J = 6.1 Hz, 2H), 3.63-3.17 (m, 2H), 3.08-2.75 (m, 4H), 2.75-2.40 (m, 3H), 2.69 (t, J = 6.3 Hz, 2H), 2.09-1.91 (m, 2H), 1.89-1.72 (m, 4H), 1.71-1.47 (m, 4H), 1.44-1.15 (m, 6H). |
| 93 | ·C₄H₄O₄ | 2-(4-(4-methylpiperazin-1-yl)butoxy)-4,5,6,7-tetrahydropyrazolo[1,5-a]pyridine maleate | ¹H NMR (CDCl₃) δ ppm: 6.28 (s, 2H), 5.35 (s, 1H), 4.09 (t, J = 5.6 Hz, 2H), 3.94 (t, J = 6.1 Hz, 2H), 3.45-2.92 (m, 4H), 2.69 (t, J = 6.3 Hz, 2H), 2.91-2.43 (m, 7H), 2.00 (dt, J = 11.9, 6.0 Hz, 3H), 1.89-1.61 (m, 8H). |
| 94 | ·C₄H₄O₄ | 2-(4-((3S,5R)-3,5-dimethylpiperazin-1-yl)butoxy)-4,5,6,7-tetrahydropyrazolo[1,5-a]pyridine maleate | ¹H NMR (CDCl₃) δ ppm: 6.28 (s, 2H), 5.35 (s, 1H), 4.10 (t, J = 5.4 Hz, 2H), 3.94 (t, J = 6.1 Hz, 2H), 3.65-3.39 (m, 2H), 3.26-3.08 (m, 2H), 2.70 (t, J = 6.3 Hz, 2H), 2.84-2.50 (m, 4H), 2.10-1.93 (m, 2H), 1.89-1.72 (m, 6H), 1.34 (d, J = 6.5 Hz, 6H). |
| 95 | ·C₄H₄O₄ | 1-(4-(4-(4,5,6,7-tetrahydropyrazolo[1,5-a]pyridin-2-yloxy)butyl)piperazin-1-yl)ethanone maleate | ¹H NMR (CDCl₃) δ ppm: 6.32 (s, 2H), 5.40 (s, 1H), 4.12 (t, J = 4.4 Hz, 2H), 4.03-3.84 (m, 6H), 3.18-3.04 (m, 2H), 3.49-2.67 (m, 4H), 2.72 (t, J = 6.1 Hz, 2H), 2.13 (s, 3H), 2.08-1.94 (m, 4H), 1.93-1.68 (m, 4H). |

| Ex. | Structure | Name | NMR |
|---|---|---|---|
| 96 | ·C$_4$H$_4$O$_4$ | 2-(4-(4-methyl-1,4-diazepan-1-yl)butoxy)-4,5,6,7-tetrahydropyrazolo[1,5-a]pyridine maleate | $^1$H NMR (CDCl$_3$) δ ppm: 6.28 (s, 2H), 5.35 (s, 1H), 4.10 (t, J = 5.6 Hz, 2H), 3.93 (t, J = 6.1 Hz, 2H), 3.34-3.15 (m, 6H), 3.13-3.05 (m, 2H), 2.86 (t, J = 7.1 Hz, 2H), 2.72 (s, 3H), 2.70 (t, J = 6.5 Hz, 2H), 2.26-2.13 (m, 2H), 2.05-1.92 (m, 2H), 1.86-1.71 (m, 6H). |
| 97 | ·C$_4$H$_4$O$_4$ | 2-(3-(4-methylpiperazin-1-yl)propoxy)-4,5,6,7-tetrahydropyrazolo[1,5-a]pyridine maleate | $^1$H NMR (CDCl$_3$) δ ppm: 6.28 (s, 2H), 5.35 (s, 1H), 4.14 (t, J = 6.1 Hz, 2H), 3.93 (t, J = 6.1 Hz, 2H), 3.51-2.47 (m, 13H) ,2.75-2.62 (m, 2H), 2.08-1.93 (m, 4H), 1.89-1.70 (m, 2H). |
| 98 | ·C$_4$H$_4$O$_4$ | 2-(4-(4-ethylpiperazin-1-yl)butoxy)-4,5,6,7-tetrahydropyrazolo[1,5-a]pyridine maleate | $^1$H NMR (CDCl$_3$) δ ppm: 6.28 (s, 2H), 5.35 (s, 1H), 4.09 (t, J = 5.8 Hz, 2H), 3.94 (t, J = 6.1 Hz, 2H), 3.50-2.49 (m, 12H), 2.69 (t, J = 6.4 Hz, 2H), 2.07-1.92 (m, 2H), 1.85-1.69 (m, 6H), 1.29 (t, J = 7.2 Hz, 3H). |
| 99 | ·C$_4$H$_4$O$_4$ | 2-(3-(piperidin-1-yl)propoxy)-4,5,6,7-tetrahydropyrazolo[1,5-a]pyridine maleate | $^1$H NMR (CDCl$_3$) δ ppm: 6.28 (s, 2H), 5.35 (s, 1H), 4.19-4.10 (m, 2H), 3.93 (t, J = 6.1 Hz, 2H), 3.66-3.55 (m, 2H), 3.26-3.11 (m, 2H), 2.69 (t, J = 6.4 Hz, 2H), 2.63 (t, J = 9.6 Hz, 2H), 2.30-2.17 (m, 2H), 2.12-1.95 (m, 4H), 1.94-1.74 (m, 3H), 1.48-1.35 (m, 1H). |
| 100 | ·C$_4$H$_4$O$_4$ | 2-(3-(4-cyclohexylpiperazin-1-yl)propoxy)-4,5,6,7-tetrahydropyrazolo[1,5-a]pyridine maleate | $^1$H NMR (CDCl$_3$) δ ppm: 6.27 (s, 2H), 5.35 (s, 1H), 4.13 (t, J = 6.1 Hz, 2H), 3.93 (t, J = 6.1 Hz, 2H), 3.49-3.26 (m, 2H), 3.22-2.72 (m, 9H), 2.69 (t, J = 6.4 Hz, 2H), 2.10 (s, 2H), 2.05-1.86 (m, 4H), 1.86-1.75 (m, 2H), 1.74-1.65 (m, 1H), 1.51-1.06 (m, 7H). |

-continued

| Ex. | Structure | Name | NMR |
|---|---|---|---|
| 101 | 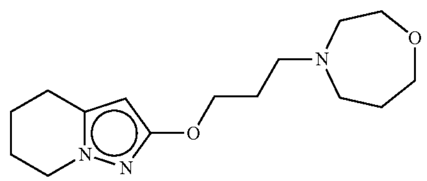 | 4-(3-(4,5,6,7-tetrahydropyrazolo[1,5-a]pyridin-2-yloxy)propyl)-1,4-oxazepane | $^1$H NMR (CDCl$_3$) δ ppm: 5.29 (s, 1H), 4.07 (t, J = 6.2 Hz, 2H), 3.87 (t, J = 6.1 Hz, 2H), 3.79-3.66 (m, 2H), 3.74 (t, J = 6.2 Hz, 2H), 2.91-2.66 (m, 6H), 2.63 (t, J = 6.3 Hz, 2H), 2.08-1.85 (m, 6H), 1.82-1.67 (m, 2H). |
| 102 | ·C$_4$H$_4$O$_4$ | 2-(4-(4-(tetrahydro-2H-pyran-4-yl)piperazin-1-yl)butyltetrahydro-2H-pyran-4-yl)piperazin-1-yl)butoxy)-4,5,6,7-tetrahydropyrazolo[1,5-a]pyridine maleate | $^1$H NMR (CDCl$_3$) δ ppm: 6.27 (s, 2H), 5.34 (s, 1H), 4.09 (t, J = 5.7 Hz, 2H), 4.06-3.99 (m, 2H), 3.93 (t, J = 6.1 Hz, 2H), 3.37 (t, J = 11.6 Hz, 2H), 3.64-2.40 (m, 11H), 2.69 (t, J = 6.4 Hz, 2H), 2.07-1.90 (m, 2H), 1.89-1.73 (m, 10H). |
| 103 | ·C$_4$H$_4$O$_4$ | 1-(4-(3-(4,5,6,7-tetrahydropyrazolo[1,5-a]pyridin-2-yloxy)propyl)piperazin-1-yl)ethanone maleate | $^1$H NMR (CDCl$_3$) δ ppm: 6.31 (s, 2H), 5.37 (s, 1H), 4.18 (t, J = 5.1 Hz, 2H), 4.00-3.82 (m, 6H), 3.35-2.99 (m, 6H), 2.70 (t, J = 6.3 Hz, 4H), 2.35-2.23 (m, 2H), 2.14 (s, 3H), 2.07-1.96 (m, 2H), 1.90-1.73 (m, 4H). |
| 104 | ·C$_4$H$_4$O$_4$ | 4-(2-(4,5,6,7-tetrahydropyrazolo[1,5-a]pyridin-2-yloxy)ethyl)thiomorpholine maleate | $^1$H NMR (CDCl$_3$) δ ppm: 6.29 (s, 2H), 5.36 (s, 1H), 4.60-4.47 (m, 2H), 3.93 (t, J = 6.1 Hz, 2H), 3.54-3.39 (m, 2H), 3.77-2.80 (m, 8H), 2.70 (t, J = 6.3 Hz, 2H), 2.07-1.92 (m, 2H), 1.90-1.72 (m, 2H). |

Synthesis of Compounds of General Formula (Ie)

Example 105

Synthesis of 2-(4-(4-tert-butylpiperidin-1-yl)butoxy)-3-chloro-4,5,6,7-tetrahydropyrazolo[1,5-a]pyridine maleate

105a. Synthesis of 3-chloro-4,5,6,7-tetrahydropyrazolo[1,5-a]pyridin-2-ol

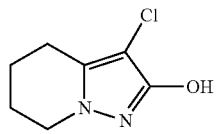

To a solution of 4,5,6,7-tetrahydropyrazolo[1,5-a]pyridin-2-ol (400 mg, 2.895 mmol) in 30 mL of chloroform (CHCl$_3$) at 0° C., N-chlorosuccinimide (425 mg, 3.185 mmol) in 20 mL of CHCl$_3$ was added dropwise for 30 min. The mixture was cooled at 0° C. for additional 30 min. and finally water was added to the cold solution, and the organic layer was separated, washed with water, dried (Na$_2$SO$_4$) and concentrated under vacuum to afford 325 mg of a cream colored solid. The residue was stirred for 18 h in diethyl ether, the mixture filtered and washed with EtOAc. The filtrate was concentrated under vacuum to afford 275 mg of a crude that was purified by column chromatography on silica gel with ether petroleum/EtOAc eluent gradient from 100:0 to 0:100 to give 109 mg (22%) of 3-chloro-4,5,6,7-tetrahydropyrazolo[1,5-a]pyridin-2-ol.

$^1$H NMR (CDCl$_3$) δ ppm: 3.91 (t, J=6.0 Hz, 2H), 2.66 (t, J=6.3 Hz, 2H), 2.09-1.92 (m, 2H), 1.90-1.75 (m, 2H).

105b. Synthesis of 3-chloro-2-(4-chlorobutoxy)-4,5,6,7-tetrahydropyrazolo[1,5-a]pyridine from 3-chloro-4,5,6,7-tetrahydropyrazolo[1,5-a]pyridin-2-ol

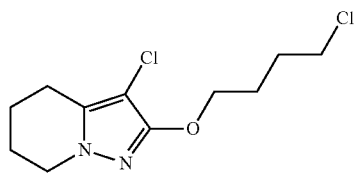 [SMILES: ClCCCCOc1nn2c(c1Cl)CCCC2]

A solution of 3-chloro-4,5,6,7-tetrahydropyrazolo[1,5-a]pyridin-2-ol (52 mg, 0.301 mmol), 1-bromo-4-chlorobutane (69 μL, 0.603 mmol), potassium carbonate (125 mg, 0.904 mmol) and catalytic NaI in 4 mL of DMF, was stirred for 48 h at room temperature protected from incidence of light. The mixture was filtered and concentrated under vacuum. The residue was diluted with diethyl ether and washed with water. The organic layers were dried and evaporated under vacuum to afford 87 mg of yellow oil. A solution of the oil in dichloromethane, was stirred with charcoal and silicagel for 15 min at room temperature. Next, it was filtered and evaporated under vacuum to afford 77 mg (97%) of pale yellow oil.

105c. Synthesis of 2-(4-(4-tert-butylpiperidin-1-yl)butoxy)-3-chloro-4,5,6,7-tetrahydropyrazolo[1,5-a]pyridine maleate (Example 105)

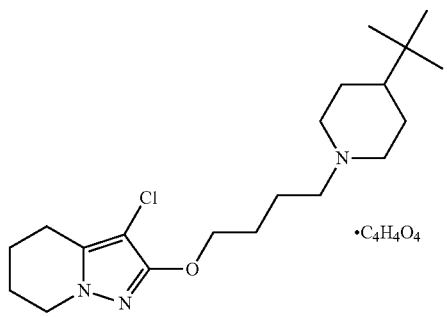

A solution of 3-chloro-2-(4-chlorobutoxy)-4,5,6,7-tetrahydropyrazolo[1,5-a]pyridine (54 mg, 0.205 mmol), potassium carbonate (85 mg, 0.616 mmol), 4-(tert-butyl)piperidine hydrochloride (55 mg, 0.308 mmol) and NaI (catalytic amount) in 2 mL DMF, was heated at 90° C. under nitrogen for 18 h. The mixture was cooled at room temperature and evaporated to dryness. Water and EtOAc were added and the organic layer was washed with water, dried and concentrated under vacuum to give 79 mg of yellow oil purified by flash chromatography on silica gel with EtOAc/MeOH eluent gradient from 100:0 to 80:20 and 1% NH$_4$OH to give 57 mg (75%) of colorless oil. Maleate salt was obtained following the same procedure as for example 1.

$^1$H NMR (CDCl$_3$) δ ppm: 6.26 (s, 2H), 4.22 (t, J=5.6 Hz, 2H), 3.91 (t, J=6.0 Hz, 2H), 3.77-3.59 (m, 2H), 3.20-2.98 (m, 2H), 2.64 (t, J=6.4 Hz, 2H), 2.65-2.46 (m, 2H), 2.09-1.64 (m, 12H), 1.31-1.12 (m, 1H), 0.88 (s, 9H).

Alternatively, example 105 can be obtained from 3-chloro-4,5,6,7-tetrahydro pyrazolo[1,5-a]pyridin-2-ol (compound of formula IVe).

Examples 106 to 108 were prepared according to the procedure described in Example 105 or from compounds of formula (Ia), (Ib), (Ic) or (Id) by direct halogenation with X$_2$ or halosuccinimide (NXS):

| Ex. | Structure | Name | NMR |
|---|---|---|---|
| 106 | 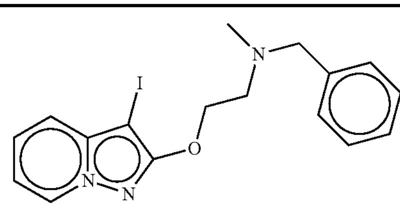 | N-benzyl-2-(3-iodopyrazolo[1,5-a]pyridin-2-yloxy)-N-methylethanamine oxalate | $^1$H NMR (DMSO) δ ppm: 8.53 (d, J = 6.9 Hz, 1H), 7.50-7.26 (m, 7H), 6.82 (dt, J = 7.0, 4.1 Hz, 1H), 4.55 (t, J = 5.0 Hz, 2H), 3.98 (s, 2H), 3.20-3.05 (m, 2H), 2.58-2.50 (m, 3H). |

-continued

| Ex. | Structure | Name | NMR |
|---|---|---|---|
| 107 | 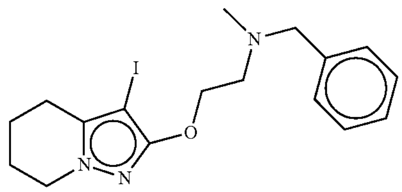 | N-benzyl-2-(3-iodo-4,5,6,7-tetrahydropyrazolo[1,5-a]pyridin-2-yloxy)-N-methylethanamine oxalate •C₂H₂O₄ | ¹H NMR (DMSO) δ ppm: 7.51-7.28 (m, 5H), 4.35 (t, J = 5.1 Hz, 2H), 4.00 (s, 2H), 3.87 (t, J = 5.9 Hz, 2H), 3.18-2.99 (m, 2H), 2.54 (s, 3H), 2.55-2.40 (m, 2H), 1.99-1.83 (m, 2H), 1.83-1.63 (m, 2H). |
| 108 | 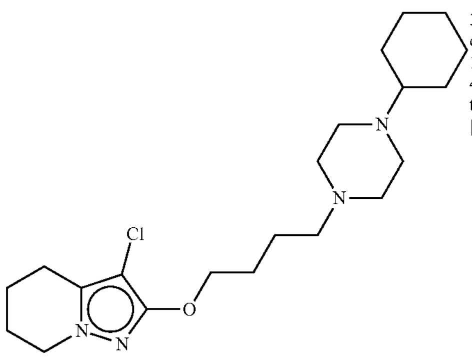 | 3-chloro-2-(4-(4-cyclohexylpiperazin-1-yl)butoxy)-4,5,6,7-tetrahydropyrazolo[1,5-a]pyridine | ¹H NMR (CDCl₃) δ ppm: 4.19 (t, J = 6.5 Hz, 2H), 3.91 (t, J = 6.0 Hz, 2H), 2.71-2.57 (m, 6H), 2.56-2.45 (m, 2H), 2.44-2.33 (m, 2H), 2.30-2.13 (m, 1H), 2.07-1.95 (m, 2H), 1.94-1.72 (m, 8H), 1.72-1.58 (m, 4H), 1.35-1.03 (m, 6H). |

Pharmacological Study

Brain membrane preparation and binding assays for the σ1-receptor were performed as described (DeHaven-Hudkins, D. L., L. C. Fleissner, and F. Y. Ford-Rice, 1992, Characterization of the binding of [³H](+)pentazocine to σ recognition sites in guinea pig brain, Eur. J. Pharmacol. 227, 371-378) with some modifications. Guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was re-suspended in fresh Tris-HCl buffer (50 mM, pH 7.4) and stored on ice until use.

The radioligand used was [³H]-(+)-pentazocine at 5.0 nM and the final volume was 200 μl. The incubation was initiated with the addition of 100 μl of membrane at a final tissue concentration of approximately 5 mg tissue net weight/mL and the incubation time was 150 m. at 37° C. After incubation, the membranes were collected onto pre-treated glass fiber filterplate (MultiScreen-FC, Millipore), with polyethylenimine 0.1%. The filters were washed two times with 200 μl of washing buffer (50 mM Tris Cl, pH=7.4) and then 25 μl of Ecoscint H liquid scintillation cocktail were added. Microplates were allowed to set for several hours and then quantified by liquid scintillation spectrophotometry (1450 Microbeta, Wallac). Nonspecific binding was determined with 1 μM haloperidol.

Pharmacological Results

| Ex. | Ki (nM) |
|---|---|
| 1 | 16.3 |
| 2 | 37.6 |
| 3 | 90.1 |

-continued

| Ex. | Ki (nM) |
|---|---|
| 4 | 48.0 |
| 5 | 42.3 |
| 6 | 23.3 |
| 8 | 22.2 |
| 10 | 75.4 |
| 12 | 19.5 |
| 17 | 117.6 |
| 18 | 14.7 |
| 19 | 74.9 |
| 20 | 50.7 |
| 21 | 3.8 |
| 22 | 3.6 |
| 23 | 30.1 |
| 24 | 4.5 |
| 25 | 19.6 |
| 26 | 11.0 |
| 27 | 9.1 |
| 28 | 19.9 |
| 29 | 11.3 |
| 30 | 6.2 |
| 31 | 21.0 |
| 32 | 14.5 |
| 34 | 5.7 |
| 35 | 10.6 |
| 36 | 20.0 |
| 37 | 14.2 |
| 39 | 6.35 |
| 40 | 41.1 |
| 41 | 14.7 |
| 42 | 3.6 |
| 43 | 28.1 |
| 47 | 14.1 |
| 48 | 15.8 |
| 49 | 7.0 |
| 50 | 9.7 |
| 51 | 8.3 |
| 53 | 25.9 |
| 56 | 180.7 |
| 59 | 167.3 |
| 60 | 40.7 |

-continued

| Ex. | Ki (nM) |
|---|---|
| 61 | 28.5 |
| 63 | 9.2 |
| 64 | 15.4 |
| 65 | 8.3 |
| 66 | 5.5 |
| 67 | 65.7 |
| 68 | 7.3 |
| 69 | 41.6 |
| 70 | 21.6 |
| 71 | 39.3 |
| 72 | 35.0 |
| 74 | 30.6 |
| 75 | 31.7 |
| 78 | 26.1 |
| 80 | 25.0 |
| 81 | 12.8 |
| 82 | 8.1 |
| 83 | 34.8 |
| 84 | 15.7 |
| 85 | 42.5 |
| 86 | 8.4 |
| 87 | 3.3 |
| 89 | 10.1 |
| 90 | 28.5 |
| 91 | 194.8 |
| 92 | 182.3 |
| 93 | 166.8 |
| 96 | 179.5 |
| 98 | 138.5 |
| 99 | 97.2 |
| 100 | 37.1 |
| 101 | 48.1 |
| 105 | 13.3 |
| 106 | 5.8 |
| 107 | 2.95 |
| 108 | 11.4 |

The invention claimed is:

1. A compound of general formula (I):

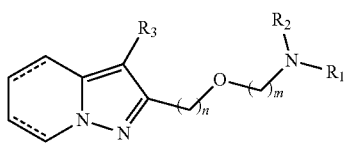

wherein
R$_1$ and R$_2$ independently represent hydrogen; a branched or unbranched, saturated or unsaturated, optionally at least mono-substituted, aliphatic radical C$_{1-10}$; a substituted or unsubstituted aryl radical; a substituted or unsubstituted heteroaryl radical; a substituted or unsubstituted C$_{3-9}$ cycloalkyl radical optionally containing at least one heteroatom as ring member selected from N, O or S; a cycloalkylalkyl radical C$_{1-10}$; an arylalkyl radical C$_{1-10}$; or an heteroarylalkyl radical C$_{1-10}$;
or R$_1$ and R$_2$ together with the bridging nitrogen form a C$_{3-9}$ cycloalkyl optionally having at least one additional heteroatom as a ring member selected from N, O or S and optionally substituted by one or more substituents selected from the group consisting of a C$_{1-6}$ alkyl group, a linear or branched C$_{1-6}$ alkoxy group, —F, —Cl, —I, —Br, —CF$_3$, —CH$_2$F, —CHF$_2$, —CN, —OH, —SH, —NH$_2$, oxo, —(C=O)R', —SR', —SOR', —SO$_2$R', —NHR', —NR'R'',

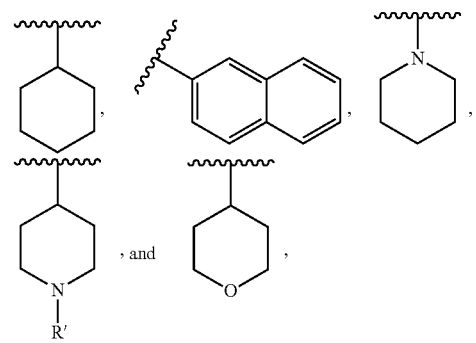

wherein R' and R'' at each occurrence independently represents a linear or branched C$_{1-6}$-alkyl group;
or R$_1$ and R$_2$ together with the bridging nitrogen form C$_{3-9}$ cycloalkyl optionally having at least one additional heteroatom as a ring member selected from N, O or S, which may be condensed to form a ring system with another C$_{3-9}$ cycloalkyl optionally having at least one heteroatom as a ring member selected from N, O or S; or which may be condensed to form a ring system with an aryl radical; or which may be spirofused to an aryl or heteroaryl group;
R$_3$ represents hydrogen or halogen;
n is 0, 1 or 2;
m is 1, 2, 3 or 4;
and - - - - - represents an optional double bond,
with the proviso that when R$_1$ and R$_2$ together with the bridging nitrogen form a piperidine, R$_3$ is hydrogen, n is 0, and m is not 3;
or a pharmaceutically acceptable salt, stereoisomer, or solvate thereof.

2. The compound according to claim 1, wherein R$_1$ and R$_2$ independently represent hydrogen; a branched or unbranched, saturated or unsaturated, optionally at least mono-substituted, aliphatic radical C$_{1-10}$; a substituted or unsubstituted C$_{3-9}$ cycloalkyl radical optionally having at least one heteroatom as ring member selected from N, O or S; a cycloalkylalkyl radical C$_{1-10}$; an arylalkyl radical C$_{1-10}$; or a heteroarylalkyl radical C$_{1-10}$.

3. The compound according to claim 1, wherein R$_1$ and R$_2$ independently represent hydrogen, methyl, ethyl, propyl or a group selected from:

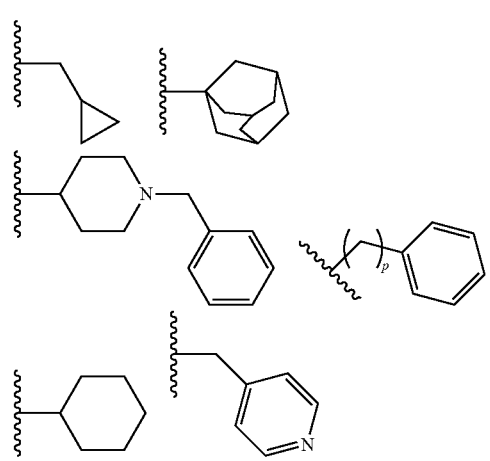

wherein p is 1 or 2.

4. The compound according to claim 1, wherein $R_1$ and $R_2$ together with the bridging nitrogen form a $C_{3-9}$ cycloalkyl optionally having at least one additional heteroatom as a ring member selected from N, O or S and optionally substituted by methyl, ethyl, isopropyl, tertbutyl or a group selected from:

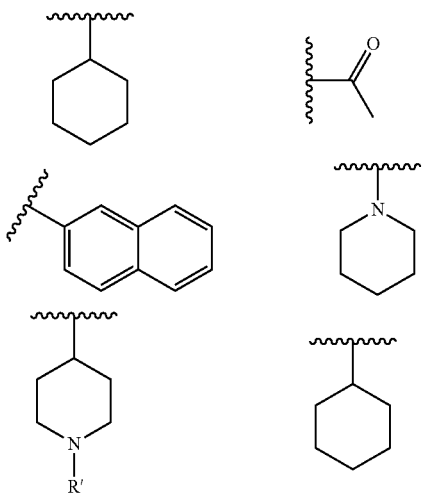

wherein R' is $C_{1-6}$ alkyl.

5. The compound according to claim 1, wherein $R_1$ and $R_2$ together with the bridging nitrogen represents one of the following structures:

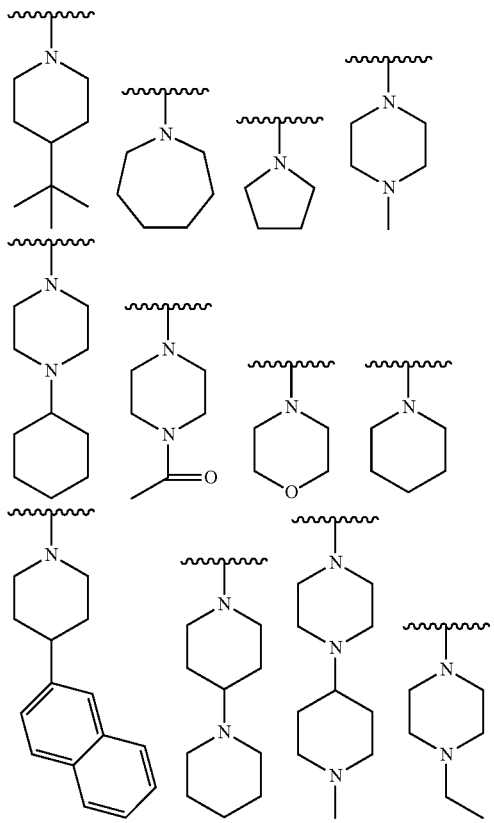

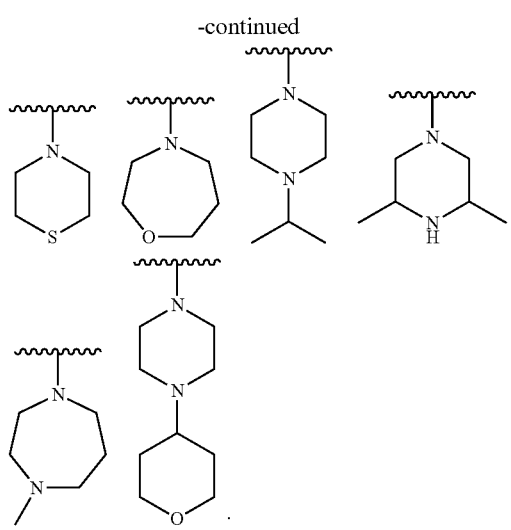

6. The compound according to claim 4, wherein $R_1$ and $R_2$ together with the bridging nitrogen represents one of the following structures:

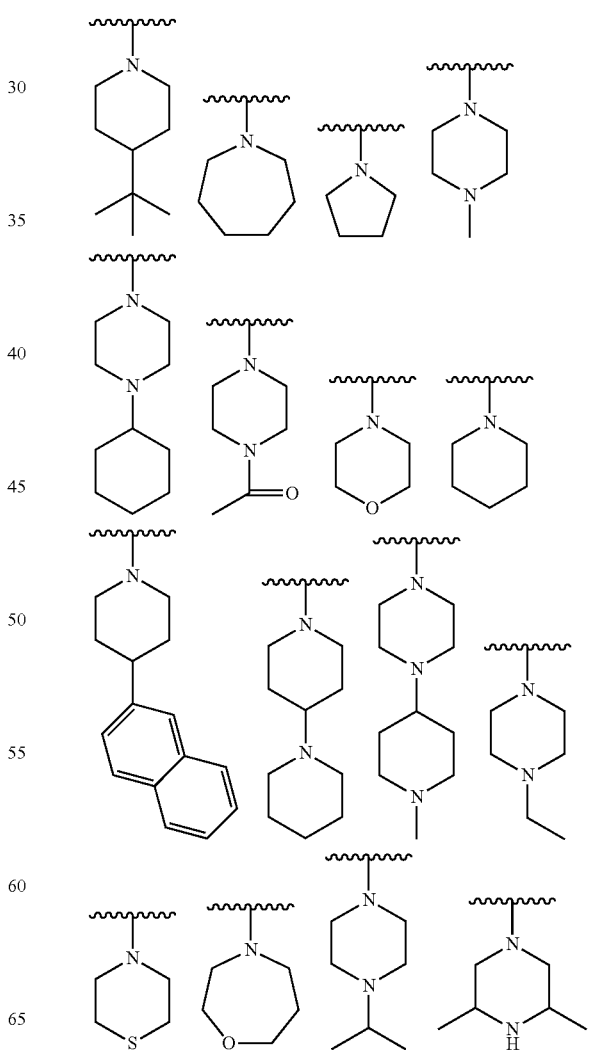

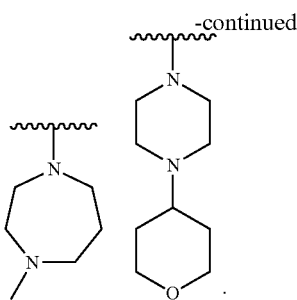

7. The compound according to claim 1, wherein $R_1$ and $R_2$ together with the bridging nitrogen form $C_{3-9}$ cycloalkyl which is condensed or spirofused to another ring or ring system to form one of the following structures:

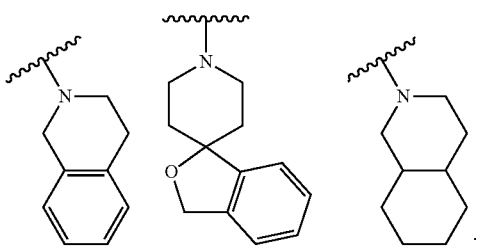

8. The compound according to claim 1, which is selected from:

2-((4-(4-tert-butylpiperidin-1-yl)butoxy)methyl)pyrazolo[1,5-a] pyridine maleate;
2-((2-(azepan-1-yl)ethoxy)methyl)pyrazolo[1,5-a]pyridine maleate;
N-(cyclopropylmethyl)-N-propyl-4-(pyrazolo[1,5-a]pyridin-2-ylmethylpyrazolo[1,5-a]pyridin-2-ylmethoxy)butan-1-amine maleate;
2-(4-(pyrazolo[1,5-a]pyridin-2-ylmethylpyrazolo[1,5-a]pyridin-2-ylmethoxy)butyl)-1,2,3,4-tetrahydroisoquinoline maleate;
N-adamantyl-4-(pyrazolo[1,5-a]pyridin-2-ylmethylpyrazolo[1,5-a]pyridin-2-ylmethoxy)butan-1-amine maleate;
1'-(4-(pyrazolo[1,5-a]pyridin-2-ylmethylpyrazolo[1,5-a]pyridin-2-ylmethoxy)butyl)-3H-spiro[isobenzofuran-1,4'-piperidine] maleate;
2-((2-(pyrrolidin-1-yl)ethoxy)methyl)pyrazolo[1,5-a]pyridine maleate;
2-((4-(azepan-1-yl)butoxy)methyl)pyrazolo[1,5-a]pyridine maleate;
2-((4-(4-methylpiperazin-1-yl)butoxy)methyl)pyrazolo[1,5-a]pyridine maleate;
2-((4-(4-cyclohexylpiperazin-1-yl)butoxy)methyl)pyrazolo[1,5-a]pyridine maleate;
1-(4-(4-(pyrazolo[1,5-a]pyridin-2-ylmethylpyrazolo[1,5-a]pyridin-2-ylmethoxy)butyl)piperazin-1-yl)ethanone;
1-benzyl-N-methyl-N-(4-(pyrazolo[1,5-a]pyridin-2-yloxy)butyl)piperidin-4-amine difumarate;
4-(2-(pyrazolo[1,5-a]pyridin-2-yloxy)ethyl)morpholine;
2-(2-(piperidin-1-yl)ethoxy)pyrazolo[1,5-a]pyridine oxalate;
2-(2-(pyrrolidin-1-yl)ethoxy)pyrazolo[1,5-a]pyridine oxalate;
N,N-diethyl-2-(pyrazolo[1,5-a]pyridin-2-yloxy)ethanamine oxalate;
4-(4-(pyrazolo[1,5-a]pyridin-2-yloxy)butyl)morpholine oxalate;
2-(4-(piperidin-1-yl)butoxy)pyrazolo[1,5-a]pyridine oxalate;
N,N-diethyl-4-(pyrazolo[1,5-a]pyridin-2-yloxy)butan-1-amine oxalate;
2-(4-(pyrrolidin-1-yl)butoxy)pyrazolo[1,5-a]pyridine oxalate;
N-benzyl-N-methyl-4-(pyrazolo[1,5-a]pyridin-2-yloxy)butan-1-amine oxalate;
N-benzyl-N-methyl-2-(pyrazolo[1,5-a]pyridin-2-yloxy)ethanamine oxalate;
2-(4-(4-(naphthalen-2-yl)piperidin-1-yl)butoxy)pyrazolo[1,5-a]pyridine;
1'-(4-(pyrazolo[1,5-a]pyridin-2-yloxy)butyl)-3H-spiro[isobenzofuran-1,4'-piperidine] oxalate;
2-(4-(4-cyclohexylpiperazin-1-yl)butoxy)pyrazolo[1,5-a]pyridine2-(4-(4-cyclohexylpiperazin-1-yl)butoxy)pyrazolo[1,5-a]pyridine dimaleate;
2-(4-(4-tert-butylpiperidin-1-yl)butoxy)pyrazolo[1,5-a]pyridine hydrochloride;
N-methyl-N-phenethyl-4-(pyrazolo[1,5-a]pyridin-2-yloxy)butan-1-amine hydrochloride;
N-methyl-4-(pyrazolo[1,5-a]pyridin-2-yloxy)-N-(pyridin-4-ylmethyl)butan-1-amine dihydrochloride;
2-(4-(1,4'-bipiperidin-1'-yl)butoxy)pyrazolo[1,5-a]pyridine difumarate;
2-(4-(pyrazolo[1,5-a]pyridin-2-yloxy)butyl)decahydroisoquinoline fumarate;
N-(cyclopropylmethyl)-N-propyl-4-(pyrazolo[1,5-a]pyridin-2-yloxy)butan-1-amine maleate;
2-(4-(pyrazolo[1,5-a]pyridin-2-yloxy)butyl)-1,2,3,4-tetrahydroisoquinoline maleate;
N-adamantyl-4-(pyrazolo[1,5-a]pyridin-2-yloxy)-butan-1-amine maleate;
2-(4-(4-(1-methylpiperidin-4-yl)piperazin-1-yl)butoxy)pyrazolo[1,5-a]pyridine dimaleate;
2-(2-(4-tert-butylpiperidin-1-yl)ethoxy)pyrazolo[1,5-a]pyridine maleate;
N-methyl-N-phenethyl-2-(pyrazolo[1,5-a]pyridin-2-yloxy)ethanamine maleate;
1-benzyl-N-methyl-N-(2-(pyrazolo[1,5-a]pyridin-2-yloxy)ethyl)piperidin-4-amine dimaleate;
2-(2-(pyrazolo[1,5-a]pyridin-2-yloxy)ethyl)decahydroisoquinoline maleate;
N-(cyclopropylmethyl)-N-(2-(pyrazolo[1,5-a]pyridin-2-yloxy)ethyl)propan-1-amine maleate;
2-(2-(pyrazolo[1,5-a]pyridin-2-yloxy)ethyl)-1,2,3,4-tetrahydroisoquinoline maleate;
2-(2-(1,4'-bipiperidin-1'-yl)ethoxy)pyrazolo[1,5-a]pyridine dimaleate;
2-(2-(4-(1-methylpiperidin-4-yl)piperazin-1-yl)ethoxy)pyrazolo[1,5-a]pyridine dimaleate;
2-(2-(4-cyclohexylpiperazin-1-yl)ethoxy)pyrazolo[1,5-a]pyridine dimaleate;
1'-(2-(pyrazolo[1,5-a]pyridin-2-yloxy)ethyl)-3H-spiro[isobenzofuran-1,4'-piperidine] dimaleate;
2-(4-(azepan-1-yl)butoxy)pyrazolo[1,5-a]pyridine maleate;
N-(4-(pyrazolo[1,5-a]pyridin-2-yloxy)butyl)cyclohexanamine maleate;
(4aR,8aS)-2-(4-(pyrazolo[1,5-a]pyridin-2-yloxy)butyl)decahydroisoquinoline maleate;
2-(2-(4-ethylpiperazin-1-yl)ethoxy)-4,5,6,7-tetrahydropyrazolo [1,5-a]pyridine maleate;
2-(2-(azepan-1-yl)ethoxy)-4,5,6,7-tetrahydropyrazolo[1,5-a] pyridine maleate;

2-(2-(piperidin-1-yl)ethoxy)-4,5,6,7-tetrahydropyrazolo[1,5-a]pyridine oxalate;
N,N-diethyl-2-(4,5,6,7-tetrahydropyrazolo[1,5-a]pyridin-2-yloxy)ethanamine oxalate;
4-(4-(4,5,6,7-tetrahydropyrazolo[1,5-a]pyridin-2-yloxy)butyl)morpholine oxalate;
4-(2-(4,5,6,7-tetrahydropyrazolo[1,5-a]pyridin-2-yloxy)ethyl)morpholine oxalate;
2-(2-(pyrrolidin-1-yl)ethoxy)-4,5,6,7-tetrahydropyrazolo[1,5-a]pyridine oxalate;
2-(4-(pyrrolidin-1-yl)butoxy)-4,5,6,7-tetrahydropyrazolo[1,5-a]pyridine oxalate;
2-(4-(piperidin-1-yl)butoxy)-4,5,6,7-tetrahydropyrazolo[1,5-a]pyridine oxalate;
2-(4-(piperidin-1-yl)butoxy)-4,5,6,7-tetrahydropyrazolo[1,5-a]pyridine maleate;
N,N-diethyl-4-(4,5,6,7-tetrahydropyrazolo[1,5-a]pyridin-2-yloxy)butan-1-amine oxalate;
N-benzyl-N-methyl-2-(4,5,6,7-tetrahydropyrazolo[1,5-a]pyridin-2-yloxy)ethanamine oxalate;
2-(4-(4-tert-butylpiperdin-1-yl)butoxy)-4,5,6,7-tetrahydropyrazolo[1,5-a]pyridine maleate;
2-(2-(4-tert-butylpiperidin-1-yl)ethoxy)-4,5,6,7-tetrahydropyrazolo[1,5-a]pyridine maleate;
1-benzyl-N-methyl-N-(4-(4,5,6,7-tetrahydropyrazolo[1,5-a]pyridin-2-yloxy)butyl)piperidin-4-amine dimaleate;
2-(4-(4,5,6,7-tetrahydropyrazolo[1,5-a]pyridin-2-yloxy)butyl)decahydroisoquinoline maleate;
2-(4-(4-cyclohexylpiperazin-1-yl)butoxy)-4,5,6,7-tetrahydropyrazolo[1,5-a]pyridine maleate:
1'-(4-(4,5,6,7-tetrahydropyrazolo[1,5-a]pyridin-2-yloxy)butyl)-3H-spiro[isobenzofuran-1,4'-piperidine] maleate;
2-(2-(4-cyclohexylpiperazin-1-yl)ethoxy)-4,5,6,7-tetrahydropyrazolo[1,5-a]pyridine maleate;
1-benzyl-N-methyl-N-(2-(4,5,6,7-tetrahydropyrazolo[1,5-a]pyridin-2-yloxy)ethyl)piperidin-4-amine maleate;
2-(2-(4-(1-methylpiperidin-4-yl)piperazin-1-yl)ethoxy)-4,5,6,7-tetrahydropyrazolo[1,5-a]pyridine maleate;
1'-(2-(4,5,6,7-tetrahydropyrazolo[1,5-a]pyridin-2-yloxy)ethyl)-3H-spiro[isobenzofuran-1,4'-piperidine] maleate;
N-adamantyl-2-(4,5,6,7-tetrahydropyrazolo[1,5-a]pyridin-2-yloxy)ethanamine maleate;
2-(2-(1,4'-bipiperidin-1'-yl)ethoxy)-4,5,67-tetrahydropyrazolo[1,5-a]pyridine maleate;
2-(2-(4,5,6,7-tetrahydropyrazolo[1,5-a]pyridin-2-yloxy)ethyl)-1,2,3,4-tetrahydroisoquinoline maleate;
2-(4-(azepan-1-yl)butoxy)-4,5,6,7-tetrahydropyrazolo[1,5-a]pyridine maleate
2-(4-(1,4'-bipiperidin-1'-yl)butoxy)-4,5,6,7-tetrahydropyrazolo[1,5-a]pyridine maleate;
N-(cyclopropylmethyl)-N-propyl-4-(4,5,6,7-tetrahydropyrazolo[1,5-a]pyridin-2-yloxy)butan-1-amine maleate;
(4aR,8aS)-2-(4-(4,5,6,7-tetrahydropyrazolo[1,5-a]pyridin-2-yloxy)butyl)decahydroisoquinoline maleate;
N-benzyl-N-methyl-4-(4,5,6,7-tetrahydropyrazolo[1,5-a]pyridin-2-yloxy)butan-1-amine maleate;
N-adamantyl-4-(4,5,6,7-tetrahydropyrazolo[1,5-a]pyridin-2-yloxy)butan-1-amine maleate;
2-(4-(4,5,6,7-tetrahydropyrazolo[1,5-a]pyridin-2-yloxy)butyl)-1,2,3,4-tetrahydroisoquinoline maleate;
N-(4-(4,5,6,7-tetrahydropyrazolo[1,5-a]pyridin-2-yloxy)butyl)cyclohexanamine maleate;
4-(4-(4,5,6,7-tetrahydropyrazolo[1,5-a]pyridin-2-yloxy)butyl)thiomorpholine maleate;
(4aR,8aS)-2-(2-(4,5,6,7-tetrahydropyrazolo[1,5-a]pyridin-2-yloxy)ethyl)decahydroisoquinoline maleate;
4-(2-(4,5,6,7-tetrahydropyrazolo[1,5-a]pyridin-2-yloxy)ethyl)-1,4-oxazepane maleate;
4-(4-(4,5,6,7-tetrahydropyrazolo[1,5-a]pyridin-2-yloxy)butyl)-1,4-oxazepane maleate;
N-(cyclopropylmethyl)-N-(2-(4,5,6,7-tetrahydropyrazolo[1,5-a]pyridin-2-yloxy)ethyl)propan-1-amine maleate;
2-(2-(4-isopropylpiperazin-1-yl)ethoxy)-4,5,6,7-tetrahydropyrazolo[1,5-a]pyridine maleate;
2-(4-(4-isopropylpiperazin-1-yl)butoxy)-4,5,6,7-tetrahydropyrazolo[1,5-a]pyridine maleate;
2-(4-(4-methylpiperazin-1-yl)butoxy)-4,5,6,7-tetrahydropyrazolo[1,5-a]pyridine maleate;
2-(4-((3S,5R)-3,5-dimethylpiperazin-1-yl)butoxy)-4,5,6,7-tetrahydropyrazolo[1,5-a]pyridine maleate;
1-(4-(4-(4,5,6,7-tetrahydropyrazolo[1,5-a]pyridin-2-yloxy)butyl)piperazin-1-yl)ethanone maleate;
2-(4-(4-methyl-1,4-diazepan-1-yl)butoxy)-4,5,6,7-tetrahydropyrazolo[1,5-a]pyridine maleate;
2-(3-(4-methylpiperazin-1-yl)propoxy)-4,5,6,7-tetrahydropyrazolo[1,5-a]pyridine maleate;
2-(4-(4-ethylpiperazin-1-yl)butoxy)-4,5,6,7-tetrahydropyrazolo[1,5-a]pyridine maleate;
2-(3-(piperidin-1-yl)propoxy)-4,5,6,7-tetrahydropyrazolo[1,5-a]pyridine maleate;
2-(3-(4-cyclohexylpiperazin-1-yl)propoxy)-4,5,6,7-tetrahydropyrazolo[1,5-a]pyridine maleate;
4-(3-(4,5,6,7-tetrahydropyrazolo[1,5-a]pyridin-2-yloxy)propyl)-1,4-oxazepane;
2-(4-(4-(tetrahydro-2H-pyran-4-yl)piperazin-1-yl)butyltetrahydro-2H-pyran-4-yl)piperazin-1-yl)butoxy)-4,5,6,7-tetrahydropyrazolo[1,5-a]pyridine maleate;
1-(4-(3-(4,5,6,7-tetrahydropyrazolo[1,5-a]pyridin-2-yloxy)propyl)piperazin-1-yl)ethanone maleate;
4-(2-(4,5,6,7-tetrahydropyrazolo[1,5-a]pyridin-2-yloxy)ethyl)thiomorpholine maleate;
2-(4-(4-tert-butylpiperidin-1-yl)butoxy)-3-chloro-4,5,6,7-tetrahydropyrazolo[1,5-a]pyridine maleate;
3-chloro-2-(4-chlorobutoxy)-4,5,6,7-tetrahydropyrazolo[1,5-a]pyridine from 3-chloro-4,5,6,7-tetrahydropyrazolo[1,5-a]pyridin-2-ol;
2-(4-(4-tert-butylpiperidin-1-yl)butoxy)-3-chloro-4,5,6,7-tetrahydropyrazolo[1,5-a]pyridine maleate;
N-benzyl-2-(3-iodopyrazolo[1,5-a]pyridin-2-yloxy)-N-methylethanamine oxalate;
N-benzyl-2-(3-iodo-4,5,6,7-tetrahydropyrazolo[1,5-a]pyridin-2-yloxy)-N-methylethanamine oxalate; and
3-chloro-2-(4-(4-cyclohexylpiperazin-1-yl)butoxy)-4,5,6,7-tetrahydropyrazolo[1,5-a]pyridine.

9. A process for the preparation of a compound of general formula (Ia) or (Ib):

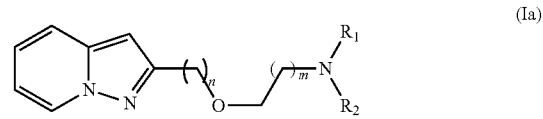
(Ia)

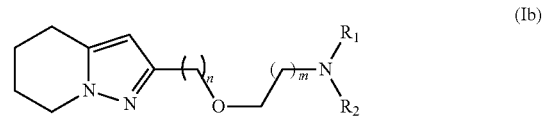
(Ib)

comprising reaction of respectively compounds of formula (IIa) or (IIb):

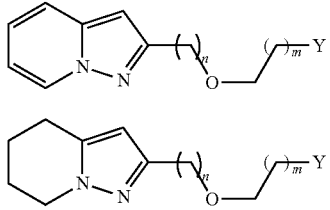
(IIa)

(IIb)

with a compound of formula (III):

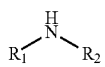
(III)

in an organic solvent, in the presence of an organic or inorganic base and optionally in the presence of an activating agent,
wherein
R₁ and R₂ independently represent hydrogen; a branched or unbranched, saturated or unsaturated, optionally at least mono-substituted, aliphatic radical $C_{1-10}$; a substituted or unsubstituted aryl radical; a substituted or unsubstituted heteroaryl radical; a substituted or unsubstituted $C_{3-9}$ cycloalkyl radical optionally containing at least one heteroatom as ring member selected from N, O or S; a cycloalkylalkyl radical $C_{1-10}$; an arylalkyl radical $C_{1-10}$; or an heteroarylalkyl radical $C_{1-10}$;
or R₁ and R₂ together with the bridging nitrogen form a $C_{3-9}$ cycloalkyl optionally having at least one additional heteroatom as a ring member selected from N, O or S and optionally substituted; by one or more substituents selected from the group consisting of a $C_{3-6}$ alkyl group, a linear or branched $C_{1-6}$ alkoxy group, —F, —Cl, —I, —Br, —CF₃, —CH₂F, —CHF₂, —CN, —OH, —SH, —NH₂, oxo, —(C=O)R', —SR', —SOR', —SO₂R', —NHR', —NR'R",

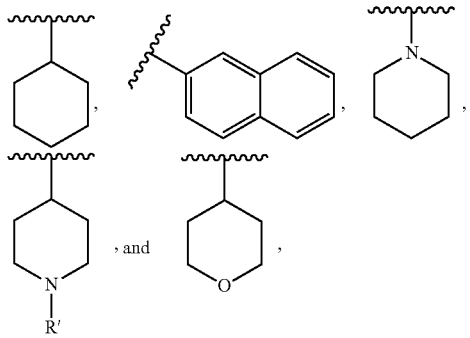

wherein R' and R" at each occurrence independently represents a linear or branched $C_{1-6}$-alkyl group;
or R₁ and R₂ together with the bridging nitrogen form $C_{3-9}$ cycloalkyl optionally having at least one additional heteroatom as a ring member selected from N, O or S, which may be condensed to form a ring system with another $C_{3-9}$ cycloalkyl optionally having at least one heteroatom as a ring member selected from N, O or S; or which may be condensed to form a ring system with an aryl radical; or which may be spirofused to an aryl or heteroaryl group;
n is 0, 1 or 2;
m is 1, 2, 3 or 4;
and Y is a leaving group.

10. A process for the preparation of a compound of general formula (Ia) or (Ib):

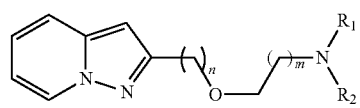
(Ia)

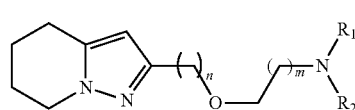
(Ib)

comprising reaction of respectively a compound of formula (IVa) and (IVb):

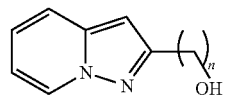
(IVa)

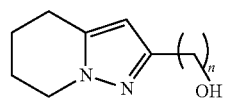
(IVb)

with a compound of formula (V):

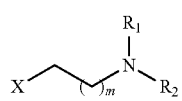
(V)

in an organic solvent, in the presence of an organic or inorganic base and optionally in the presence of an activating agent,
wherein
R₁ and R₂ independently represent hydrogen; a branched or unbranched, saturated or unsaturated, optionally at least mono-substituted, aliphatic radical $C_{1-10}$; a substituted or unsubstituted aryl radical; a substituted or unsubstituted heteroaryl radical; a substituted or unsubstituted $C_{3-9}$ cycloalkyl radical optionally containing at least one heteroatom as ring member selected from N, O or S; a cycloalkylalkyl radical $C_{1-10}$; an arylalkyl radical $C_{1-10}$; or an heteroarylalkyl radical $C_{1-10}$;
or R₁ and R₂ together with the bridging nitrogen form a $C_{3-9}$ cycloalkyl optionally having at least one additional heteroatom as a ring member selected from N, O or S and optionally substituted; by one or more substituents selected from the group consisting of a $C_{1-6}$ alkyl group, a linear or branched $C_{1-6}$ alkoxy group, —F, —Cl, —I, —Br, —CF₃, —CH₂F, —CHF₂, —CN, —OH, —SH, —NH₂, oxo, —(C=O)R', —SR', —SOR', —SO₂R', —NHR', —NR'R",

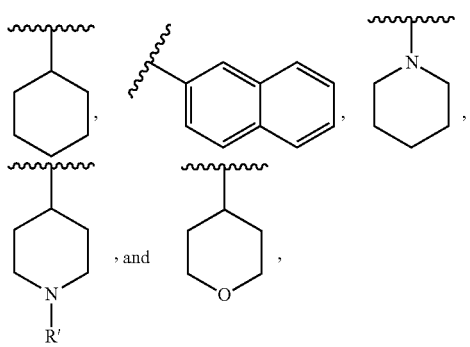

wherein R' and R" at each occurrence independently represents a linear or branched $C_{1-6}$-alkyl group;

or $R_1$ and $R_2$ together with the bridging nitrogen form $C_{3-9}$ cycloalkyl optionally having at least one additional heteroatom as a ring member selected from N, O or S, which may be condensed to form a ring system with another $C_{3-9}$ cycloalkyl optionally having at least one heteroatom as a ring member selected from N, O or S; or which may be condensed to form a ring system with an aryl radical; or which may be spirofused to an aryl or heteroaryl group;

n is 0, 1 or 2;

m is 1, 2, 3 or 4;

and X is a leaving group.

11. A process for the preparation of compounds of general formula (Ic) or (Id):

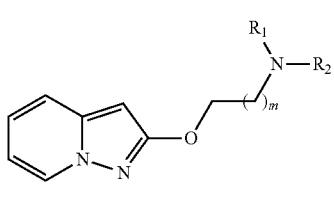

(Ic)

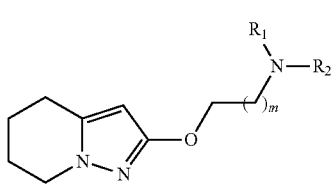

(Id)

comprising reaction of respectively a compound of formula (IIc) or (IId):

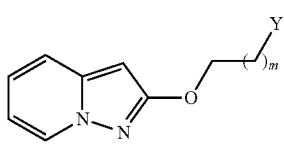

(IIc)

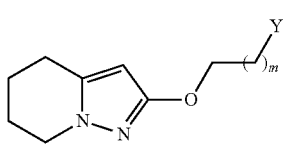

(IId)

with a compound of formula (III):

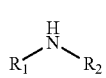

(III)

in water or an organic solvent, in the presence of an organic or inorganic base and optionally in the presence of an activating agent, wherein $R_1$ and $R_2$ independently represent hydrogen; a branched or unbranched, saturated or unsaturated, optionally at least mono-substituted, aliphatic radical $C_{1-10}$; a substituted or unsubstituted aryl radical; a substituted or unsubstituted heteroaryl radical; a substituted or unsubstituted $C_{3-9}$ cycloalkyl radical optionally containing at least one heteroatom as ring member selected from N, O or S; a cycloalkylalkyl radical $C_{1-10}$; an arylalkyl radical $C_{1-10}$; or an heteroarylalkyl radical $C_{1-10}$;

or $R_1$ and $R_2$ together with the bridging nitrogen form a $C_{3-9}$ cycloalkyl optionally having at least one additional heteroatom as a ring member selected from N, O or S and optionally substituted by one or more substituents selected from the group consisting of a $C_{1-6}$ alkyl group, a linear or branched $C_{1-6}$ alkoxy group, —F, —Cl, —I, —Br, —CF$_3$, —CH$_2$F, —CHF$_2$, —CN, —OH, —SH, —NH$_2$, oxo, —(C═)R', —SR', —SO$_2$R', —NHR', —NR'R",

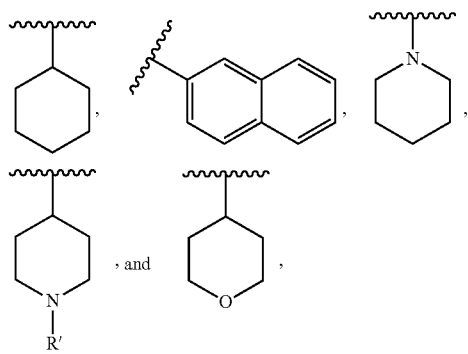

wherein R' and R" at each occurrence independently represents a linear or branched $C_{1-6}$-alkyl group;

or $R_1$ and $R_2$ together with the bridging nitrogen form $C_{3-9}$ cycloalkyl optionally having at least one additional heteroatom as a ring member selected from N, O or S, which may be condensed to form a ring system with another $C_{3-9}$ cycloalkyl optionally having at least one heteroatom as a ring member selected from N, O or S; or which may be condensed to form a ring system with an aryl radical; or which may be spirofused to an aryl or heteroaryl group;

n is 0, 1 or 2;

m is 1, 2, 3 or 4;

and Y is a leaving group.

12. A process for the preparation of a compound of general formula (Ic) or (Id):

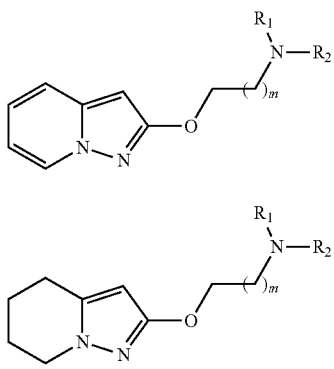

comprising reaction of respectively a compound of formula (IVc) or (IVd):

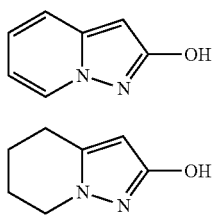

with a compound of formula (V):

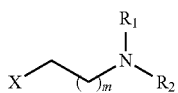

in an organic solvent, in the presence of an organic or inorganic base and optionally in the presence of an activating agent, wherein $R_1$ and $R_2$ independently represent hydrogen; a branched or unbranched, saturated or unsaturated, optionally at least mono-substituted, aliphatic radical $C_{1-10}$; a substituted or unsubstituted aryl radical; a substituted or unsubstituted heteroaryl radical; a substituted or unsubstituted $C_{3-9}$ cycloalkyl radical optionally containing at least one heteroatom as ring member selected from N, O or S; a cycloalkylalkyl radical $C_{1-10}$; an arylalkyl radical $C_{1-10}$; or an heteroarylalkyl radical $C_{1-10}$;

or $R_1$ and $R_2$ together with the bridging nitrogen form a $C_{3-9}$ cycloalkyl optionally having at least one additional heteroatom as a ring member selected from N, O or S and optionally substituted; by one or more substituents selected from the group consisting of a $C_{1-6}$ alkyl group, a linear or branched $C_{1-6}$ alkoxy group, —F, —Cl, —I, —Br, —CF$_3$, —CH$_2$F, —CHF$_2$, —CN, —OH, —SH, —NH$_2$, oxo, —(C=O)R', —SR', —SOR', —SO$_2$R', —NHR', —NR'R",

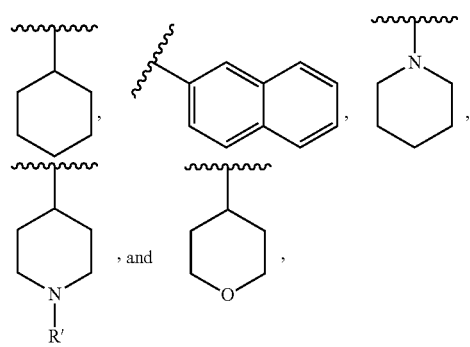

wherein R' and R" at each occurrence independently represents a linear or branched $C_{1-6}$-alkyl group;

or $R_1$ and $R_2$ together with the bridging nitrogen form $C_{3-9}$ cycloalkyl optionally having at least one additional heteroatom as a ring member selected from N, O or S, which may be condensed to form a ring system with another $C_{3-9}$ cycloalkyl optionally having at least one heteroatom as a ring member selected from N, O or S; or which may be condensed to form a ring system with an aryl radical; or which may be spirofused to an aryl or heteroaryl group;

n is 0, 1 or 2;

m is 1, 2, 3 or 4;

and X is a leaving group.

13. A process for the preparation of a compound of general formula (Ie):

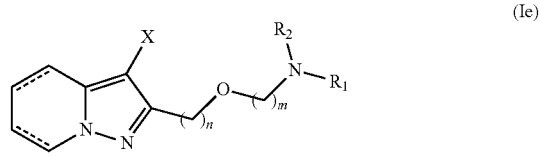

wherein $R_1$ and $R_2$ independently represent hydrogen; a branched or unbranched, saturated or unsaturated, optionally at least mono-substituted, aliphatic radical $C_{1-10}$; a substituted or unsubstituted aryl radical; a substituted or unsubstituted heteroaryl radical; a substituted or unsubstituted $C_{3-9}$ cycloalkyl radical optionally containing at least one heteroatom as ring member selected from N, O or S; a cycloalkylalkyl radical $C_{1-10}$; an arylalkyl radical $C_{1-10}$: or an heteroarylalkyl radical $C_{1-10}$;

or $R_1$ and $R_2$ together with the bridging nitrogen form a $C_{3-9}$ cycloalkyl optionally having at least one additional heteroatom as a ring member selected from N, O or S and optionally substituted by one or more substituents selected from the group consisting of a $C_{1-6}$ alkyl group, a linear or branched $C_{1-6}$ alkoxy group, —F, —Cl, —I, —BR, —CF$_3$, —CH$_2$F, —CHF$_2$, —CN, —OH, —SH, —NH$_2$, oxo, —(C=O)R', —SR', —SOR', —SO$_2$R', —NHR', —NR'R",

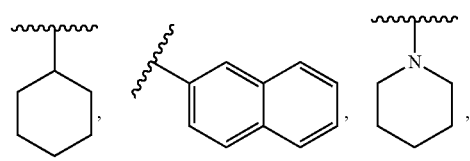

-continued

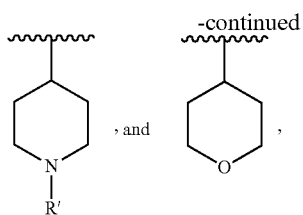, and , wherein R' and R" at each occurrence independently represents a linear or branched $C_{1-6}$-alkyl group;

or $R_1$ and $R_2$ together with the bridging nitrogen form $C_{3-9}$ cycloalkyl optionally having at least one additional heteroatom as a ring member selected from N, O or S, which may be condensed to form a ring system with another $C_{3-9}$ cycloalkyl optionally having at least one heteroatom as a ring member selected from N, O or S; or which may be condensed to form a ring system with an aryl radical; or which may be spirofused to an aryl or heteroaryl group;

n is 0, 1 or 2;
m is 1, 2, 3 or 4;
and X is a halogen,
the process comprising the direct halogenation with $X_2$ or halosuccinimide of a compound of formula (VII):

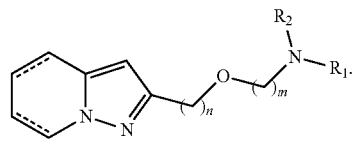

(VII)

14. A pharmaceutical composition comprising a compound of general formula (I) according to claim 1, or a pharmaceutically acceptable salt, stereoisomer, or solvate thereof, and at least a pharmaceutically acceptable carrier, additive, adjuvant or vehicle.

* * * * *

UNITED STATES PATENT AND TRADEMARK OFFICE
CERTIFICATE OF CORRECTION

PATENT NO. : 9,487,513 B2
APPLICATION NO. : 14/379844
DATED : November 8, 2016
INVENTOR(S) : José-Luís Díaz-Fernández and Ma Rosa Cuberes Altisent It is certified that error appears in the above-identified patent and that said Letters Patent is hereby corrected as shown below:

On the Title Page

Item (73), assignee: "LABORATORIOS DE DR. ESTEVE S.A." should be
--LABORATORIOS DEL DR. ESTEVE S.A.--.

In the Claims

Column 94, Line 29: "-OH, -SH, -NH$_2$, oxo, -(C = =)R', -SR'," should be
-- -OH, -SH, -NH$_2$, oxo, -(C = O)R', -SR', SOR',--.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*